US012594026B1

(12) United States Patent
Shaw

(10) Patent No.: US 12,594,026 B1
(45) Date of Patent: Apr. 7, 2026

(54) AURICULAR SLEEP MONITORING SYSTEMS AND EAR-CANAL PULSE OXIMETER

(71) Applicant: David C. Shaw, Torrance, CA (US)

(72) Inventor: David C. Shaw, Torrance, CA (US)

( * ) Notice: Subject to any disclaimer, the term of this patent is extended or adjusted under 35 U.S.C. 154(b) by 0 days.

(21) Appl. No.: 19/306,431

(22) Filed: Aug. 21, 2025

Related U.S. Application Data

(60) Provisional application No. 63/834,109, filed on Feb. 21, 2025.

(51) Int. Cl.
| | |
|---|---|
| *A61B 5/00* | (2006.01) |
| *A61B 5/1455* | (2006.01) |
| *A61B 5/28* | (2021.01) |
| *A61B 5/291* | (2021.01) |
| *A61B 5/297* | (2021.01) |
| *A61B 5/318* | (2021.01) |
| *A61B 5/369* | (2021.01) |

(52) U.S. Cl.
CPC .......... *A61B 5/4818* (2013.01); *A61B 5/1455* (2013.01); *A61B 5/14552* (2013.01); *A61B 5/28* (2021.01); *A61B 5/291* (2021.01); *A61B 5/297* (2021.01); *A61B 5/318* (2021.01); *A61B 5/369* (2021.01); *A61B 5/6803* (2013.01); *A61B 5/6817* (2013.01); *A61B 5/7405* (2013.01); *A61B 5/742* (2013.01); *A61B 5/7455* (2013.01); *A61B 5/746* (2013.01)

(58) Field of Classification Search
None
See application file for complete search history.

(56) References Cited

U.S. PATENT DOCUMENTS

| | | | |
|---|---|---|---|
| 11,253,674 B2 | 2/2022 | Le Van Quyen et al. | |
| 11,623,079 B2 | 4/2023 | Simon et al. | |
| 11,716,580 B2 | 8/2023 | Solum et al. | |
| 11,931,175 B2 | 3/2024 | Pintat et al. | |
| 2015/0150501 A1* | 6/2015 | George | A61B 5/6817 |
| | | | 600/301 |
| 2018/0103858 A1 | 4/2018 | Marcus et al. | |
| 2019/0380597 A1* | 12/2019 | Howard | A61B 5/318 |
| 2021/0100508 A1* | 4/2021 | Vos | H04R 25/554 |

(Continued)

*Primary Examiner* — Michael W Kahelin
(74) *Attorney, Agent, or Firm* — PATENTFILE, LLC; Bradley C. Fach; Steven R. Kick

(57) ABSTRACT

Novel auricular sleep monitoring systems and ear-canal pulse oximeter may be configured to be coupled to a wearer's ear or peri-auricular area. The sleep monitoring systems may include one or more of an auricular electrooculogram (EOG) system; an auricular electroencephalogram (EEG) system; an auricular electrocardiogram (ECG) system; and an ancillary sleep surveillance system, comprising a conventional pulse oximeter or a novel ear-canal pulse oximeter and other sleep-relevant sensors. A processing unit may be configured to analyze data from EOG system, EEG system, ECG system, pulse oximeter and other sleep-relevant sensors to assess the wearer's sleep profile. When obstructive sleep apnea is detected, a notification may be automatically generated immediately to warn the wearer to take appropriate actions. These wearable sleep monitoring systems may be housed in earbud-style or hearing-aid-style structures, suitable for snugly pre-mounted electrodes, easy self-installation or self-removal and nightly use at home.

22 Claims, 22 Drawing Sheets

(56)             References Cited

U.S. PATENT DOCUMENTS

| | | | |
|---|---|---|---|
| 2022/0061767 A1* | 3/2022 | Goldstein | .............. A61B 5/721 |
| 2024/0008800 A1 | 1/2024 | Ahmed et al. | |
| 2024/0189594 A1 | 6/2024 | Hamner et al. | |
| 2024/0198086 A1 | 6/2024 | Simon et al. | |

* cited by examiner

AURICULAR SLEEP MONITORING SYSTEMS AND EAR-CANAL PULSE OXIMETER

CROSS REFERENCE TO RELATED APPLICATIONS

This application claims priority to and the benefit of the filing date of U.S. Provisional Application No. 63/834,109 filed on Feb. 21, 2025, entitled "Auricular Sleep Monitoring System with Auricular EOG (Electro-oculogram) and Auricular EEG (Electroencephalogram)", which is hereby incorporated by reference in its entirety.

FIELD OF THE INVENTION

This patent specification relates to the field of wearable health monitoring systems and devices. More specifically, this patent specification relates to a novel wearable health monitoring system that may include auricular electrooculogram (EOG), auricular electroencephalogram (EEG) auricular electrocardiogram (ECG) and ear-canal pulse oximeter which may be used in at-home sleep monitoring systems, health monitoring systems and hybrid brain-computer interface system.

BACKGROUND

There are many types of wearable health tracking devices available, including various smart watches and health trackers. Several health conditions can be monitored or recorded by these devices, including blood oxygen, heart rate, respiratory rate, sleep, exercise, steps count, electrocardiogram (ECG) and blood pressure etc. However, none of the conventional smart watches or health trackers can do electroencephalogram (EEG) to monitor the brain activities or electrooculogram (EOG) to monitor extra-ocular movements.

The human external ear is a commonly disregarded location for health monitoring. The ear is very close to the brain and recent studies have shown that electrodes placed in the external ear canal can do electroencephalogram (EEG). Traditional EEG is done with multiple (mostly 21) electrodes and wires being attached to the scalp. It is bulky, ugly, cumbersome and very difficult for wearer to move around. In traditional EEG, the electrodes are attached or glued to the scalp. Traditional EEG is usually for short-term use only (half an hour to a couple days) because the electrodes often become detached after a short time. Thus, there exists a great need to have a miniature nice-looking device which can monitor EEG on a long-term (weeks, months, or years) basis. Traditionally, EEG has been used primarily in the medical or biomedical research fields. Nowadays, in the artificial intelligence and robotics era, EEG or modified EEG is also heavily used in the brain-computer interface (BCI). Advancement in electronics technology, miniaturization trend, and dry electrode technology, together with sophisticated EEG interpretation algorithms, have enormously widened the potential usefulness of EEG in various medical fields.

In recent years, wireless in-ear EEG have been reported. For example, as published on Aug. 2, 2024, in Nature Communications, Ryan Kaveh et. al. reported using wireless miniature dry ear electrodes for in-ear EEG, with wireless electronics and offline classification algorithms, to monitor drowsiness of pilots and drivers. They described the design of earpieces for EEG, the neural recording hardware, the electrode materials and multi-sensor array. The recorded EEG data are digitized and transmitted to a processing unit for offline processing. They also describe manufacturing methods for in-ear EEG sensors. Two contralaterally worn earpieces can provide up to 11 channels with a common reference. Either right or left cymba concha electrode can be used as a reference. Prior to this report, earpieces with wet (hydrogel coated) electrodes were often used for EEG. These in-ear EEGs have been shown to successfully monitor drowsiness, seizure and sleep etc. Wireless dry EEG electrodes are also available from Zeto, Inc. (Santa Clara, California) with its WR EEG system.

Various EEG algorithms for decoding and processing of EEG data have been developed and described in many studies and they can accurately detect seizures, migraine, cluster headache, depression, bipolar disorder and other neuropsychiatric disorders. The EEG data can also help prediction of impending seizures, migraine, cluster headaches, depression, bipolar disorder and other neurological or psychiatric conditions. Artificial intelligence, including machine learning (ML) and deep learning (DL) algorithms were applied to EEG data for processing. Several different methods with very high accuracy for seizure detection were described by Maham Saeidi, et al, in a published article in Brain Science on Nov. 18, 2021.

The conventional smart watches and health trackers can track sleep and assess duration of various sleep stages. There are many types of sleep trackers. Some of them are wearable and can be strapped at the wrist. Other types of sleep trackers can be clipped on the pillow or put on bedside table. However, these conventional sleep trackers do not measure sleep directly. They usually use motion sensors to detect inactivity and use inactivity as a surrogate for estimating sleep. Thus, most of the conventional sleep trackers are not accurate. For example, Apple watch Series 9 can monitor sleep and divide it into 4 sleep stages: Awake, Rapid eye movement (REM) sleep, Core sleep and Deep sleep. These sleep stages were "guessed" by monitoring the person's activity, heart rate, breathing, movement, blood oxygen etc. The most accurate sleep monitoring should include electroencephalogram (EEG) and electrooculogram (EOG). (EOG to record extra-ocular eye movements in order to classify REM sleep.) Since these conventional smart watches and health trackers do not have EEG and EOG, their sleep monitoring results are not very precise.

The most reliable sleep assessment is by polysomnography (PSG) which is the gold standard for diagnosing and treating sleep disorders and sleep apnea. PSG uses EEG and EOG and various other sensors to accurately classify sleep stages and the detail of sleep architecture. The sleep stages, as detected by PSG, include the following:

Alert-wakefulness: EEG showing low-amplitude mixed frequency;

Drowsy-wakefulness: EEG showing alpha waves with 8 to 13 Hz;

NREM sleep stage N1: EEG showing mixed alpha waves (8-13 Hz) and theta waves (4-7 Hz), mild decrease of heart rate, respiration, blood pressure and body temperature;

NREM sleep stage N2: EEG showing 11 to 16 Hz sleep spindles (bursts) and 0.5 to 2 Hz K-complexes (biphasic waves), EEG also shows theta waves (4-7 Hz), minimal or no eye movement, more decrease in heart rate, respiration, blood pressure and body temperature;

NREM sleep stage N3: also called slow wave sleep, EEG showing large and slow waves 0.5 to 3 Hz (Delta waves), further decrease in heart rate, respiration, blood pressure and body temperature; and REM sleep (stage R): EEG showing prominent theta waves or low amplitude mixed frequencies resembling wakefulness and EOG showing rapid eye movements.

Normally, during a night sleep there are several cycles of stages that oscillate between the non-rapid eye movement (NREM) stages and rapid eye movement (REM) stage. With the help of EEG analysis algorithms, these NREM sleep stages can be easily detected with EEG. (REM sleep stage needs EOG to confirm.)

In recent years, the importance of REM stage sleep is increasingly being recognized because it was found to be associated with various neurological, psychological, physiological and pathological phenomena, including early detection of Alzheimer's disease. Besides Alzheimer's disease, REM sleep latency changes or duration or density changes have also been reported in bipolar disorder, schizophrenia, parasomnia and other neuropsychiatric conditions.

Sleep disorders and sleep apnea affects millions of Americans. Polysomnogram (PSA) is the gold standard for accurate diagnosis and detection of sleep disorders and sleep apnea, including obstructive sleep apnea (OSA) and central sleep apnea (CSA). However, conventional polysomnogram (PSG) for sleep study is very expensive, time-consuming, requiring overnight stay in sleep centers or other medical facilities which are often not readily available.

The electrooculogram (EOG) is an essential component for polysomnogram (PSG). The EOG is the recording of the retina-cornea potentials generated by extra-ocular movements of eyes. More specifically, the EOG can record extra-ocular movements by measuring the electrical potential differences between the cornea and retina. As the eyeball moves, the orientation of corneo-retinal potential changes and this can be measured by the EOG electrodes. There are two electrodes for the conventional EOG, one electrode being placed 1 cm above the outer canthus of the right eye and the other electrode being placed 1 cm below the outer canthus of the left eye. These two electrodes can record the movement of the eyes by picking up the electro-potential difference between the cornea and the retina (the cornea is positively charged relative to the retina). The EOG can greatly improve the accuracy in determining REM sleep since rapid eye movements are characteristic during REM sleep.

Traditionally, EOG is used in medical field, especially in ophthalmology and neuro-psychiatry. EOG is also used in sleep study. With technological advancements, more sophisticated EOG systems have been developed and used in artificial intelligence and in robotics. EOG has been used in fields like assisted mobility and in systems to control automatic robotic mobility. It is also used in electric wheelchair control and in graphic-human interface. EOG can also supplement EEG in brain-computer interface (EEG-EOG BCI) (or hybrid BCI). EOG is done by placing a pair of electrodes either above and below the eyes or to the right and left of the eyes. The human eye is an electric dipole with the positive pole at the front of the eye (cornea), and the negative pole at the back of the eye (retina). Extra-ocular movements of the eyes will produce potential differences between the pair of electrodes. The EOG amplitude and sensitivity can vary, depending on the EOG electrodes placement. For the conventional EOG electrodes placement, the EOG amplitudes may range from 50 to 3500 microvolts in human. The sensitivity of EOG recording to eyeball movements can be in the range of 10 to 30 microvolts per degree of saccadic eye movement (rapid eye movement.) An amplifier is used to augment the EOG potential while a filter is used to filter out other biopotentials (like biopotentials from the brain or from muscles).

Besides EEG for brain activity and EOG for extra-ocular movements of eyes, the PSG also include sensors or monitors for other body functions, including EMG, ECG, pulse oximeter, body temperature, airflow sensor, peripheral arterial tonometer (PAT), actigraphy, leg movement sensor, body position sensor and respiratory inductance plethysmography (RIP), etc. These sensors enable the PSG to assess detailed sleep profile and also to detect sleep disorders and sleep apnea (including obstructive sleep apnea and central sleep apnea), with the help of sophisticated sleep analysis algorithms.

Most conventional at-home sleep monitoring systems do not have EEG and EOG. They use various ancillary sleep-relevant sensors as surrogate to assess sleep stages. They also use various sleep-relevant sensors to enable detection of sleep apnea. These sleep-relevant sensors include pulse oximeter, peripheral arterial tonometer (PAT), airflow sensor (airflow meter), actigraphy or motion sensor, leg movement sensor, body position sensor and respiratory inductance plethysmography (RIP).

Pulse oximeter has been widely used to estimate the percentage of oxygen bound to the blood hemoglobin. Because oxygenated and deoxygenated hemoglobin have difference in their absorption of light from different wavelengths. The pulse oximeter uses light-emitting diodes to produce lights of different wavelengths. The pulse oximeter then uses light-sensitive sensor to measure the absorption of red and infrared wavelengths to estimate the oxygen saturation from the absorption spectrum. There are two types of pulse oximeters. In transmittance (transmissive-mode) pulse oximeter, the light generator and the light detector (or sensor) are located at opposite sides of the tissue (such as fingertip or earlobe). The amount of oxygen in the blood determines how much light is absorbed after the light passes through the body part. Transmittance pulse oximeter is the most common type of pulse oximeter. In reflectance (reflective-mode) pulse oximeter, the light generator and light detector are located on the same side of the tissue (such as forehead or wrist). Reflectance pulse oximeters are placed on the skin surface and measure the light reflected off the tissues rather than through the tissue. Both types of pulse oximeters can help in sleep apnea detection because during sleep apnea, the blood oxygen saturation decreases.

Peripheral arterial tonometer (PAT) is another device useful for assessing respiration. It involves applying a certain pressure to a part of the body (for example a finger or forearm) and using optical sensors to measure the pulsatile volume changes in the vascular bed. Respiratory events could produce vasoconstriction which will decrease the PAT signal amplitude. When decrease of PAT amplitude, together with increase in heart rate and body activity, can help to score apnea and hypopnea events. Sleep disordered breathing is often associated with arousal during sleep. The arousals can cause autonomic activation which is associated with sympathetic nervous system-mediated peripheral vasoconstriction and transient pulse rate increase. These can be detected by PAT to help assessment of respiration and apnea.

Airflow sensor (or airflow meter or nasal pressure sensor) is often used in sleep studies to monitor the airflow of breathing. Various technologies, such as pressure transducers and polyvinylidene fluoride (PVDF), are used in airflow sensors to detect inhalation and exhalation and to monitor breathing during sleep. Airflow sensor, together with RIP, are very valuable in assessment of sleep apnea.

Actigraphy (or motion sensor) is a wearable device that can track movement and help to estimate sleep. Besides the traditional triaxial accelerometers, the actigraphy may incorporate other sensors such as photoplethysmography (PPG). Actigraphy can be worn on the wrist or finger or arm or even chest and can provide monitoring of activity and sleep. Actigraphy can detect movement to help determine whether the wearer is awake or asleep.

Respiratory inductance plethysmography (RIP) is very useful for evaluation of respiration by measuring movements and pressure change of the chest wall and the abdominal wall. Transducers are placed at the chest and the abdomen to detect changes in inductance or resistance to change in flow of the transducers. RIP can detect changes in the chest and abdominal volumes during inspiration and expiration. The RIP signals can provide estimate of the respiratory pattern and the tidal volume during sleep. RIP has been successfully used in various sleep monitoring systems.

There are three types of sleep apnea: obstructive sleep apnea (OSA), central sleep apnea (CSA) and mixed (or complex) sleep apnea (mixed OSA and CSA). In OSA, the airflow stopped while the respiratory effort is present. In CSA, the respiratory effort is absent and airflow is also absent. Although pulse oximeter and PAT do not directly measure airflow or respiratory effort, they are very helpful in sleep apnea assessment. Pulse oximeter measures blood oxygen saturation and significant decrease of blood oxygen saturation can be used as a surrogate for apnea detection. PAT can assess vasoconstriction and can help detect apnea since apnea is usually accompanied by vasoconstriction. Using PAT, together with heart rate and body activity, can be used as surrogate for sleep apnea detection. Obstructive sleep apnea (OSA) is a very important sleep problem, affecting millions of people in USA. OSA consists of cessation of airflow despite normal respiratory effort. It is caused by partial or complete obstruction of the upper airway. Polysomnography can detect and diagnose OSA and CSA. It has been found that REM sleep correlates with the severity of sleep apnea due to the difference in sleep positions between REM and NREM sleep. Apneic episodes are more prevalent during REM sleep.

Polysomnography (PSG) is the gold standard for traditional sleep study for assessment of sleep profile, and for diagnosis of sleep disorders and sleep apneas. PSG can help to differentiate obstructive sleep apnea versus central sleep apnea. PSG is performed overnight in a sleep center or a medical facility with the patient continuously monitored by a certified technologist. The PSG includes EEG and EOG. PSG usually also include various other monitors or sensors, including pulse oximeter, peripheral arterial tonometry (PAT), airflow meter (or nasal airflow sensor), actigraphy (or motion sensor), respiratory inductance plethysmography (RIP), ECG and leg movement sensor. Other sensors or monitors, like EMG, body temperature sensor and body position sensor may also be included. With sophisticated sleep analysis algorithms, the PSG can assess detailed sleep profile, including sleep architecture, sleep stages, sleep latency, sleep density, duration of each sleep stage, sleep quality, presence of obstructive sleep apnea (OSA) and presence of central sleep apnea (CSA). With the help of sophisticated sleep analysis algorithms, the PSG can also detect various sleep disorders include narcolepsy, restless leg syndrome, periodic limb movement disorder, REM sleep behavior disorder, parasomnias and insomnia. For sleep apnea, PSG can help to differentiate obstructive sleep apnea vs central sleep apnea vs mixed (or complex) sleep apnea.

Although polysomnogram (PSG) has been widely recognized as gold standard for sleep study and sleep monitoring, PSG does have significant drawbacks, including very expensive, cumbersome, requiring overnight stay in a sleep center or a medical facility. PSG is not readily available in many parts of the country. Insurance companies are often reluctant to pay for the PSG studies. The other problem is that sleeping at a sleep center or a medical facility is not the same as sleeping on patient's own bed at home. Because of these drawbacks, various at-home sleep studies have been developed. Various sensors are used in various at-home sleep studies, for example: pulse oximeter, airflow meter (nasal pressure sensor), respiratory inductance plethysmography, peripheral arterial tonometer (PAT), actigraphy (actimetry sensor with accelerometer) and leg movement sensor. Body temperature sensor, ECG, blood pressure measurement and body position sensor may be included as well.

In sleep apnea evaluation and diagnosis, it is important to score the patient's Apnea-Hypopnea Index (AHI) score. By a commonly accepted definition, an apnea event is when the patient stops breathing or has reduced breathing to about 10% for 10 seconds or longer. A hypopnea event is when the patient constricts breathing by over 30% for 10 seconds or longer. The AHI score is the average number of times of these two events per hour of sleep. For adults, less than 5 events per hour is normal; for children, less than one event per hour is normal. For adults, the severity of sleep apnea is classified by the following AHI scores: Mild: 5 to 14, Moderate: 15 to 29, Severe: 30 or more. With availability of EEG, polysomnogram can assess the accurate sleep time and thus can arrive at accurate AHI scores. Most conventional at-home sleep studies do not have EEG and usually use total recorded time or inactivity time, rather than actual sleep time, to calculate the AHI score. Because of this, most conventional at-home sleep studies often underestimate the severity of sleep apnea. Alternatively, other index, like Respiratory Disturbance Index (RDI) may be used.

There is a trade-off regarding how many sensors to be used in an at-home sleep study. Using more sensors could improve the accuracy of the sleep study and provide more detail of the sleep profile. However, more sensors might make it more cumbersome for people to use at home and also increase the risk of sensors falling off or being dislodged during sleep. More sensors might also interfere with user's sleep. The conventional at-home sleep studies usually do not include EEG and EOG and thus they cannot measure sleep duration directly. They use various other parameters (such as inactivity, pulse rate, oxygen level, body temperature etc.) as surrogates to "guess" wearer's sleep. The sleep apnea study needs to gather the data of how many apnea and hypopnea events during the sleep time. These conventional at-home studies can provide only how many apnea and hypopnea events during the study time, rather than during sleep time. Because of these problems, these conventional at-home sleep studies are not very accurate.

Therefore, a need exists for novel wearable sleep monitoring systems and devices which do not suffer from the above-mentioned drawbacks of existing systems and devices. A need also exists for novel sleep monitoring systems that are more accurate, more convenient, less disruptive for sleep and can allow easy self-instillation or self-removal and daily at-home use.

BRIEF SUMMARY OF THE INVENTION

Novel Auricular Sleep Monitoring Systems and Ear-Canal Pulse Oximeter are provided.

In some embodiments, a concise sleep monitoring system with auricular electroencephalogram (EEG) may be configured as a novel sleep monitoring system. Preferably, a concise sleep monitoring system may include an auricular electroencephalogram (EEG) monitoring system, an ancillary sleep surveillance system, and a processing unit. The auricular electroencephalogram (EEG) monitoring system may have a first EEG recording module that may be in wired or wireless electronic communication with a first set of a plurality of wired or wireless EEG electrodes. All of the first set EEG electrodes are configured to be coupled to a wearer's first ear or a peri-auricular area around the wearer's first ear, and the first EEG recording module may be in electronic communication with all of the first set EEG electrodes. When the first set EEG electrodes are coupled to the wearer's first ear or the peri-auricular area around the wearer's first ear all of the first set EEG electrodes are positioned in contact with separate locations on an area of the wearer, in which the area may be at least one of the following: external ear of the wearer's first ear, external canal of the wearer's first ear, and the peri-auricular area around the wearer's first ear. The EEG recording module may be configured to record EEG data of the wearer via the first set EEG electrodes. The ancillary sleep surveillance system may include at least one of the following sensors or monitors: a pulse oximeter, a peripheral arterial tonometry (PAT) monitor, an airflow sensor, an actigraphy sensor, a leg movement sensor, a respiratory inductance plethysmograph (RIP) monitor, a body temperature sensor, an electromyogram (EMG) sensor, an electrocardiogram (ECG) sensor, a body position sensor, and a blood pressure sensor. The pulse oximeter may be configured to record pulse data of the wearer and blood oxygen saturation data of the wearer. The PAT monitor may be configured to record breathing disturbances data of the wearer. The airflow sensor may be configured to record nasal airflow data of the wearer. The actigraphy sensor may be configured to record motion data of the wearer. The leg movement sensor may be configured to record leg movement data of the wearer. The RIP monitor may be configured to be coupled to the chest or abdomen of the wearer and may be configured to record respiratory effort data of the chest or abdomen of the wearer. The body temperature sensor may be configured to record the body temperature data of the wearer. The EMG sensor may be configured to record the EMG (usually EMG of the wearer's chin muscle) data of the wearer. The ECG sensor is configured to record the ECG data of the wearer. The body position sensor is configured to record the body position data of the wearer. The blood pressure monitor is configured to record the blood pressure data of the wearer. The processing unit may be in electronic communication with the EEG monitoring system, and the processing unit may be in electronic communication with each incorporated (comprising) sensor or monitor of the ancillary sleep surveillance system. The processing unit may be configured to analyze the EEG data from the EEG monitoring system and the data from the ancillary sleep surveillance system to assess the wearer's sleep profile.

In some embodiments, novel auricular sleep monitoring systems and ear-canal pulse oximeter may be configured as another novel sleep monitoring system. Preferably, a comprehensive sleep monitoring system may include an auricular electrooculogram (EOG) monitoring system, an auricular electroencephalogram (EEG) monitoring system, an ancillary sleep surveillance system, and a processing unit. The auricular EOG system may have an EOG recording module. The EOG recording module includes at least two wired or wireless EOG electrodes in electronic communication with the EOG recording module. The EOG electrodes are configured to be coupled to a wearer's first ear or a peri-auricular area around the wearer's first ear. When the EOG electrodes are coupled to the wearer's first ear or the peri-auricular area around the wearer's first ear all of the EOG electrodes may be positioned in contact with separate locations on an area of the wearer, in which the area may be at least one of the following: external ear of the wearer's first ear, external ear canal of the wearer's first ear, and the peri-auricular area around the wearer's first ear. The EOG recording module may be configured to record EOG data of the wearer via the EOG electrodes. The auricular electroencephalogram (EEG) monitoring system may have a first EEG recording module comprising a first set of a plurality of wired or wireless EEG electrodes. All of the first set EEG electrodes are configured to be coupled to a wearer's first ear or a peri-auricular area around the wearer's first ear, and the first EEG recording module may be in electronic communication with all of the first set EEG electrodes. When the first set EEG electrodes are coupled to the wearer's first ear or the peri-auricular area around the wearer's first ear all of the first set EEG electrodes are positioned in contact with separate locations on an area of the wearer, in which the area may be at least one of the following: external ear of the wearer's first ear, external ear canal of the wearer's first ear, and the peri-auricular area around the wearer's first ear. The EEG recording module may be configured to record EEG data of the wearer via the first set EEG electrodes. The ancillary sleep surveillance system may include at least one of the following sensors or monitors: a pulse oximeter, a peripheral arterial tonometry (PAT) monitor, an airflow sensor, an actigraphy sensor, a leg movement sensor, a respiratory inductance plethysmograph (RIP) monitor, a body temperature sensor, an electromyogram (EMG) sensor, an electrocardiogram (ECG) sensor, a body position sensor, and a blood pressure sensor. The pulse oximeter may be configured to record pulse data of the wearer and blood oxygen saturation data of the wearer. The PAT monitor may be configured to record breathing disturbances data of the wearer. The airflow sensor may be configured to record nasal airflow data of the wearer. The actigraphy sensor may be configured to record motion data of the wearer. The leg movement sensor may be configured to record leg movement data of the wearer. The RIP monitor may be configured to be coupled to the chest or abdomen of the wearer and may be configured to record respiratory effort data of the chest or abdomen of the wearer. The body temperature sensor may be configured to record the body temperature data of the wearer. The EMG sensor may be configured to record the EMG (usually EMG of the wearer's chin muscle) data of the wearer. The ECG sensor is configured to record the ECG data of the wearer. The body position sensor is configured to record the body position data of the wearer. The blood pressure monitor is configured to record the blood pressure data of the wearer. The processing unit may be in electronic communication with the EOG monitoring system, the EEG monitoring system, and the processing unit may be in electronic communication with each incorporated (comprising) sensor or monitor of the ancillary sleep surveillance system. The processing unit may be configured to analyze the EOG data from the EOG monitoring system, the EEG data from the EEG monitoring system, and the data from the ancillary sleep surveillance system to assess the wearer's sleep profile.

In some embodiments, novel auricular sleep monitoring systems and ear-canal pulse oximeter may further include an ear-canal pulse oximeter. Preferably, the ear-canal pulse oximeter may be a reflectance pulse oximeter that may include a wired or wireless light generator having a light-emitting diode configured to emit light of different wavelengths, and the wired or wireless light generator may be configured to be coupled to an external ear canal of a wearer's first ear to be in contact with the skin of the external ear canal of the wearer's first ear. The ear-canal pulse oximeter may also include a wired or wireless light detecting sensor configured to measure the absorption of light of different wavelengths including red and infrared wavelengths, and the wired or wireless light detecting sensor may be configured to be coupled to the external ear canal of a wearer's first ear to be in contact with the skin of the external ear canal of the wearer's first ear. The ear-canal pulse oximeter may also include a reflectance oximeter module having a detection module, and the detection module may be in electronic communication with the wired or wireless light generator and the wired or wireless light detecting sensor. The detection module may be configured to analyze the data transmitted from the wired or wireless light generator and data transmitted from the wired or wireless light detecting sensor to record the wearer's pulse data and blood oxygen saturation data.

In some embodiment, a novel auricular sleep monitoring system may comprise an auricular electroencephalogram (EEG) monitoring system and an ear-canal pulse oximeter. The auricular EEG monitoring system and the ear-canal pulse oximeter are as described hereinbefore. The auricular sleep monitoring system may further comprise a processing unit in electronic communication with the auricular EEG monitoring system and the ear-canal pulse oximeter. The processing unit is configured to analyze the EEG data recorded by the auricular EEG monitoring system to assess the wearer's EEG profile including EEG data for classification of sleep stages (except for REM sleep stage). The processing unit is further configured to process the pulse data and blood oxygen saturation data recorded by the ear-canal pulse oximeter and the processing unit is configured to detect presence of dropping of the oxygen saturation below a predetermined level (for example: below 90%, 88%, 85% or other predetermined level). This novel auricular sleep monitoring system is configured to use the information of significant dropping of blood oxygen saturation as surrogate for sleep apnea detection.

In some embodiments, novel auricular sleep monitoring systems and ear-canal pulse oximeter may further include an auricular electrocardiogram (ECG) system. Preferably, the auricular ECG system may comprise an ECG recording module that may include at least two wired or wireless ECG electrodes in electronic communication with the ECG recording module. All of the ECG electrodes may be configured to be coupled to the wearer's first ear or a peri-auricular area around the wearer's first ear. When the ECG electrodes are coupled to the wearer's first ear or the peri-auricular area around the wearer's first ear all of the ECG electrodes are positioned in contact with separate locations on an area of the wearer, in which the area may be at least one of the following: external ear of the wearer's first ear, external ear canal of the wearer's first ear, and the peri-auricular area around the wearer's first ear. The ECG recording module may be configured to record ECG data of the wearer via the ECG electrodes. Optionally, the auricular ECG system may replace the conventional ECG sensor from the ancillary sleep-surveillance system since the auricular ECG system is easier and more convenient for the wearer to use.

In some embodiments, novel auricular sleep monitoring systems and ear-canal pulse oximeter may include an auricular electroencephalogram (EEG) monitoring system having two sets of EEG recording modules (including a first EEG recording module and a second EEG recording module). The auricular EEG monitoring system may include a first EEG recording module and a processing unit. The first EEG recording module may include or may be in communication with a first set of a plurality of wired or wireless EEG electrodes, and each first set EEG electrode may be configured to be coupled to a wearer's first ear or a peri-auricular area around the wearer's first ear. The first EEG recording module may be in electronic communication with each first set EEG electrode, and when the first set of a plurality of EEG electrodes are coupled to the wearer's first ear or the peri-auricular area around the wearer's first ear, the first set EEG electrodes may be positioned in contact with separate locations on an area of the wearer. The area may include at least one of the following: the external ear of the wearer's first ear, the external ear canal of the wearer's first ear, and the peri-auricular area around the wearer's first ear, and the first EEG recording module may be configured to record EEG data of the wearer via the first set of a plurality of EEG electrodes. The processing unit may be in electronic communication with the first EEG recording module, and the processing unit may be configured to analyze the EEG data transmitted from the first EEG recording module to obtain the electroencephalographic profile of a wearer. Optionally, the auricular EEG monitoring system may include a second EEG recording module in electronic communication with a second set of a plurality of wired or wireless (preferably wireless) EEG electrodes and the processing unit. Each EEG electrode of the second set of a plurality of EEG electrodes may be configured to be coupled to the second ear of the wearer and the peri-auricular area around the wearer's second ear. The second EEG recording module may be in electronic communication with each second set EEG electrode, and when the second set of a plurality of EEG electrodes are coupled to the wearer's second ear or the peri-auricular area around the wearer's second ear, the second set EEG electrodes may be positioned in contact with separate locations on an area of the wearer. The area may include at least one of the following: the external ear of the wearer's second ear, the external ear canal of the wearer's second ear, and the peri-auricular area around the wearer's second ear, and the second EEG recording module may be configured to record EEG data of the wearer via the second set of a plurality of EEG electrodes. The processing unit may be in electronic communication with both the first and the second EEG recording modules and the processing unit may be configured to analyze the EEG data transmitted from the first and the second EEG recording modules to obtain the EEG profile from both sides of the brain of the wearer.

In some embodiments, novel auricular sleep monitoring systems and ear-canal pulse oximeter may include a housing structure that is suitable to be inserted into the wearer's external ear canal. Preferably, the housing structure may be selected from one of the following: an earbud-style structure, an in-the-ear portion of a behind-the-ear-hearing-aid-style structure and a tubular-shaped structure. Preferably, the EEG electrodes, EOG electrodes (if EOG is incorporated), ECG electrodes (if ECG is incorporated), the light generator and light detecting sensor of the ear-canal pulse oximeter (if ear-canal pulse oximeter is incorporated) are configured to be pre-mounted and located (partially embedded and integrated with slight protrusion at the surface) on the surface of the housing structure. The housing structure may comprise a flexible elastic and adaptable material (e.g. soft foam or very soft silicone-type material) and the flexible elastic and adaptable material is configured to have appropriate flexibility, elasticity and adaptability such that it will naturally adapt to the contour of the wearer's external ear canal and snugly fill the interior of the wearer's external ear canal when the housing structure is inserted into the wearer's external ear canal and so that all of the EEG electrodes, EOG electrodes (if EOG is incorporated), ECG electrodes (if ECG is incorporated), the light generator and light detecting sensor (if ear-canal pulse oximeter is incorporated) are naturally and snugly in contact with the skin of the wearer's external ear canal when the housing structure is inserted into the wearer's external ear canal. Installing and removing these EEG electrodes, EOG electrodes (if EOG is incorporated), ECG electrodes (if ECG is incorporated), the light generator and light detecting sensor (if ear-canal pulse oximeter is incorporated) will be as easy as inserting and removing the housing structure from the wearer's external ear canal. Being snugly filled inside the external ear canal will help to decrease movement interference (artifacts) during the EEG, EOG, ECG and ear-canal pulse oximeter recording and allow ambulatory use. The easy self-installation and self-removal designs will be very convenient for user to use repeatedly at home.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION OF THE INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, may be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims may be read with the understanding that such combinations are entirely within the scope of the invention and the claims.

Figure 16:
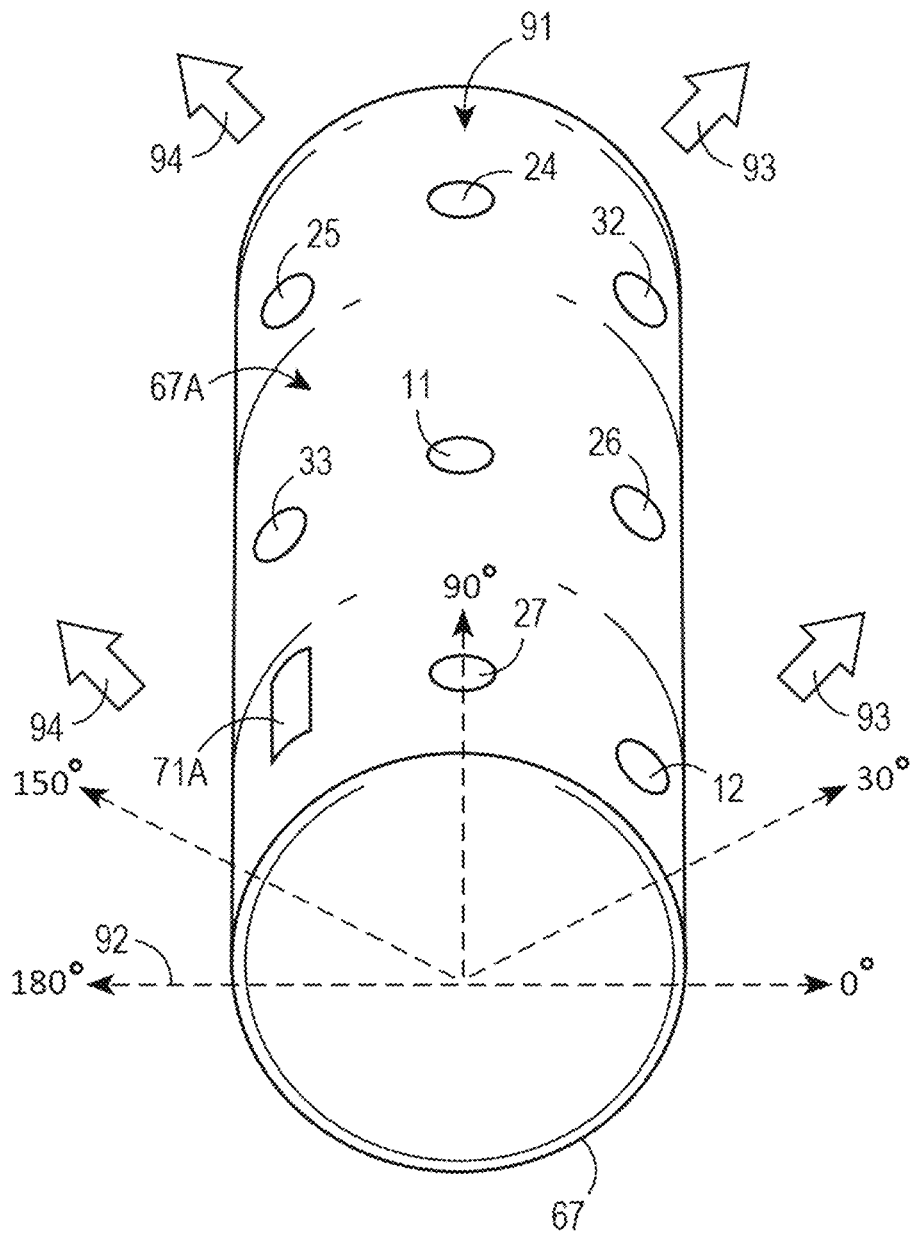
FIG. 16-FIG. 16 depicts a perspective view of a housing structure configured as a tubular-shaped structure having a plurality of electrodes and a wireless ear-canal pulse oximeter according to various embodiments described herein.

For purposes of description herein, the terms "upper", "lower", "left", "right", "rear", "front", "side", "vertical", "horizontal", and derivatives thereof shall relate to the invention as oriented in FIG. 16. However, one will understand that the invention may assume various alternative orientations and step sequences, except where expressly specified to the contrary. Therefore, the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless claims expressly state otherwise.

The term "client device" as used herein is a type of computer or computing device comprising circuitry and configured to generally perform functions such as recording audio, photos, and videos; displaying or reproducing audio, photos, and videos; storing, retrieving, or manipulation of electronic data; providing electrical communications and network connectivity; or any other similar function. Non-limiting examples of client devices include: personal computers (PCs), workstations, servers, laptops, tablet PCs including the iPad, cell phones including iOS phones made by Apple Inc., Android OS phones, Microsoft OS phones, Blackberry phones, Apple iPads, Anota digital pens, smart watches (e.g., Apple Watch, Samsung Galaxy Watch, etc.), digital music players, or any electronic device capable of running computer software and displaying information to a user, memory cards, other memory storage devices, digital cameras, external battery packs, external charging devices, and the like. Certain types of electronic devices which are portable and easily carried by a person from one location to another may sometimes be referred to as a "portable electronic device" or "portable device". Some non-limiting examples of portable devices include: cell phones, smartphones, tablet computers, laptop computers, tablets, digital pens, wearable computers such as Apple Watch, other smartwatches, Fitbit, other wearable fitness trackers, Google Glasses, and the like.

As used herein the term "data network" or "network" shall mean an infrastructure capable of connecting two or more computers such as client devices either using wires or wirelessly allowing them to transmit and receive data. Non-limiting examples of data networks may include the internet or wireless networks or (i.e., a "wireless network") which may include BLE (Bluetooth), LoRa and LoRaWAN (and other low-power, wide-area (LPWA) networking protocols), Wi-Fi, and cellular networks. For example, a network may include a local area network (LAN), a wide area network (WAN) (e.g., the Internet), a mobile relay network, a metropolitan area network (MAN), an ad hoc network, a telephone network (e.g., a Public Switched Telephone Network (PSTN)), a cellular network, a Zigbee network, or a voice-over-IP (VoIP) network.

Although the terms "first", "second", etc. are used herein to describe various elements, these elements may not be limited by these terms. These terms are only used to distinguish one element from another element. For example, the first element may be designated as the second element, and the second element may be likewise designated as the first element without departing from the scope of the invention.

As used in this application, the term "about" or "approximately" refers to a range of values within plus or minus 15% of the specified number. Additionally, as used in this application, the term "substantially" means that the actual value is within about 10% of the actual desired value, particularly within about 5% of the actual desired value and especially within about 1% of the actual desired value of any variable, element or limit set forth herein.

Novel Auricular Sleep Monitoring Systems and Ear-Canal Pulse Oximeter are discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

Figure 1:
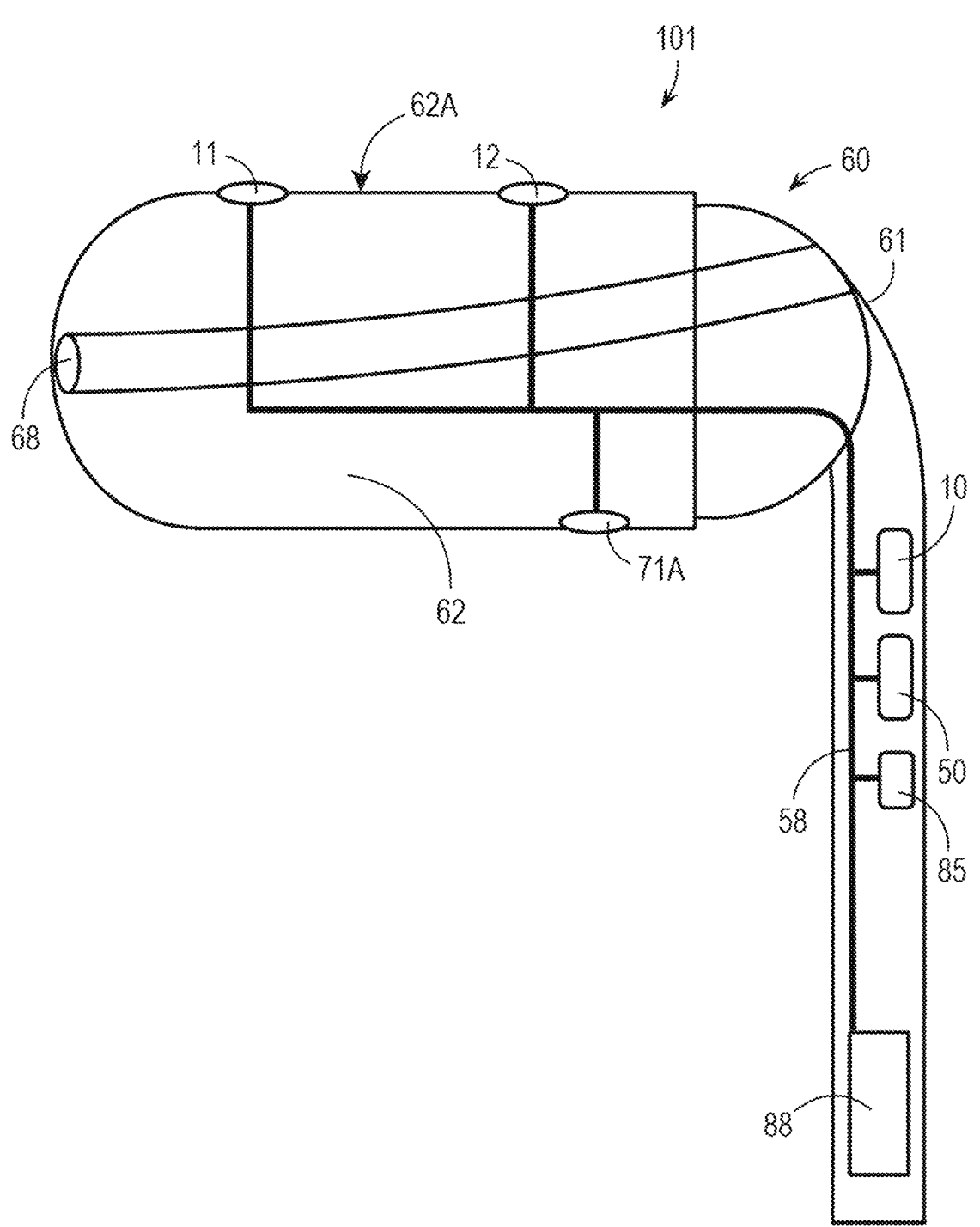
FIG. 1-FIG. 1 depicts a schematic diagram of an example of an auricular electrooculogram (EOG) system according to various embodiments described herein.
Figure 2:
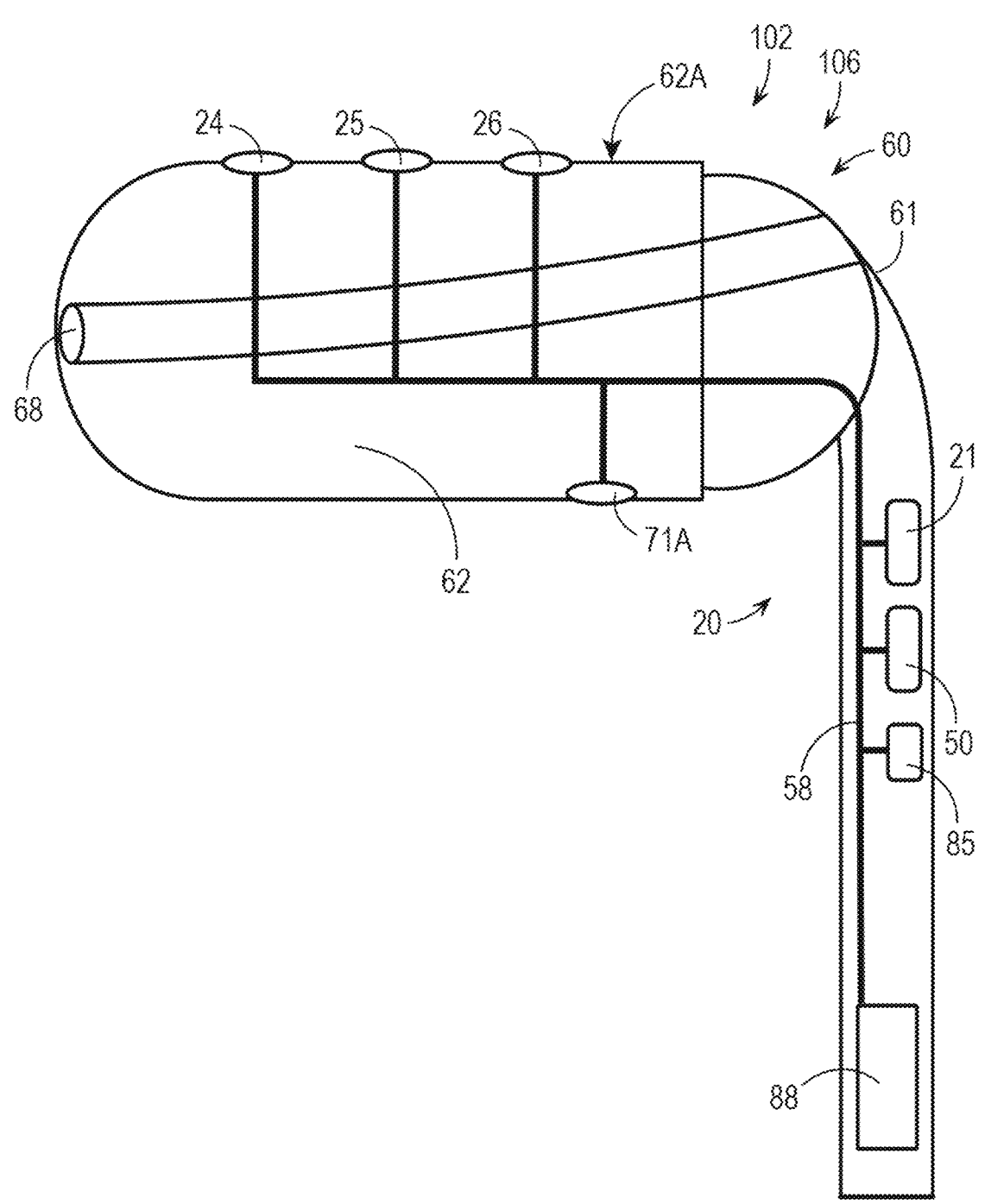
FIG. 2-FIG. 2 illustrates a schematic diagram of examples of an auricular sleep monitoring system and a concise sleep monitoring system according to various embodiments described herein.
Figure 3:
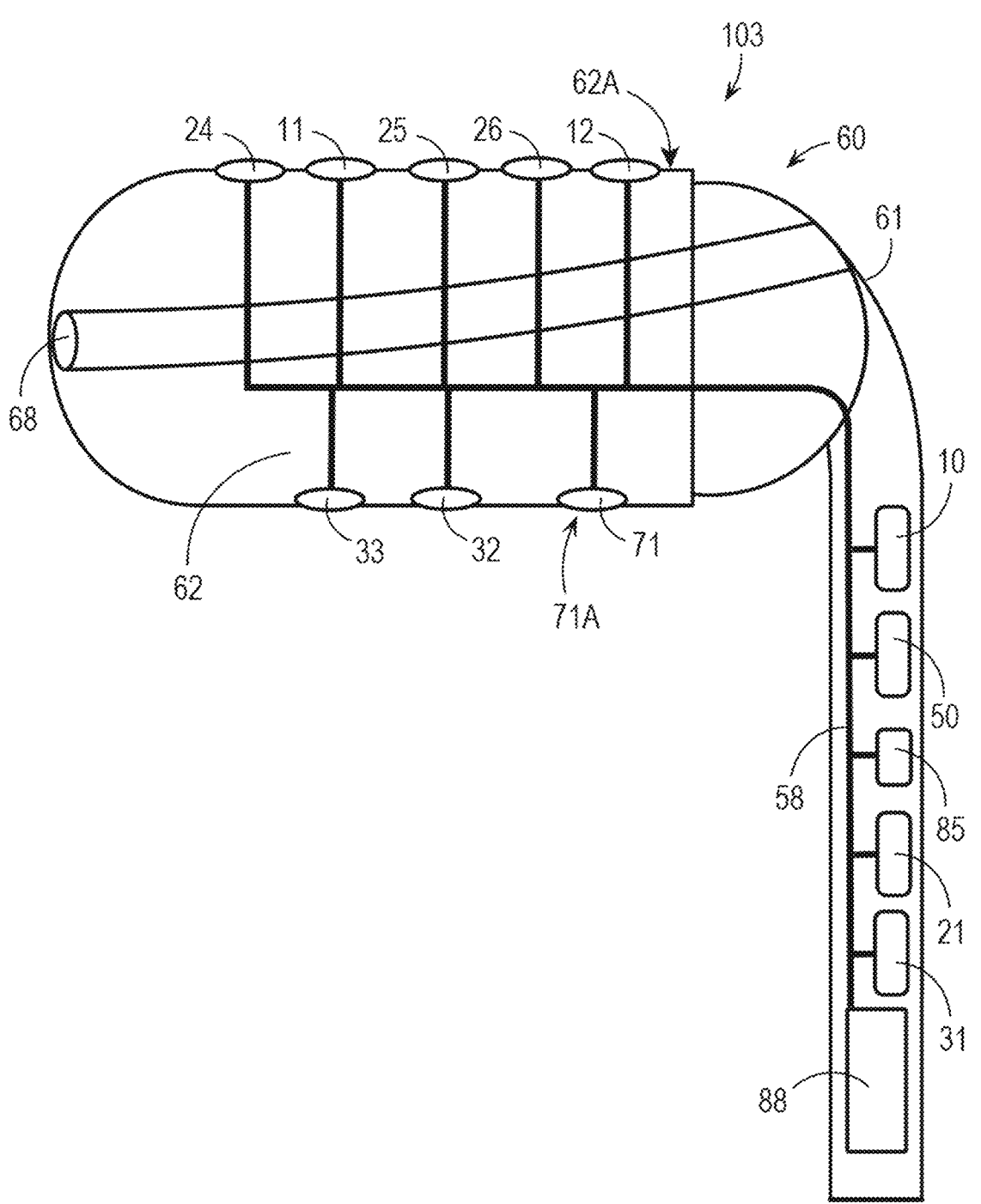
FIG. 3-FIG. 3 shows a schematic diagram of an example of a comprehensive sleep monitoring system according to various embodiments described herein.
Figure 4:
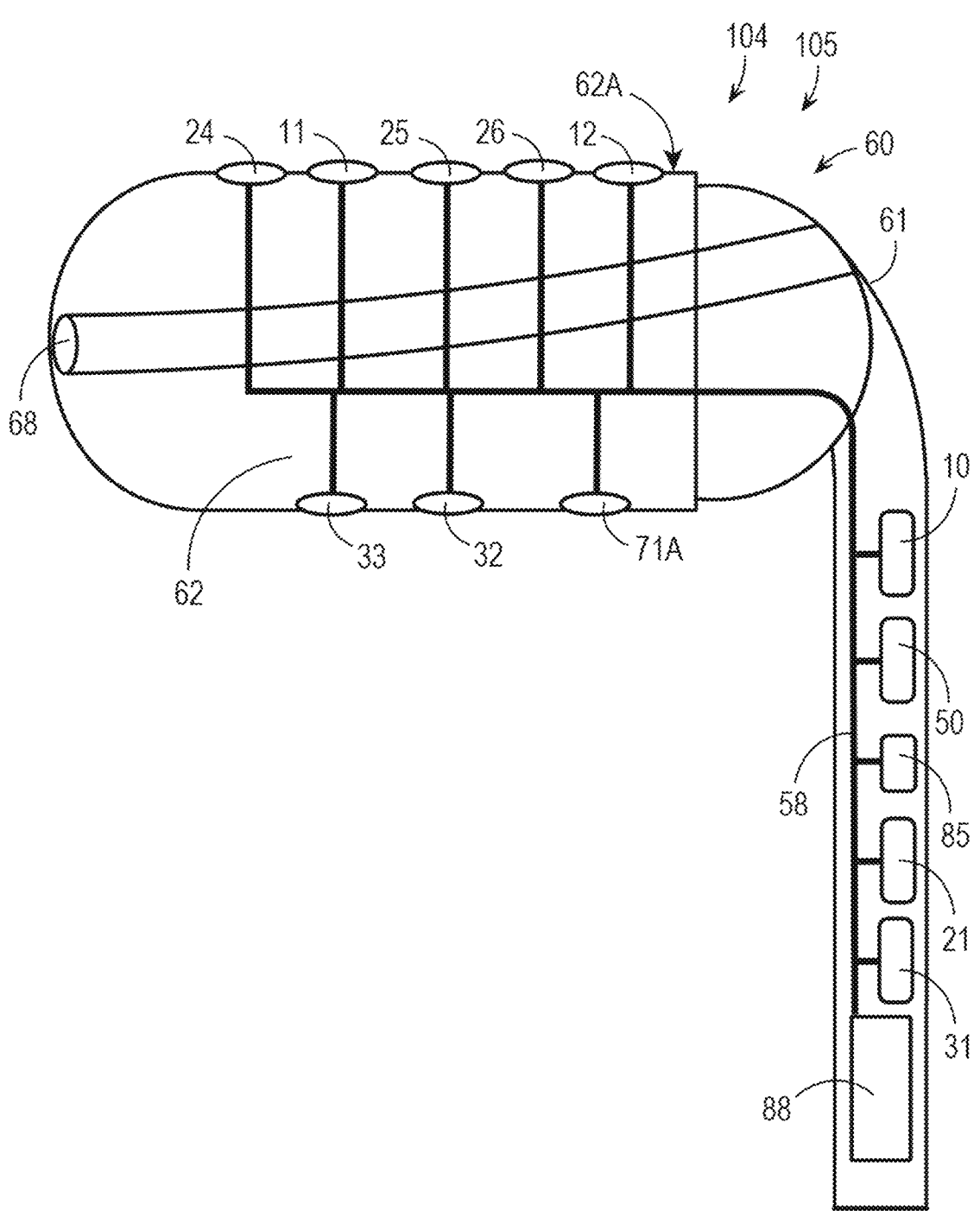
FIG. 4-FIG. 4 depicts a schematic diagram of an example of an auricular health monitoring system and an auricular hybrid brain-computer interface system according to various embodiments described herein.

The present invention will now be described by example and through referencing the appended figures representing preferred and alternative embodiments. FIGS. 2-3 illustrate examples of Sleep Monitoring Systems with Auricular Electroencephalogram (EEG) and Electrooculogram (EOG) and their components according to various embodiments. In some embodiments, as illustrated by FIGS. 1-4, the present invention may comprise one or more of an auricular electrooculogram (EOG) system 101, a concise sleep monitoring system 102 (sometimes called "concise at-home sleep monitoring system 102"), a comprehensive sleep monitoring system 103 (sometimes called "comprehensive at-home sleep monitoring system 103"), an auricular health monitoring system 104, and an auricular hybrid brain-computer interface system 105. In further embodiments, the present invention includes a novel ear-canal pulse oximeter 71A, a novel auricular electrooculogram (EOG) system 101, an auricular electroencephalogram (EEG) monitoring system 20, and an auricular electrocardiogram (ECG) system and utilizing the ear-canal pulse oximeter 71A, auricular EOG system 101, auricular EEG monitoring system 20 and auricular ECG system in novel at-home sleep monitoring systems and novel health monitoring systems.

Traditional EEG systems are quite bulky and cumbersome. Traditional EEG is done with multiple (mostly 21) electrodes and wires being attached to the scalp. Installing traditional EEG electrodes is a tedious job, requiring preparation of the scalp, applying conductive paste or gel, attaching multiple electrodes to exact locations and securing the electrodes with tape or cap. A certified technician is required for installation of the EEG electrodes. With the advancement of technology, including miniaturization trend and dry electrodes technology, wireless wearable in-ear EEG has been developed in recent years.

REM (rapid eye movement) sleep is a very important stage of sleep. Electrooculogram (EOG) is needed for accurate REM sleep monitoring. The traditional EOG includes two electrodes, one being placed one centimeter (cm) above the outer canthus of the right eye and the other one being placed one cm below the outer canthus of the left eye. A certified technician is also required for the installation of the EOG electrodes. These two electrodes pick up the movements of the eyes in virtue of the electro-potential difference between the cornea and the retina.

In some embodiments, the present invention preferably includes a novel auricular electrooculogram (EOG) system 101 that may comprise an EOG recording module 10 that may be in wired or wireless electronic communication 19 with at least two wired or wireless EOG electrodes 11, 12. The EOG electrodes 11, 12 may be coupled to an ear 902 or the peri-auricular area 903 around the ear 902. When the EOG electrodes 11, 12 are coupled to an ear 902 or the peri-auricular area 903 around the ear 902, the EOG electrodes 11, 12 are positioned in contact with separate locations on an area of the wearer 900, the area selected from at least one of the following: the external ear (i.e., the pinna) of a wearer's ear 902, external ear canal 904 of the wearer's ear, and the peri-auricular area 903 around the wearer's ear. The EOG electrodes 11, 12, may be in electronic communication 19 (e.g., wired or wireless communication) with the EOG recording module 10 which is configured to detect the electro-potential differences between the cornea and the retina of the wearer's eye and detect the extra-ocular eye movement data of the wearer 900. As used herein, electronic communication 19 may comprise wired electronic communication, such as provided by a local interface 58, 406, and wireless electronic communication, such as WiFi, Bluetooth, and other wireless electronic communication protocols. EOG recording module 10 may be in electronic communication with a processing unit 50, 401. The EOG recording module 10 may be configured to record, analyze, and/or collect EOG data of the wearer 900 via the EOG electrodes 11, 12, which can be used to detect, access, determine, etc., the extra-ocular movements of the wearer's eyes, such as detecting rapid-eye-movement (REM) sleep stage. The EOG data are also useful in ophthalmological and neuropsychiatric evaluations. The EOG data (together with EEG data) may also be used in hybrid brain-computer interface (BCI).

The peri-auricular area 903 refers to a portion of the head around the auricle (pinna) and this portion of the head 901 is typically hairless. The peri-auricular area 903 includes a portion of the head in front of the auricle (pre-auricular area) and a portion of the head 901 above and behind the auricle (post-auricular area). The pre-auricular area is small, about one inch wide and two inches long and curved along the anterior edge of the auricle. The post-auricular area is also small, about one inch wide and about three inches long and curved along the superior and posterior edges of the auricle (pinna). The post-auricular area is where a behind-the-ear hearing aid is usually located. The small pre-auricular area and post-auricular area together will be called "peri-auricle area" 903 hereinafter. (Anterior, posterior, superior, in front of and behind etc. all refer to the directions relative to the wearer's head 901 when the wearer 900 is in an upright position.) As referred to herein, the external ear canal 904 refers to the part of the ear 902 that connects the visible outer ear (pinna) to the middle ear, essentially the tube that carries sound waves to the eardrum.

Figure 9:
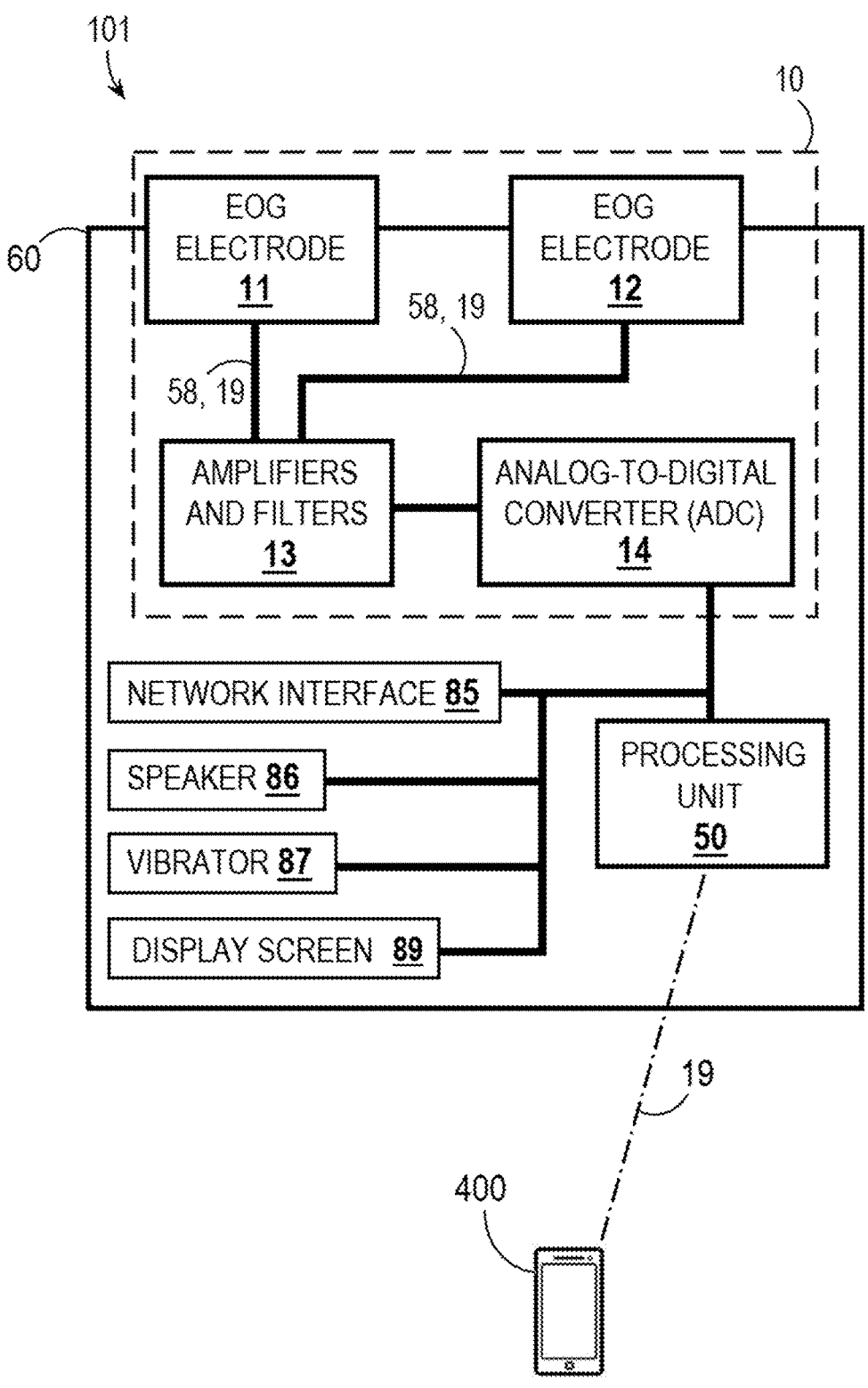
FIG. 9-FIG. 9 shows a block diagram of an example of an auricular electrooculogram (EOG) system housed in a housing structure according to various embodiments described herein.
Figure 10:
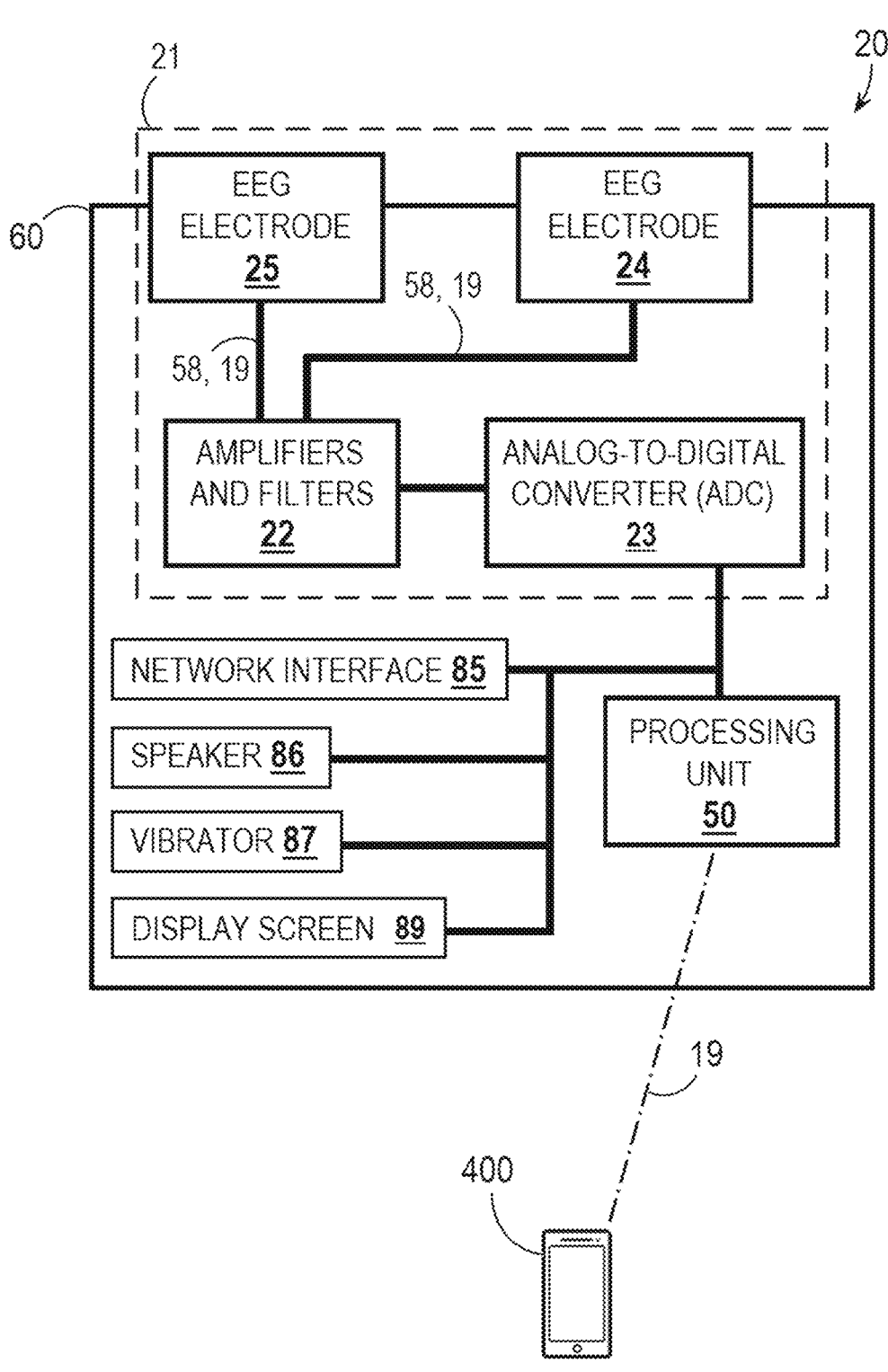
FIG. 10-FIG. 10 depicts a block diagram of an example of an auricular EEG monitoring system housed in a housing structure according to various embodiments described herein.

Generally, an EOG recording module 10 may comprise amplifiers and filters 13 which may pick up the EOG signals generated by extra-ocular movements (movements of eyeball) of a wearer's 900 eye. via the EOG electrodes 11, 12. These EOG electrodes 11, 12, pick up the movements of the eyeball in virtue of the change of orientation of the electric dipole (corneo-retinal potential) between the cornea and the retina. An amplifier of amplifiers and filters 13 is responsible for amplifying the weak electrical signals received from the electrodes 11, 12. (The location of the EOG electrodes 11, 12, affects the EOG amplitude and sensitivity. For the conventional EOG electrodes placement, the EOG amplitudes may range from 50 to 3500 microvolts in human. The sensitivity of EOG recording to eyeball movements may be in the range of 10 to 30 microvolts per degree of saccadic [rapid]eye movement.) The amplifier boosts these signals to a level that can be accurately recorded and displayed. Modern EOG machines use sophisticated amplifiers that minimize noise and ensure signal clarity. EOG machines use various filters, such as high-pass, low-pass, and notch filters, to clean the signals, ensuring that the resulting EOG trace is clear and interpretable. Filters of amplifiers and filters 13 are used to remove unwanted noise and interference from the electrical signals, and as an example, may comprise a 0.01-0.5 Hz high pass filter and a 10-30 Hz low pass filter. Common sources of noise include muscle contractions, electrical interference from other devices, and movement artifacts. An analog-to-digital converter (ADC) 14 may transform the analog electrical signals into digital data. This digital conversion is essential for processing, storing, and displaying the EOG data on a screen or print out. The ADC 14 ensures that the data is accurately digitized, preserving the integrity of the original signals. The ADC 14 may be in communication with a processing unit 50, 401. (FIG. 9)

In some embodiments, the present invention may include an auricular electroencephalogram (EEG) monitoring system 20. Preferably, an auricular EEG monitoring system 20 may comprise an EEG recording module 21 and a plurality of (at least two, but preferably more than two) wired or wireless EEG electrodes 24, 25, 26, 27, (e.g., a first set of a plurality of EEG electrodes 24, 25, 26, 27, a second set of a plurality of EEG electrodes 24, 25, 26, 27, etc.). The first set EEG electrodes 24, 25, 26, 27, may be in electronic communication (e.g., wired or wireless communication) with the EEG recording module 21. All of the EEG electrodes 24, 25, 26, 27, of the first set of a plurality of EEG electrodes 24, 25, 26, 27, may be configured to be coupled to a wearer's first ear 902 or a peri-auricular area 903 around the wearer's first ear. When each EEG electrodes 24, 25, 26, 27, of the first set of a plurality of EEG electrodes 24, 25, 26, 27, is coupled to the wearer's first ear 902 or the peri-auricular area 903 around the wearer's first ear, each EEG electrodes 24, 25, 26, 27, of the first set of a plurality of EEG electrodes 24, 25, 26, 27, is positioned in contact with separate locations on an area of the wearer 901, the area selected from one or more of the following: the external ear 902 of the wearer's first ear, the external ear canal 904 of the wearer's first ear, and the peri-auricular area 903 around the wearer's first ear. The EEG recording module 21 may be configured to record EEG data of the wearer 901 via all of the EEG electrodes 24, 25, 26, 27, of the first set of a plurality of EEG electrodes 24, 25, 26, 27. An auricular EEG monitoring system 20 may comprise a processing unit 50, 401. The EEG recording module 21 may be in electronic communication with the processing unit 50, 401, which is configured to analyze the EEG data of the wearer 900.

Preferably, each EEG electrode 24, 25, 26, 27, of an auricular EEG monitoring system 20 may be housed in a housing structure, such as an earbud-style structure 61, a tubular-shaped structure 67, and a behind-the-ear-hearing-aid-style structure 63. The earbud-style structure 61 may comprise a horizontal portion 62. Each EEG electrode 24, 25, 26, 27, may be configured to be partially embedded in a surface 62A of the horizontal portion 62 of the earbud-style structure 61 with slight protrusion at the surface 62A of the horizontal portion 62 of the earbud-style structure 61. The horizontal portion 62 may comprise a flexible elastic and adaptable material (e.g. soft foam or very soft silicone-type material) and the flexible elastic and adaptable material is configured to have appropriate flexibility, elasticity and adaptability such that each EEG electrode 24, 25, 26, 27, is naturally and snugly in contact with the skin of the wearer's external ear canal 904 when the horizontal portion 62 of the earbud-style structure 61 is inserted into the wearer's external ear canal 904. The behind-the-ear-hearing-aid-style structure 63 may comprise an in-the-ear portion 66. Each EEG electrode 24, 25, 26, 27, may be configured to be partially embedded in a surface 66A of the in-the-ear portion 66 with slight protrusion at the surface 66A of the in-the-ear portion 66. The in-the-ear portion 66 may comprise a flexible elastic and adaptable material (such as soft foam or very soft silicone-type material) and the flexible elastic and adaptable material is configured to have appropriate flexibility, elasticity and adaptability such that each EEG electrode 24, 25, 26, 27, is naturally and snugly in contact with the skin of the wearer's external ear canal 904 when the in-the-ear portion 66 is inserted into the wearer's external ear canal 904. Optionally, the EEG electrodes 24, 25, 26, 27, of the auricular EEG monitoring system 20 may be housed in a tubular-shaped structure 67. The tubular-shaped structure 67 is configured to be made from elastic flexible and adaptable material (such as soft foam or ultra-soft silicone-type material). The elastic flexible and adaptable material of the tubular-shaped structure 67 is configured to have appropriate elasticity, flexibility and adaptability such that it will naturally adapt to the contour of the wearer's external ear canal 904 and snugly fill the interior of the wearer's external ear canal 904 when the tubular-shaped structure 67 is inserted into the wearer's external ear canal 904. All of the EEG electrodes 24, 25, 26, 27, may be configured to be partially embedded in a surface 67A of the tubular-shaped structure 67 with slight protrusion at the surface 67A of the tubular-shaped structure 67 such that all of these electrodes 11, 12, will be naturally and snugly in contact with the skin of the wearer's external ear canal 904. Installing and removing these EEG electrodes 24, 25, 26, 27, will be as easy as inserting and removing the earbud-style structure 61, the behind-the-ear-hearing-aid-style structure 63 or the tubular-shaped structure 67 from the wearer's external ear canal 904.

An EEG recording module 21 may be configured to record EEG data of the wearer 900 via EEG electrodes 24, 25, 26, 27, that optionally may comprise miniature EEG sensor electrodes e.g., wired or wireless miniature dry EEG electrodes (wired and wireless miniature dry EEG electrodes as known in the art). The recorded EEG data may be transmitted or otherwise electronically communicated to a processing unit 50, 401. In some embodiments, an auricular EEG monitoring system 20 may comprise a first set of a plurality of EEG electrodes 24, 25, 26, 27, and each EEG electrode of the first set of a plurality of EEG electrodes 24, 25, 26, 27, is configured as a wireless EEG electrode 24, 25, 26, 27. In some embodiments, an EEG recording module 21 may comprise a wireless EEG amplifier (wireless amplifiers and filters 22). Each wireless EEG electrode of the first set of a plurality of EEG electrodes 24, 25, 26, 27, is housed in a housing structure 60 (such as an earbud-style structure 61, a behind-the-ear-hearing-aid-style structure 63, and a tubular-shaped structure 67) while the EEG recording module 21 and a processing unit 401 are housed in a wearable watch-type structure 400A or a portable smart-phone-type structure 400B.

In some embodiments, an auricular EEG monitoring system 20 may comprise a second EEG recording module 21 that may comprise or may be in communication with each EEG electrode of a second set of a plurality of wired or wireless EEG electrodes 24, 25, 26, 27, (preferably each EEG electrode of the second set of a plurality of EEG electrodes 24, 25, 26, 27, is configured as a wireless EEG electrode 24, 25, 26, 27). Each EEG electrode of the second set of a plurality of EEG electrodes 24, 25, 26, 27, is configured to be coupled to the wearer's second ear 902 or the peri-auricular area 903 around the wearer's second ear 902, and when each EEG electrode of the second set of a plurality of EEG electrodes 24, 25, 26, 27, is coupled to the wearer's second ear 902 or the peri-auricular area 903 around the wearer's second ear 902, each EEG electrode of the second set of a plurality of EEG electrodes 24, 25, 26, 27, is positioned in contact with separate locations on an area of the wearer 900, the area selected from at least one of the following: external ear 902 of the wearer's second ear, external ear canal 904 of the wearer's second ear, and the peri-auricular area 903 around the wearer's second ear. The second EEG recording module 21 may be configured to record EEG data of the wearer 900 via the second set of a plurality of EEG electrodes 24, 25, 26, 27, and the second EEG recording module 21 may be in electronic communication with a processing unit 50, 401. The second EEG recording module 21 may comprise a wireless EEG amplifier (wireless amplifiers and filters 22). Each wireless EEG electrode of the second set of a plurality of EEG electrodes 24, 25, 26, 27, is housed in an earbud-style structure 61(or a behind-the-ear-hearing-aid style structure 63 or a tubular-shaped structure 67) while the EEG recording module 21 is housed in a wearable watch-type structure 400A or a portable smart-phone-type structure 400B.

It should be understood that the auricular electroencephalogram (EEG) monitoring system 20 may comprise one or more auricular EEG recording modules 21. For example, an auricular EEG monitoring system 20 may comprise a first auricular EEG recording module 21 that may be configured to record EEG from the wearer's 900 right ear 902 or right peri-auricular area 903 and a second auricular EEG recording module 21 that may be configured to record EEG from the wearer's 900 left ear 902 or left peri-auricular area 903.

An auricular EEG recording module 21 may record the electrical activities of the brain (EEG signals) of the wearer 900 to generate EEG data. Generally, an auricular EEG recording module 21 may comprise amplifiers and filters 22 which may pick up the electrical activities of the wearer's 900 brain via the EEG electrodes 24, 25, 26, 27. An amplifier of amplifiers and filters 22 is responsible for amplifying the weak electrical signals received from the electrodes 24, 25, 26, 27. The brain's electrical signals are typically very faint, often in the 50 microvolts range (10-200 microvolts when measured from the scalp). The amplifier boosts these signals to a level that can be accurately recorded and displayed. Modern EEG machines use sophisticated amplifiers that minimize noise and ensure signal clarity. Filters of amplifiers and filters 22 are used to remove unwanted noise and interference from the electrical signals. Common sources of noise include muscle contractions, electrical interference from other devices, and movement artifacts. EEG machines use various filters, such as high-pass, low-pass, and notch filters, to clean the signals, ensuring that the resulting EEG trace is clear and interpretable. An analog-to-digital converter (ADC) 23 may transform the analog electrical signals from the brain into digital data. This digital conversion is essential for processing, storing, and displaying the EEG data on a display screen 89, 404C or print out. The ADC 23 ensures that the data is accurately digitized, preserving the integrity of the original signals. The ADC 23 may be in communication with a processing unit 50, 401.

In some embodiments, an auricular EEG monitoring system 20 may be configured as a modified auricular health monitoring system, in which the modified auricular health monitoring system further comprises an ear-canal pulse oximeter 71A. The ear-canal pulse oximeter 71A may be a reflectance pulse oximeter that may comprise a reflectance oximeter module 40A having a wired or wireless (preferably wireless) light generator 41, a wired or wireless (preferably wireless) light detecting sensor (photodiode) 42, and a detection module 45. The wired or wireless light generator 41 and the wired or wireless light detecting sensor 42 are configured to be coupled to the external ear canal 904 of a wearer 900 to be in contact with the skin of the external ear canal of the wearer's ear 902. The wired or wireless light generator 41 comprises a light emitting diode configured to generate light of different wavelengths including red and infrared wavelengths, that are commonly used to measure oxygen saturation in tissue. The wired or wireless light detecting sensor 42 is configured to measure light absorption of different wavelengths, including red and infrared wavelengths. The wired or wireless light generator 41 and the wired or wireless light detecting sensor 42 may be in electronic communication with the detection module 45 through local interface 58 (wire) or wirelessly. The detection module 45 is configured to analyze the data communicated or transmitted from the wired or wireless light generator 41 and the wired or wireless light detecting sensor 42 to record, assess, determine, etc., the wearer's pulse data and the data of the wearer's blood oxygen saturation level (blood oxygen saturation data). The ear-canal pulse oximeter 71A may be configured to be housed in the horizontal portion 62 of an earbud-style structure 61 or a tubular-shaped structure 67 or the in-the-ear portion 66 of a behind-the-ear-hearing-aid-style structure 63. Preferably, the wired or wireless light generator 41 and the wired or wireless light detecting sensor 42 may be housed in a housing structure 60, such as an earbud-style structure 61, a behind-the-ear-hearing-aid-style structure 63, and a tubular-shaped structure 67. The wired or wireless light generator 41 and the wired or wireless light detecting sensor (photodiode) 42 of the ear-canal pulse oximeter 71A may be configured to be partially embedded in the surface 62A, 67A, 66A with slight protrusion at the surface 62A, 67A, 66A of the horizontal portion 62 of the earbud-style structure 61 or the tubular-shaped structure 67 or the in-the-ear portion 66 of the behind-the-ear-hearing-aid-style structure 63. The horizontal portion 62 of the earbud-style structure 61 or the tubular-shaped structure 67 or the in-the-ear-portion 66 of the behind-the-ear-hearing-aid-style structure 63 is configured to be made with flexible elastic adaptable material (e.g., soft foam or ultra-soft silicone material) that is configured to have appropriate flexibility elasticity and adaptability such that the light generator 71 and the light detecting sensor 72 of the ear-canal pulse oximeter 71A will be naturally in close contact with the skin of the wearer's external ear canal 904 and snugly fill the interior of the wearer's external ear canal 904 when the earbud-style structure 61 or the tubular-shaped structure 67 or in-the-ear portion 66 of the behind-the-ear-hearing-aid-style structure 63 is inserted into the wearer's external ear canal 904. (FIGS. 1-3, 14, 16). Wireless pulse oximeters are readily available (such as Aulisa GA 1000-A or GA 1000-P from Turner Medical, Colchester, Connecticut). The ear-canal pulse oximeter 71A is configured to be in wireless and/or wired electronic communication with a processing unit 50, 401, of the auricular EEG monitoring system 20. Preferably, the processing unit 50, 401, is configured to analyze the EEG data recorded by the EEG recording module 21, and the wearer's pulse data and blood oxygen saturation data recorded by the ear-canal pulse oximeter 71A to assess the wearer's health profile, in which the wearer's health profile includes an electroencephalographic profile of the wearer, the wearer's pulse data and blood oxygen saturation data. Preferably, the detection module 45 and a network interface 406 may be housed in a wearable watch-type client device 400A or a portable smart-phone-type client device 400B.

In some embodiments, an auricular EEG monitoring system 20 may be configured as a modified health monitoring system that may comprise an ear-canal pulse oximeter 71A and an auricular EEG monitoring system 20. The auricular EEG monitoring system 20 may comprise one or more sets of EEG electrodes 24, 25, 26, 27, and each set may comprise a plurality of wired or wireless EEG electrodes 24, 25, 26, 27. For example, an auricular EEG monitoring system 20 may comprise a first set of a plurality of EEG electrodes 24, 25, 26, 27, and optionally, the auricular EEG monitoring system 20 may comprise a second set of a plurality of EEG electrodes 24, 25, 26, 27, in which the first set is configured to record EEG from a first ear 902 or a peri-auricular area 903 around the first ear 902 of the wearer 900 and the optional second set is configured to record EEG from a second ear 902 or a peri-auricular area 903 around the second ear 902 of the wearer 900. Preferably, each EEG electrode 24, 25, 26, 27, of the one or more sets of a plurality of EEG electrodes 24, 25, 26, 27, may be configured as a wireless EEG electrode 24, 25, 26, 27. Preferably, the light generator 41 and light detecting sensor 42 of the ear-canal pulse oximeter 71A are configured as a wireless light generator 41 and wireless light detecting sensor 42. The light generator 41 and the light detecting sensor 42 of the ear-canal pulse oximeter 71A and each EEG electrode of the first set of a plurality of EEG electrodes 24, 25, 26, 27, may be housed in a housing structure 60, such as an earbud-style structure 61, a behind-the-ear-hearing-aid-style structure 63, and a tubular-shaped structure 67. The earbud-style structure 61 may comprise a horizontal portion 62, and each EEG electrode of the first set of a plurality of EEG electrodes 24, 25, 26, 27, and the light generator 41 and the light detecting sensor 42 of the ear-canal pulse oximeter 71A are partially embedded in the surface 62A of the horizontal portion 62 with slight protrusion at the surface 62A of the horizontal portion 62. The horizontal portion 62 may comprise a flexible elastic and adaptable material and the flexible elastic and adaptable material is configured to have appropriate flexibility, elasticity and adaptability such that the light generator 41 and the light detecting sensor 42 of the ear-canal pulse oximeter 71A and each EEG electrode of the first set of a plurality of EEG electrodes 24, 25, 26, 27, are in contact with skin of the external ear canal 904 of the wearer's first ear 902 when the horizontal portion 62 is inserted into the external ear canal 904 of the wearer's first ear 902. The behind-the-ear-hearing-aid-style structure 63 may comprise an in-the-ear portion 66 and a behind-the-ear portion 65, and the light generator 41 and the light detecting sensor 42 of the ear-canal pulse oximeter 71A and each EEG electrode of the first set of a plurality of EEG electrodes 24, 25, 26, 27, are partially embedded in the surface 66A of the in-the-ear portion 66 with slight protrusion at the surface 66A of the in-the-ear portion 66. The in-the-ear portion 66 may comprise a flexible elastic and adaptable material and the flexible elastic and adaptable material is configured to have appropriate flexibility, elasticity and adaptability such that the light generator 41 and the light detecting sensor 42 of the ear-canal pulse oximeter 71A and each EEG electrode of the first set of a plurality of EEG electrodes 24, 25, 26, 27, are naturally in contact with the skin of the external ear canal 904 of the wearer's first ear 902 when the in-the-ear portion 66 is inserted into the external ear canal 904 of the wearer's first ear 902. The tubular-shaped structure 67 may comprise a surface 67A, and the light generator 41 and the light detecting sensor 42 of the ear-canal pulse oximeter 71A and each EEG electrode of the first set of a plurality of EEG electrodes 24, 25, 26, 27, may be partially embedded in the surface 67A of the tubular-shaped structure 67 with slight protrusion at the surface 67A of the tubular-shaped structure 67. The tubular-shaped structure 67 may comprise a flexible elastic and adaptable material and the flexible elastic and adaptable material is configured to have appropriate flexibility, elasticity and adaptability such that the light generator 41 and the light detecting sensor 42 of the ear-canal pulse oximeter 71A and each EEG electrode of the first set of a plurality of EEG electrodes 24, 25, 26, 27, are naturally in contact with the skin of the external ear canal 904 of the wearer's first ear 902 when the tubular-shaped structure 67 is inserted into the external ear canal 904 of the wearer's first ear 902. Preferably, the EEG recording module 31, the detection module 45 and the processing unit 401 are housed in a wearable watch-type structure 400A or a portable smart-phone-type structure 400B. Preferably, the auricular EEG monitoring system 20 further comprises a network interface 85 and a display screen 89, 404C, such as a display screen 89 on the housing structure 60 and a display screen 404C on a client device 400 of the wearer 900. The network interface 85 is in electronic communication with the processing unit 50, 401, and the display screen 89 and/or display screen 404C. Preferably, the network interface 85 is configured to send signals to the display screen 404C that is configured to generate a visible notification (with visual display) on the client device 400 of the wearer 900 describing the wearer's electroencephalographic profile, pulse data, and blood oxygen saturation data and/or profile. Optionally, the network interface 85 is configured to send signals to the display screen 89 that is configured to generate a visible notification on the housing structure 60 describing the wearer's electroencephalographic profile, pulse data, and blood oxygen saturation data and/or profile. As used herein, a display screen 89, 404C is a visual output device that presents information in a visible form, such as text, data, images, or graphics. In some sense, the term "display screen" could be interchangeable as "visual display". Display screens are found on computer monitors, smartphones, health trackers and other electronic devices.

In some embodiments, the present invention may include an auricular electrocardiogram (ECG) system 30 that may comprise an auricular ECG recording module 31. The ECG recording module 31 may comprise two or more wired or wireless ECG electrodes 32, 33, in electronic communication with the ECG recording module 31. The ECG electrodes 32, 33, may be configured to be coupled to a wearer's ear 902 or a peri-auricular area 903 around the wearer's ear 902. When the ECG electrodes 32, 33, are coupled to the wearer's ear 902 or the peri-auricular area 903 around the wearer's ear 902 the ECG electrodes 32, 33, are positioned in contact with separate locations on an area of the wearer 900, the area selected from at least one of the following: external ear of the wearer's ear 902, external ear canal 904 of the wearer's ear, and the peri-auricular area 903 around the wearer's ear. These locations that the ECG electrodes 32, 33, are attached to may be adequately separated (with different angles or directions) relative to the location of the heart of the wearer 900 so that they can pick up some differences of the cardiac action potentials in order to enable the ECG recording module 31 to perform an ECG. The ECG recording module 31 may be configured to record ECG data of the wearer 90 via the ECG electrodes 32, 33, and the ECG recording module 31 may be in electronic communication with a processing unit 50, 401, which may be configured to record and analyze the ECG data from the ECG recording module 31.

Figure 11:
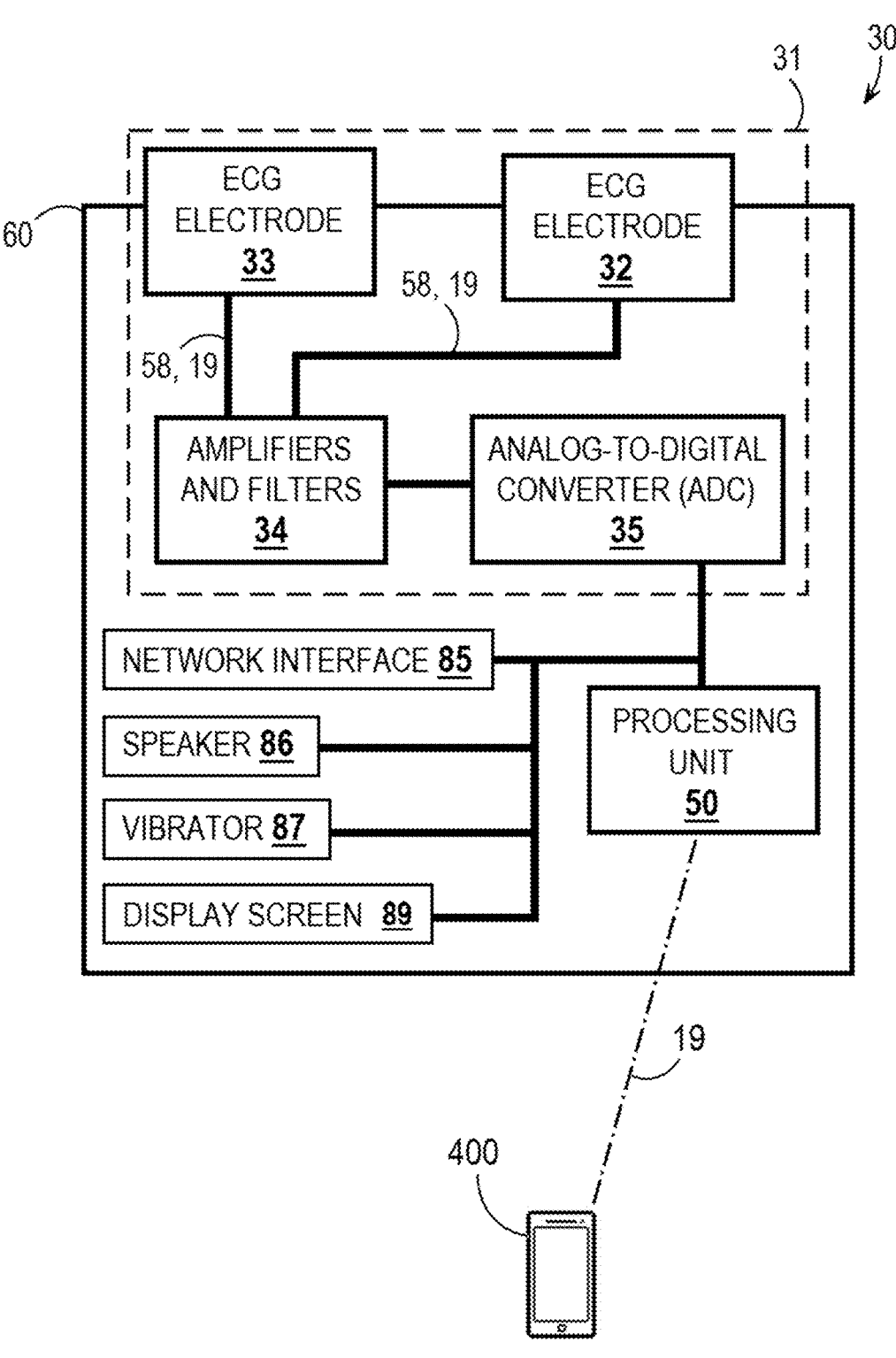
FIG. 11-FIG. 11 illustrates a block diagram of an example of an auricular ECG system housed in a housing structure according to various embodiments described herein.

An auricular electrocardiogram (ECG) system 30 may comprise an auricular ECG recording module 31 that may record and analyze the electrical activity of the wearer's 900 heart, such as to diagnose heart conditions and cardiac arrhythmias. Generally, amplifiers and filters 34 may pick up the electrical activity of the wearer's 900 heart via the ECG electrodes 32, 33. An amplifier of amplifiers and filters 34 is responsible for amplifying the weak electrical signals received from the electrodes 32, 33. The heart's electrical signals are typically very faint, in the range of 10 microvolts to 5 millivolts, depending on chest or limb lead and depending on different waves (P, QRS or T waves). An amplifier of amplifiers and filters 34 boosts these signals to a level that can be accurately recorded and displayed. Modern ECG machines use sophisticated amplifiers that minimize noise and ensure signal clarity. Filters of amplifiers and filters 34 are used to remove unwanted noise and interference from the electrical signals. Common sources of noise include muscle contractions, electrical interference from other devices, and movement artifacts. ECG machines use various filters, such as high-pass, low-pass, and notch filters, to clean the signals, ensuring that the resulting ECG trace is clear and interpretable. An analog-to-digital converter (ADC) 35 may transform the analog electrical signals from the heart into digital data. This digital conversion is essential for processing, storing, and/or displaying the ECG data on a display screen 89, 404C, or print out. The ADC 35 ensures that the data is accurately digitized, preserving the integrity of the original signal. The ADC 35 may be in communication with a processing unit 50, 401. (FIG. 11).

In some embodiments, the present invention may comprise a housing structure 60 which may be configured to be coupled to an ear 902 of a wearer 900 and/or to the peri-auricular area 903 around an ear 902 of a wearer 900. In some embodiments, a housing structure 60 may comprise an earbud style structure 61, a behind-the-ear-hearing-aid-style structure 63, or a tubular-shaped structure 67. In some embodiments, a housing structure 60, such as an earbud style structure 61, may comprise a sound conduit 68 which may extend through the housing structure 60 (such as shown in FIGS. 1-4) and which may facilitate the ability of sound to enter the ear 902. Preferably, a sound conduit 68 may comprise an opening, channel, conduit, etc., which may extend through a portion of an earbud style structure 61 so that sound waves may pass through the sound conduit 68 to facilitate or enable the wearer 900 to hear sounds in the environment.

In some embodiments, the present invention may comprise a processing unit 50 which may be contained in a housing structure 60. A processing unit 50 may include a processor 51 that may comprise a hardware device for executing software instructions. The processor 51 can be any custom made or commercially available processor, a central processing unit (CPU), an auxiliary processor among several processors associated with the processing unit 50, a semiconductor-based microprocessor (in the form of a microchip or chip set), or generally any device for executing software instructions. Optionally, when the processing unit 50 is in operation, the processor 51 may be configured to execute software stored within a memory 55, to communicate data to and from the memory 55, and to generally control one or more operations of the various systems of this invention (such as including EOG system 101, sleep monitoring systems 102, 103, auricular health monitoring system 104 and auricular hybrid brain-computer interface system 105) pursuant to the software instructions and/or from instructions. In an exemplary embodiment, the processor 51 may include a mobile optimized processor, such as optimized for power consumption and mobile applications. Preferably, a power source 88, such as a rechargeable lithium battery, other type of battery, capacitor, etc., may be configured to supply power to the processing unit 50 and any other component that may require electric power.

In some embodiments, a processing unit 50 may comprise one or more I/O interfaces 52 which can be used to provide user input and display system output data, such as operational status. The I/O interfaces 52 can include, for example, buttons, knobs, switches, LED indicator lights, LED display, LCD display, a serial port, a parallel port, a small computer system interface (SCSI), an infrared (IR) interface, a radio frequency (RF) interface, a universal serial bus (USB) interface, and the like.

Figure 12:
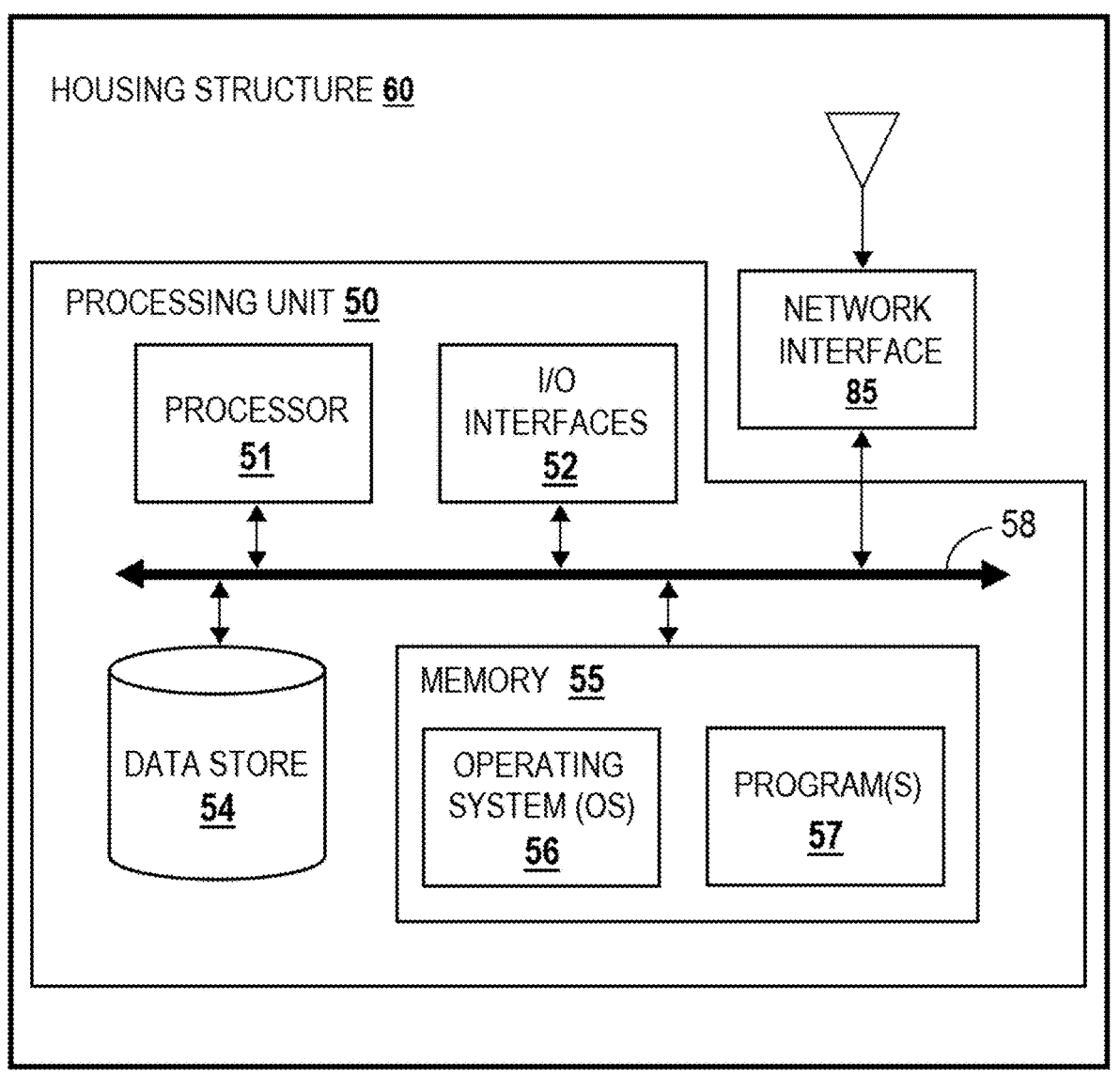
FIG. 12-FIG. 12 shows a block diagram of an example of a processing unit housed in a housing structure according to various embodiments described herein.

In some embodiments, a processing unit 50 may comprise a memory 55 that may include any of volatile memory elements (e.g., random access memory (RAM, such as DRAM, SRAM, SDRAM, etc.)), nonvolatile memory elements (e.g., ROM, hard drive, etc.), and combinations thereof. Moreover, the memory 55 may incorporate electronic, magnetic, optical, and/or other types of storage media. Note that the memory 55 may have a distributed architecture, where various components are situated remotely from one another, but can be accessed by the processor 51. Optionally, memory 55 can include one or more software programs, each of which includes an ordered listing of executable instructions for implementing logical functions. Optionally, the software in the memory system 55 includes a suitable operating system (O/S) 56 and program(s) 57. The operating system 56 essentially controls the execution of input/output interface 52 and other element functions, and provides scheduling, input-output control, file and data management, memory management, and communication control and related services. The operating system 56 may be, for example, LINUX (or another UNIX variant), Android (available from Google), Symbian OS, Microsoft Windows CE, Microsoft Windows 7 Mobile, iOS (available from Apple, Inc.), webOS (available from Hewlett Packard), Blackberry OS (Available from Research in Motion), and the like. The programs 57 may include various applications, add-ons, etc. configured to provide end user functionality of various systems of this invention. (FIG. 12).

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequences of actions described herein can be considered to be embodied entirely within any form of computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

In some embodiments, the present invention may comprise a network interface 85 which may be contained in a housing structure 60 and which may enable wired and/or wireless communication between one or more components, such as processing unit 50, etc., with one or more client devices 400. Preferably, a network interface 85 may comprise a radio that may operate via WiFi and/or Bluetooth communication standards. In further embodiments, a network interface 85 may comprise a radio that may operate on a cellular band and may communicate with or receive a Subscriber Identity Module (SIM) card or other wireless network identifier. Any number of suitable wireless data communication protocols, techniques, or methodologies can be supported by a network interface 85, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Near-Field Communication (NFC); Frequency Hopping Spread Spectrum; Long Term Evolution (LTE); cellular/wireless/cordless telecommunication protocols (e.g. 3G/4G/5G, etc.); wireless home network communication protocols; paging network protocols; magnetic induction; satellite data communication protocols; wireless hospital or health care facility network protocols such as those operating in the WMTS bands; GPRS; proprietary wireless data communication protocols such as variants of Wireless USB; and any other protocols for wireless communication. In further embodiments, a network interface 85 may enable wired network communication and may include, for example, an Ethernet card or adapter (e.g., 10BaseT, Fast Ethernet, Gigabit Ethernet, 10 GbE) or a wireless local area network (WLAN) card or adapter (e.g., 802.11a/b/g/n). The network interface 85 may include address, control, and/or data connections to enable appropriate communications on the network.

In some embodiments, the present invention may comprise one or more client devices 400. A client device 400 may comprise a processing unit 401 contained within the client device 400 that may be in electronic communication 19 with processing unit 50 of a housing structure 60 with a network interface 85 via Bluetooth, WiFi, or other connection means. For example, a processing unit 401 may be part of a separate client device 400, such as a smart phone, smart watch, computer, etc., that may be in wired or wireless communication with a processing unit 50 via a network interface 85.

Figure 20:
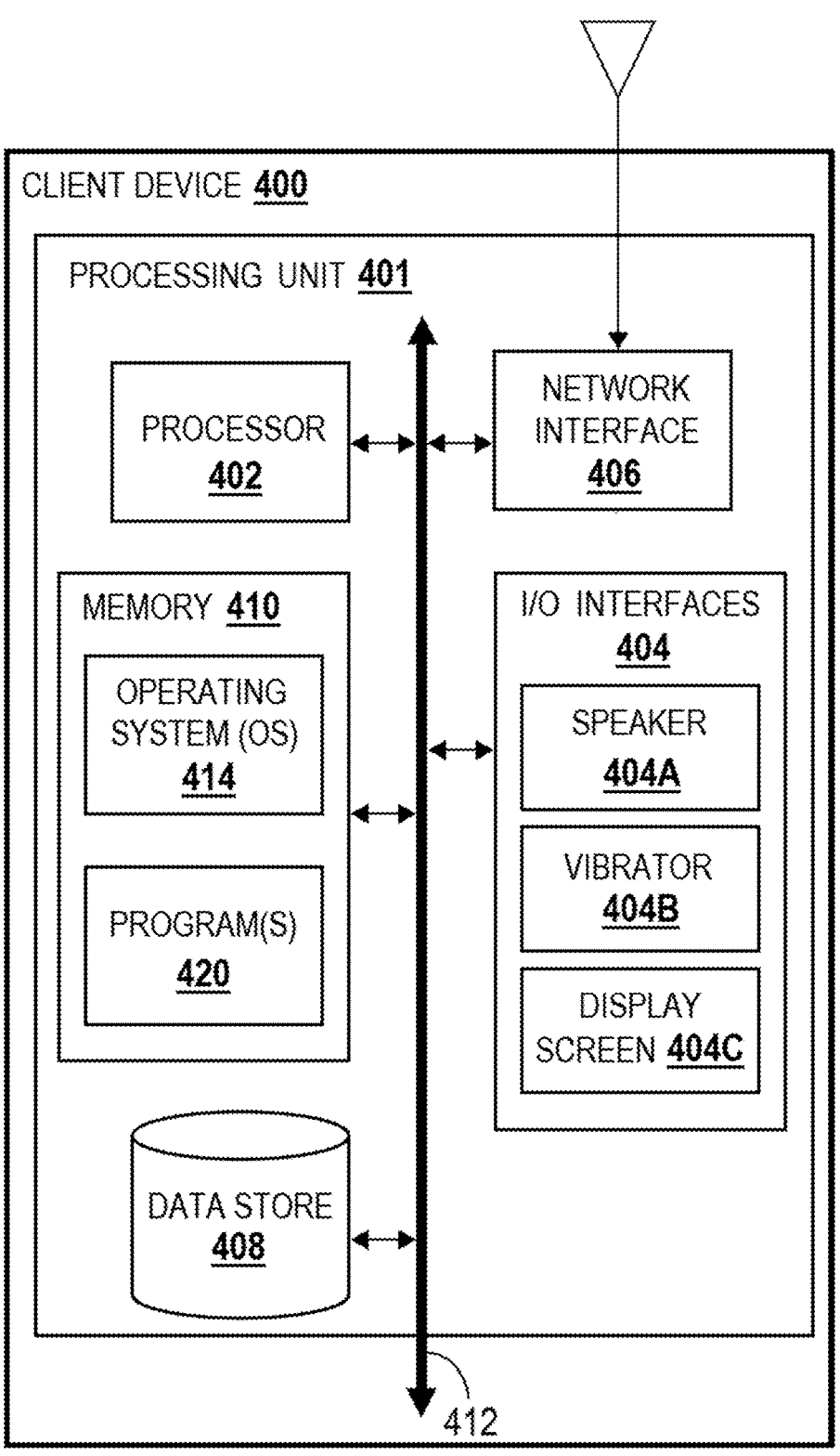
FIG. 20-FIG. 20 illustrates a block diagram of an example of a client device having a processing unit according to various embodiments described herein.
Figure 21:
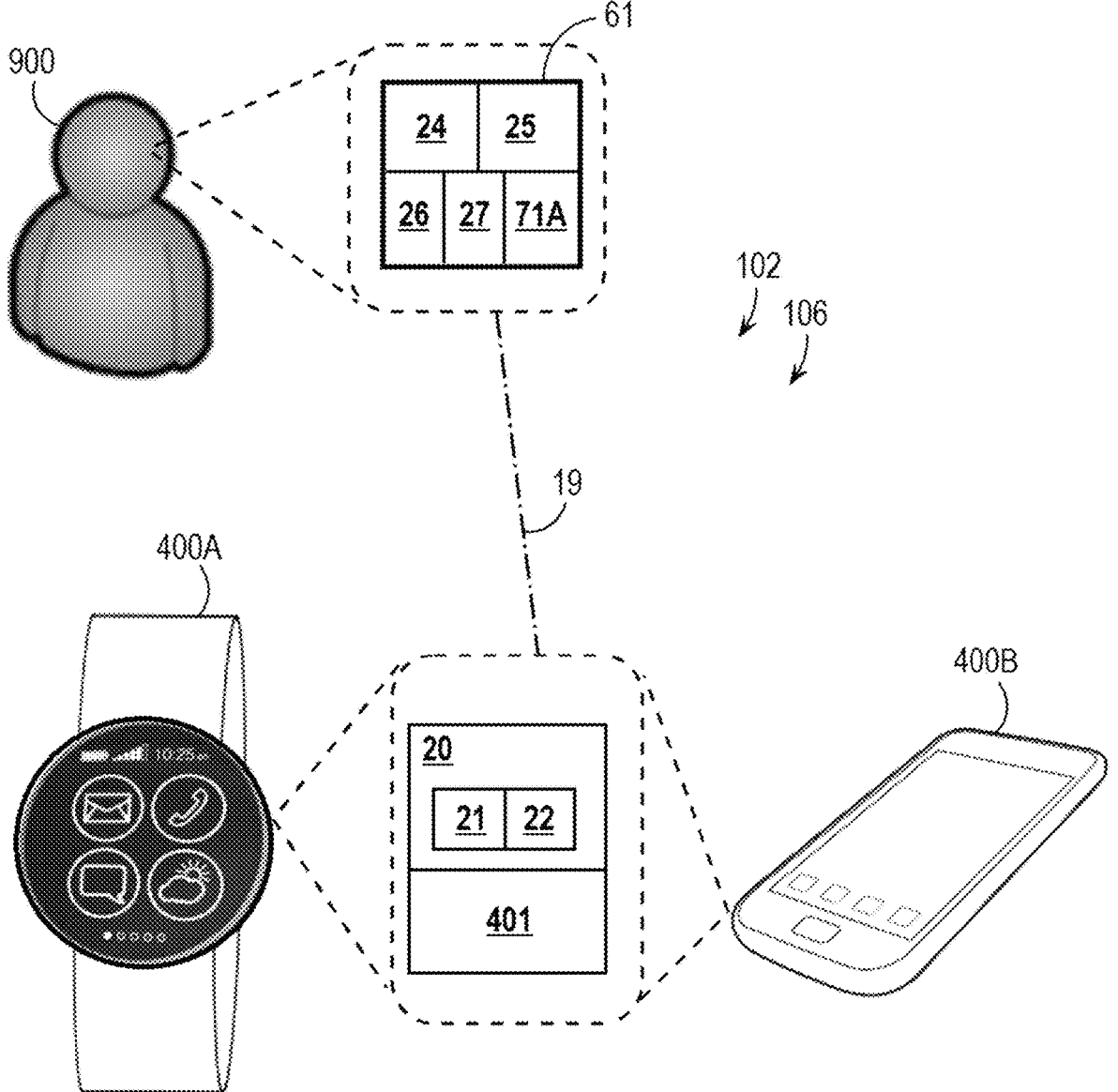
FIG. 21-FIG. 21 shows a schematic diagram of some exemplary components of examples of an auricular sleep monitoring system and a concise sleep monitoring system according to various embodiments described herein.
Figure 22:
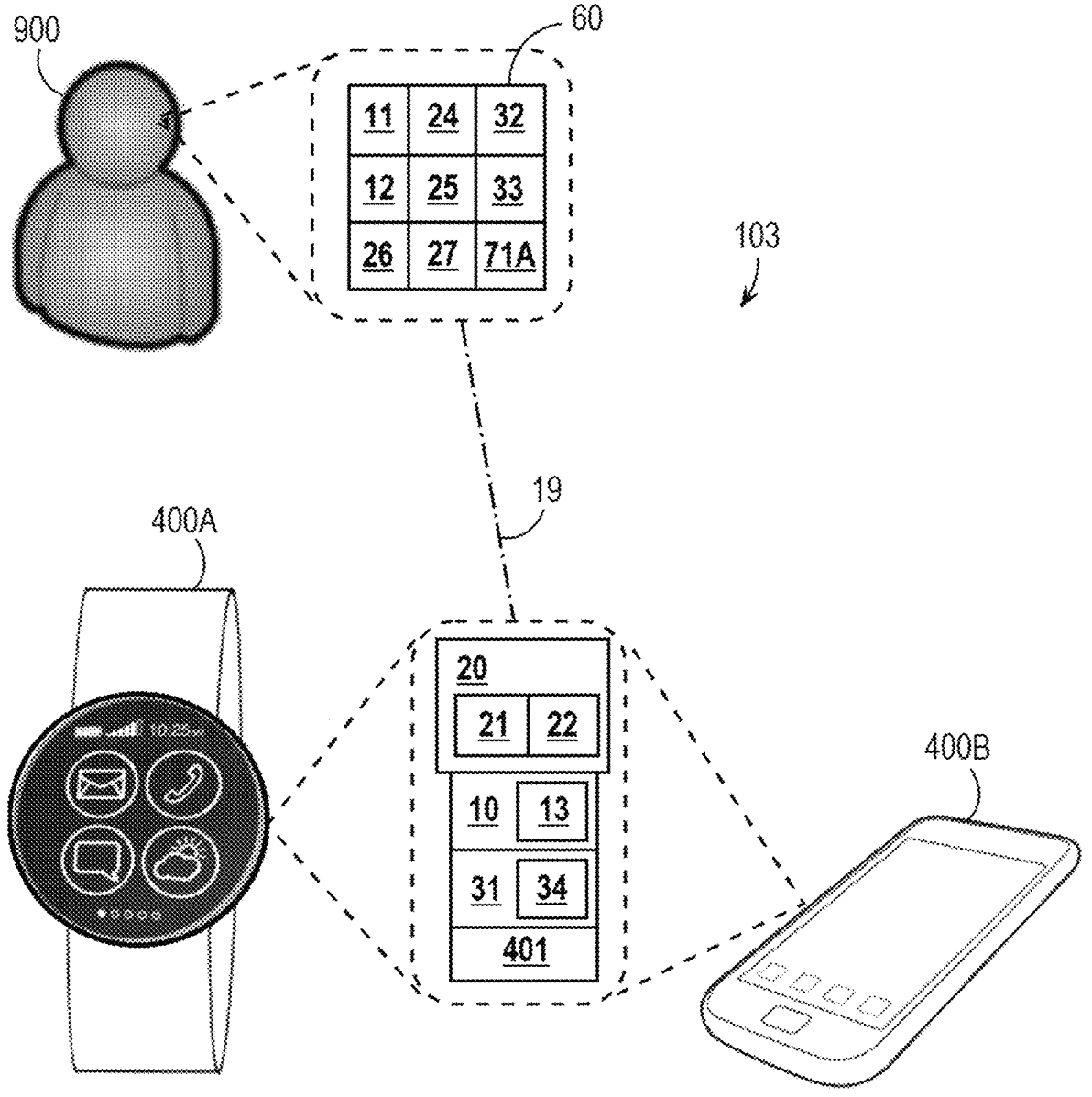
FIG. 22-FIG. 22 depicts a schematic diagram of some exemplary components of another example of a comprehensive sleep monitoring system according to various embodiments described herein.

Referring to FIG. 20, in an exemplary embodiment, a block diagram illustrates a client device 400 of which may be a type of computing platform. Client devices 400 may include wearable client devices 400A (e.g., smart watches, wrist mounted fitness trackers, etc.) and portable smartphone-type client devices 400B (e.g., smartphones, tablet computers, etc.). A client device 400 can be a digital device that, in terms of hardware architecture, comprises a processing unit 401 that preferably includes a processor 402, input/output (I/O) interfaces 404, a network interface 406, a data store 408, and memory 410. It may be appreciated by those of ordinary skill in the art that FIG. 20 depicts the client device 400 in an oversimplified manner, and a practical embodiment may include additional components and suitably configured processing logic to support known or conventional operating features that are not described in detail herein. The components (402, 404, 406, 408, and 410) are communicatively coupled via a local interface 412. The local interface 412 can be, for example but not limited to, one or more buses or other wired or wireless connections, as is known in the art. The local interface 412 can have additional elements, which are omitted for simplicity, such as controllers, buffers (caches), drivers, repeaters, and receivers, among many others, to enable communications.

The processor 402 is a hardware device for executing software instructions. The processor 402 can be any custom made or commercially available processor, a central processing unit (CPU), an auxiliary processor among several processors associated with the client device 400, a semiconductor-based microprocessor (in the form of a microchip or chip set), or generally any device for executing software instructions. When the client device 400 is in operation, the processor 402 is configured to execute software stored within the memory 410, to communicate data to and from the memory 410, and to generally control operations of the client device 400 pursuant to the software instructions. In an exemplary embodiment, the processor 402 may include a mobile optimized processor such as optimized for power consumption and mobile applications.

The I/O interfaces 404 can be used to receive data and user input and/or for providing system output. User input can be provided via a plurality of I/O interfaces 404, such as a keypad, a touch screen, speaker, a camera, a microphone, a scroll ball, a scroll bar, buttons, barcode scanner, voice recognition, eye gesture, and the like. System output can be provided via a display screen 404C such as a liquid crystal display (LCD), touch screen, and the like. The I/O interfaces 404 can also include, for example, a global positioning service (GPS) radio, a serial port, a parallel port, a small computer system interface (SCSI), an infrared (IR) interface, a radio frequency (RF) interface, a universal serial bus (USB) interface, and the like. The I/O interfaces 404 can include a graphical user interface (GUI) that enables a user to interact with the client device 400. Additionally, the I/O interfaces 404 may be used to output notifications to a user and can include a speaker 404A or other sound emitting device configured to emit audio notifications, a vibrational device or vibrator 404B configured to vibrate, shake, or produce any other series of rapid and repeated movements to produce haptic notifications, and/or a light emitting diode (LED) or other light emitting element which may be configured to illuminate to provide a visual notification.

The network interface 406 enables wireless communication to an external access device or network. Any number of suitable wireless data communication protocols, techniques, or methodologies can be supported by the network interface 406, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; Long Term Evolution (LTE); cellular/wireless/cordless telecommunication protocols (e.g. 3G/4G, etc.); wireless home network communication protocols; paging network protocols; magnetic induction; satellite data communication protocols; wireless hospital or health care facility network protocols such as those operating in the WMTS bands; GPRS; proprietary wireless data communication protocols such as variants of Wireless USB; and any other protocols for wireless communication.

The data store 408 may be used to store data and is therefore a type of memory. The data store 408 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 408 may incorporate electronic, magnetic, optical, and/or other types of storage media.

The memory 410 may include any of volatile memory elements (e.g., random access memory (RAM, such as DRAM, SRAM, SDRAM, etc.)), nonvolatile memory elements (e.g., ROM, hard drive, etc.), and combinations thereof. Moreover, the memory 410 may incorporate electronic, magnetic, optical, and/or other types of storage media. Note that the memory 410 may have a distributed architecture, where various components are situated remotely from one another, but can be accessed by the processor 402. The software in memory 410 can include one or more software programs 420, each of which includes an ordered listing of executable instructions for implementing logical functions. In the example of FIG. 20, the software in the memory system 410 includes a suitable operating system (O/S) 414 and programs 420.

The operating system 414 essentially controls the execution of other computer programs, and provides scheduling, input-output control, file and data management, memory management, and communication control and related services. The operating system 414 may be, for example, LINUX (or another UNIX variant), Android (available from Google), Symbian OS, Microsoft Windows CE, Microsoft Windows 7 Mobile, Microsoft Windows 10, iOS (available from Apple, Inc.), webOS (available from Hewlett Packard), Blackberry OS (Available from Research in Motion), and the like.

The programs 420 may include various applications, add-ons, etc. configured to provide end user functionality with the client device 400. For example, exemplary programs 420 may include, but not limited to, a web browser, social networking applications, streaming media applications, games, mapping and location applications, electronic mail applications, financial applications, and the like.

In some embodiments, the present invention may comprise an ancillary sleep surveillance system 70. In some embodiments, an ancillary sleep surveillance system 70 may comprise one or more of the following sensors or monitors: a pulse oximeter 71, a peripheral arterial tonometry (PAT) monitor 72, an airflow sensor (airflow meter) 73, an actigraphy sensor (or motion sensor) 74, a breathing monitor (respiratory inductance plethysmography (RIP) monitor) 75, a leg movement sensor 76, a body temperature sensor 77, an electromyogram (EMG) sensor (usually EMG of submental muscle [chin] and/or anterior tibialis muscle [leg]) 78, an electrocardiogram (ECG) sensor 79, a body position sensor 80, a blood pressure monitor 81, and/or any other body parameter measuring sensor.

Preferably, a pulse oximeter 71 may be configured to record pulse data of the wearer 900 and blood oxygen saturation data of the wearer 900. Preferably, a PAT monitor 72 may be configured to record breathing disturbances data of the wearer 900. Preferably, an airflow sensor 73 may be configured to record nasal airflow data of the wearer 900. Preferably, an actigraphy sensor 74 may be configured to record motion data of the wearer 900. Preferably, a leg movement sensor 76 may be configured to record leg movement data of the wearer 900. Preferably, a RIP monitor 75 may be configured to be coupled to chest or abdomen of the wearer 900 and is configured to record respiratory effort data of the chest or abdomen of the wearer 900. Preferably, the body temperature sensor 77 may be configured to record the body temperature data of the wearer 900. Preferably, the electromyogram (EMG) sensor 78 may be configured to record the EMG data of the wearer 900. Preferably, the electrocardiogram (ECG) sensor 79 may be configured to record the ECG data of the wearer 900. Preferably, the body position sensor 80 may be configured to record the body position data of the wearer 900. Preferably, the blood pressure monitor 81 may be configured to record the blood pressure data of the wearer 900.

In some embodiments, the present invention may comprise a novel wired or wireless ear-canal pulse oximeter 71A. The ear-canal pulse oximeter 71A may be a reflectance pulse oximeter that may comprise a reflectance oximeter module 40A having a wired or wireless light generator 41, a wired or wireless light detecting sensor (photodiode) 42, and a detection module 45. The wired or wireless light generator 41 and the wired or wireless light detecting sensor 42 are configured to be coupled to the external ear canal 904 of a wearer 900 to be in contact with the skin of the external ear canal of the wearer's ear 902. The wired or wireless light generator 41 comprises a light emitting diode configured to generate light of different wavelengths including red and infrared wavelengths, that are commonly used to measure oxygen saturation in tissue. The wired or wireless light detecting sensor 42 is configured to measure light absorption of different wavelengths, including red and infrared wavelengths. The wired or wireless light generator 41 and the wired or wireless light detecting sensor 42 may be in electronic communication with the detection module 45 through local interface 58 (wire) or wirelessly. The detection module 45 is configured to analyze the data communicated or transmitted from the wired or wireless light generator 41 and the wired or wireless light detecting sensor 42 to record, assess, determine, etc., the wearer's pulse data and the data of the wearer's blood oxygen saturation level (blood oxygen saturation data). The ear-canal pulse oximeter 71A may be configured to be housed in a housing structure 60 selected from one of the following: a horizontal portion 62 of an earbud-style structure 61, a tubular-shaped structure 67, and an in-the-ear portion 66 of a behind-the-ear-hearing-aid-style structure 63. Preferably, the wired or wireless light generator 41 and the wired or wireless light detecting sensor 42 may be housed in a housing structure 60, such as an earbud-style structure 61, a behind-the-ear-hearing-aid-style structure 63, a tubular-shaped structure 67, etc. The wired or wireless light generator 41 and the wired or wireless light detecting sensor (photodiode) 42 of the ear-canal pulse oximeter 71A may be configured to be partially embedded in the surface 62A of the horizontal portion 62 with slight protrusion at the surface 62A of the horizontal portion 62 of the earbud-style structure 61 or partially embedded in the surface 67A of the tubular shaped structure 67 with slight protrusion at the surface 67A of the tubular-shaped structure 67 or partially embedded in the surface 66A of the in-the-ear portion 66 with slight protrusion at the surface 66A of the in-the-ear portion 66 of the behind-the-ear-hearing-aid-style structure 63. The horizontal portion 62 of the earbud-style structure 61 or the tubular-shaped structure 67 or the in-the-ear-portion 66 of the behind-the-ear-hearing-aid-style structure 63 is configured to be made with flexible elastic adaptable material (e.g., soft foam or ultra-soft silicone material) that is configured to have appropriate flexibility elasticity and adaptability such that the light generator 71 and the light detecting sensor 72 of the ear-canal pulse oximeter 71A will be naturally and snugly in close contact with the skin of the wearer's external ear canal 904 and snugly fill the interior of the wearer's external ear canal 904 when the earbud-style structure 61 or the tubular-shaped structure 67 or in-the-ear portion 66 of the behind-the-ear-hearing-aid-style structure 63 is inserted into the wearer's external ear canal 904. (FIGS. 1-3, 14, 16). Wireless pulse oximeters are readily available (such as Aulisa GA 1000-A or GA 1000-P from Turner Medical, Colchester, Connecticut). The ear-canal pulse oximeter 71A is configured to be in wireless and/or wired electronic communication with a processing unit 50, 401. In some embodiments, the ear-canal pulse oximeter 71A further comprises a network interface 85 and at least one of the following: a speaker 86, 404A, a vibrator 87, 404B, a display screen 89 on the housing structure 60 and a display screen 404C on a client device 400 of the wearer 900. The network interface 85 is in electronic communication with the speaker 86, 404A, vibrator 87, 404B, detection module 45, the display screen 89 on the housing structure 60, and/or the display screen 404C on the client device 400, and the network interface 85 is configured to generate a visible notification on the display screen 89 on the housing structure 60 and/or on the display screen 404C on the client device 400 describing the wearer's pulse data and/or profile and blood oxygen saturation data and/or profile. Preferably, the detection module 45, display screen 404C, and the network interface 406 may be housed in a wearable watch-type client device 400A or a portable smartphone-type client device 400B. The network interface 85 may be configured to automatically generate a notification to the client device 400 of the wearer 900 immediately when the processing unit 50, 401, detects presence of the blood oxygen saturation of the wearer 900 dropping below a pre-determined level. Preferably, the speaker 86, 404A, may be configured to automatically generate an audible notification to the wearer 900 immediately to alert the wearer 900 to take appropriate action when the processing unit 50, 401, detects presence of the blood oxygen saturation of the wearer 900 dropping below the pre-determined level. Preferably, the vibrator 87, 404B, may be configured to automatically generate a tactile notification to the wearer 900 immediately to alert the wearer 900 to take appropriate action when the processing unit 50, 401, detects presence of the blood oxygen saturation of the wearer 900 dropping below the pre-determined level.

In some embodiments, the present invention may comprise a concise at-home sleep monitoring system 102. The concise at-home sleep monitoring system 102 preferably comprises an integration of the aforementioned auricular electroencephalography (EEG) monitoring system 20 and an ancillary sleep surveillance system 70. In some embodiments, an ancillary sleep surveillance system 70 may comprise at least one of the following sensors or monitors: a pulse oximeter 71, a peripheral arterial tonometry (PAT) monitor 72, an airflow sensor (airflow meter) 73, an actigraphy sensor (or motion sensor) 74, a breathing monitor (respiratory inductance plethysmography (RIP) monitor) 75, a leg movement sensor 76 a body temperature sensor 77, an electromyogram (EMG) sensor (usually EMG of submental muscle [chin] and/or anterior tibialis muscle [leg]) 78, an electrocardiogram (ECG) sensor 79, a body position sensor 80, a blood pressure monitor 81, and/or any other body parameter measuring sensor.

The concise at-home sleep monitoring system 102 further comprises a processing unit 50, 401. The processing unit 50, 401, may be in electronic communication with the one or more auricular EEG recording modules 21 of the auricular EEG monitoring system 20. The processing unit 50, 401, may also be in electronic communication with each comprising (incorporated) sensor or monitor of the ancillary sleep-surveillance system 70, such as pulse oximeter 71, peripheral arterial tonometry (PAT) monitor 72, airflow sensor 73, actigraphy sensor (motion sensor) 74, breathing monitor (respiratory inductance plethysmography (RIP) monitor) 75, leg movement sensor 76, ECG sensor 79, EMG sensor 78, body temperature sensor 77, body position sensor 80, and blood pressure monitor 81, etc.

Preferably, a pulse oximeter 71 may be configured to record pulse data of the wearer 900 and blood oxygen saturation data of the wearer 900. Preferably, a PAT monitor 72 may be configured to record breathing disturbances data of the wearer 900. Preferably, an airflow sensor 73 may be configured to record nasal airflow data of the wearer 900. Preferably, an actigraphy sensor 74 may be configured to record motion data of the wearer 900. Preferably, a leg movement sensor 76 may be configured to record leg movement data of the wearer 900. Preferably, a RIP monitor 75 may be configured to be coupled to chest or abdomen of the wearer 900 and is configured to record respiratory effort data of the chest or abdomen of the wearer 900. Preferably, a body temperature sensor 77 may be configured to record body temperature data of the wearer 900. Preferably, an EMG sensor 78 (usually for EMG of wearer's chin muscle or anterior tibialis muscle) may be configured to record EMG data of the wearer 900. Preferably, an ECG sensor may be configured to record ECG data of the wearer 900. Preferably, a body position sensor may be configured to record body position data of the wearer 900. Preferably, a blood pressure monitor 81 may be configured to record blood pressure data of the wearer 900.

The processing unit 50, 401, may be configured to analyze the data collected or recorded by the EEG recording module (s) 21 and the data collected or recorded by the ancillary sleep-surveillance system 70, {the ancillary sleep surveillance system 70 includes one or more of the following: pulse oximeter 71, peripheral arterial tonometry (PAT) monitor 72, airflow sensor 73, actigraphy sensor (motion sensor) 74, breathing monitor (respiratory inductance plethysmography [RIP] monitor) 75, leg movement sensor 76, ECG sensor 79, EMG sensor 78, body temperature sensor 77, body position sensor 80, blood pressure monitor 81, etc.} With these data, the processing unit 50, 401, is further configured to assess the wearer's sleep profile, using sophisticated sleep analysis algorithms. The sleep profile may include one or more of: sleep architecture, sleep stages, sleep latency, sleep duration, duration of each sleep stage, sleep quality, sleep density, presence of sleep apnea (including obstructive sleep apnea and central sleep apnea) and Apnea-Hypopnea Index (AHI) score. With the help of sleep analysis algorithms, the processing unit 50, 401, is further configured to detect presence of sleep disorders, which may include narcolepsy, restless leg syndrome, periodic limb movement disorder, rapid-eye-movement (REM) sleep behavior disorder, parasomnias, and insomnia.

In some embodiments, the concise (at-home) sleep monitoring system 102 may comprise a housing structure 60 which may be configured as an earbud style structure 61. Preferably, the concise sleep monitoring system 102 may comprise an EEG recording module 21 that may be housed in a housing structure 60, and the housing structure 60 may be an earbud-style structure 61. Preferably, the earbud-style structure 61 may comprise a horizontal portion 62 and the EEG electrodes 24, 25, 26, 27, may be partially embedded in the surface 62A of the horizontal portion 62 with slight protrusion at the surface 62A of the horizontal portion 62. The horizontal portion 62 may comprise a flexible elastic and adaptable material (for example: soft foam or soft silicone type material, such as pacifier-grade silicone), and the flexible elastic and adaptable material may be configured to have appropriate flexibility, elasticity and adaptability such that the EEG electrodes 24, 25, 26, 27, are naturally and snugly in contact with skin of the external ear canal 904 of the wearer's ear 902 when the horizontal portion 62 is inserted into the external ear canal 904 of the wearer's ear 902. The soft foam or silicone-type material will facilitate steady uniform and easy installation of the EEG electrodes 24, 25, 26, 27. Since the EEG electrodes 24, 25, 26, 26 are integrated and partially embedded in the surface 62A of the horizontal portion 62 of earbud-style structure 61, accidental dislodgement of an individual electrode 24, 25, 26, 27 can be avoided. Being snugly filled inside the external ear canal 904 will help to avoid movement interference during EEG recording. This will allow the wearer (user) 900 to freely move around while the EEG recording is taking place.

In some embodiments, the concise (at-home) sleep monitoring system 102 may comprise a housing structure 60 which may be configured as a behind-the-ear-hearing-aid-style structure 63. Preferably, the concise sleep monitoring system 102 may comprise an EEG recording module 21 that may be housed in a housing structure 60, and the housing structure 60 may be a behind-the-ear-hearing-aid-style structure 63, the behind-the-ear-hearing-aid-style structure 63 having an in-the-ear portion 66 and a behind-the-ear portion 65. The EEG electrodes 24, 25, 26, 27, may be partially embedded in the surface 66A of the in-the-ear portion 66 with slight protrusion at the surface 66A of the in-the-ear portion 66. The EEG electrodes 24, 25, 26, 27, may be located on or placed at separate locations on the surface 66A of the in-the-ear portion 66 which can be inserted into the wearer's external ear canal 904. The in-the-ear portion 66 may comprise a flexible elastic and adaptable material (for example: ultra-soft silicone type material), and the flexible elastic and adaptable material is configured to have appropriate flexibility elasticity and adaptability such that the EEG electrodes 24, 25, 26, 27, are naturally and snugly in close contact with the skin of the external ear canal 904 of the wearer's ear 902 when the in-the-ear portion 66 is inserted into the external ear canal 904 of the wearer's ear 902. The ultra-soft silicone-type material will facilitate steady uniform and easy installation of the EEG electrodes 24, 25, 26, 27. Since the EEG electrodes 24, 25, 26, 26 are integrated and partially embedded in the surface 66A of the in-the-ear portion 65, accidental dislodgement of an individual electrode 24, 25, 26, 27 can be avoided. Being snugly filled inside the external ear canal 904 will help to avoid movement interference during EEG recording. This will allow the wearer (user) 900 to move around freely while the EEG recording is taking place.

In some embodiments, the concise (at-home) sleep monitoring system 102 may comprise a housing structure 60 which may be configured as a tubular-shaped structure 67. Preferably, the concise sleep monitoring system 102 may comprise an EEG recording module 21 that may be housed in a housing structure 60, and the housing structure 60 may be a tubular-shaped structure 67. Preferably, each EEG electrode 24, 25, 26, 27, may be partially embedded in the surface 67A of the tubular-shaped structure 67 with slight protrusion at the surface 67A of the tubular-shaped structure 67. The tubular-shaped structure 67 may comprise a flexible elastic and adaptable material (for example: soft foam or ultra-soft silicone type material, such as pacifier-grade silicone), and the flexible elastic and adaptable material may be configured to have appropriate flexibility, elasticity and adaptability such that the EEG electrodes 24, 25, 26, 27, are naturally and snugly in contact with skin of the external ear canal 904 of the wearer's ear 902 when the tubular-shaped structure 67 is inserted into the external ear canal 904 of the wearer's ear 902. The soft foam or ultra-soft silicone-type material will facilitate steady uniform and easy installation of the EEG electrodes 24, 25, 26, 27. Since the EEG electrodes 24, 25, 26, 26 are integrated and partially embedded in the surface 67A of the tubular-shaped structure 67, accidental dislodgement of an individual electrode 24, 25, 26, 27 can be avoided. Being snugly filled inside the external ear canal 904 will help to avoid movement interference during EEG recording. This will allow the wearer (user) 900 to freely move around while the EEG recording is taking place.

In some embodiments, a concise sleep monitoring system 102 may comprise a network interface 85, 406, and one or more of the following: a speaker 86, 404A, a vibrator 87, 404B and/or a display screen 89, 404C, (such as a display screen 404C on a client device 400 of the wearer 900 and/or a display screen 89 on the housing structure 60). The network interface 85, 406, may be in electronic communication with the processing unit 50, 401. A speaker 86, 404A, a vibrator 87, 404B, and/or a display screen 89, 404C may be in electronic communication with the network interface 85, 406, and processing unit 50, 401. The processing unit 50, 401 is configured to send electronic signals to the network interface 85, 406. Preferably, the network interface 85, 406 is configured to send signals (notification) to the display screen 404C which is configured to generate a visible notification (visual display) to or on a client device 400 describing the wearer's sleep profile and the wearer's EEG profile. Optionally, the network interface 85, 406, may be configured to send signals to the display screen 89 that is configured to generate a visible notification on the housing structure 60 describing the wearer's sleep profile and the wearer's EEG profile. (For example, the display screen 89 on the housing structure 60 may show very brief information to remind the wearer 900 to see more detailed information on the display screen 404C on the client device 400 of the wearer 900). When obstructive sleep apnea (OSA) is detected by the processing unit 50, 401, the processing unit 50, 401, may be configured to automatically send electronic signals to the network interface 85, 406. The network interface 85, 406, may then be configured to automatically send electronic signals to the speaker 86, 404A, to immediately generate an audible notification and/or may be configured to automatically send electronic signals to the vibrator 87, 404B, to immediately generate a tactile notification. The one or more notifications may prompt the wearer 900 to change the sleep position which often helps to alleviate or even stop the obstructive sleep apnea (OSA) (OSA is usually worse when sleeping in a supine position and usually improves when sleeping in side positions. Elevating the head while sleeping might also help improve OSA). If the wearer 900 is using a device (such as continuous positive airway pressure, [CPAP], or anti-snoring oral devices) for OSA treatment, the warning notification may prompt the wearer 900 to adjust the setting of the CPAP or the setting of anti-snoring oral device. If the CPAP or anti-snoring oral device became detached during sleep, the notification may prompt the wearer to re-attach the CPAP or re-attach the anti-snoring oral device. Optionally, when the processing unit 50, 401, detects cessation of OSA, the processing unit 50, 401, may be configured to send electronic signals to the network interface 85, 406, to stop the audible notification and/or tactile notification. As used herein, a display screen 89, 404C is a visual output device that presents information in a visible form, such as text, data, images, or graphics. A display device is a piece of hardware that presents visual or sometimes tactile information (including text, data, images, or graphics) typically generated by a computer or other electronic device. In some sense, the term "display screen" could be interchangeable as "visual display" or "display device" (although "display device" is a little bit broader term since it also includes braille display or tactile display for blind people). Display screens are found on computer monitors, smartphones, health trackers and other electronic devices. Example display screens 89, 404C, may include a Liquid crystal display (LCD), Light-emitting diode display (LED), Electroluminescent display (ELD), Electronic paper, E Ink, Plasma display panel (PDP), Cathode ray tube display (CRT), High-Performance Addressing display (HPA), Thin-film transistor display (TFT), Organic light-emitting diode display (OLED), Surface-conduction electron-emitter display (SED), Laser TV, Carbon nanotubes, Quantum dot display, Interferometric modulator display (IMOD), etc. In some embodiments, a concise sleep monitoring system 102 may be configured as a simplified sleep monitoring system that comprises an ancillary sleep surveillance system 70, and the ancillary sleep surveillance system 70 may comprise a pulse oximeter 71 that is an ear-canal pulse oximeter 71A. The simplified sleep monitoring system uses the pulse oximeter 71 or the ear-canal pulse oximeter 71A as a surrogate for sleep apnea detection.

In some embodiments, the present invention may comprise a novel auricular sleep monitoring system 106 suitable for at home use. The auricular sleep monitoring system 106 may comprise an auricular EEG monitoring system 20, an ear-canal pulse oximeter 71A and a processing unit 50, 401. The auricular EEG monitoring system 20 is as described hereinbefore. Preferably, the auricular sleep monitoring system 106 uses the ear-canal pulse oximeter 71A as a surrogate for sleep apnea detection. The ear-canal pulse oximeter 71A is configured to record the wearer's pulse data and blood oxygen saturation data. Sleep apnea (including obstructive sleep apnea, central sleep apnea or mixed sleep apnea) is usually associated with significant drop of blood oxygen saturation. As commonly accepted, normal range of blood oxygen saturation is about 95-100%, low blood oxygen saturation is about 89-92%, while dangerously low blood oxygen saturation (requiring medical attention) is about 88% or below. During very severe sleep apnea, the blood oxygen saturation could drop to as low as 70% temporarily. The ear-canal pulse oximeter 71A may be a reflectance pulse oximeter having a reflectance oximeter module 40A, and the reflectance pulse oximeter comprises a wired or wireless light generator 41, a wired or wireless light detecting sensor 42 and a detection module 45. The wired or wireless light generator 41 and the wired or wireless light detecting sensor 42 are configured to be coupled to the external ear canal 904 of the wearer's ear 92 to be in contact with the skin of the external ear canal 904 of the wearer's ear. The wired or wireless light generator 41 and the wired or wireless light detecting sensor 42 may be in electronic communication 19 (wired or wireless) with the detection module 45. The light generator 41 includes light-emitting diode configured to emit light of different wavelengths, and the light detecting sensor 42 is configured to measure the absorption of light of different wavelengths including red and infrared wavelengths. An amplifier of amplifiers and filters 43 is responsible for amplifying the weak electrical signals received from the light generator 41 and the light detecting sensor 42. Filters of amplifiers and filters 43 are used to remove unwanted noise and interference from the electrical signals before being communicated to the detection module 45. The detection module 45 is in electronic communication with the light generator 41 and the light detecting sensor 42, and the detection module 45 is configured to analyze the data transmitted from the light generator 41 and data transmitted from the light detecting sensor 42 to assess pulse data and blood oxygen saturation data of the wearer 900. The auricular EEG monitoring system 20 and the ear-canal pulse oximeter 71A are in electronic communication with a processing unit 50, 401. The processing unit 50, 401, may be configured to receive the EEG data (from auricular EEG monitoring system 20), pulse data and blood oxygen saturation data (from ear-canal pulse oximeter 71A) to assess the wearer's 900 sleep profile and the wearer's 900 pulse profile and blood oxygen saturation profile. The processing unit 50, 401, may be configured to receive the EEG data (from auricular EEG monitoring system 20), pulse data and blood oxygen saturation data (from ear-canal pulse oximeter 71A) to assess the wearer's primitive sleep profile and detect presence of blood oxygen saturation of wearer 900 dropping below a pre-determined level (suggestive of probable presence of sleep apnea). (Example of a pre-determined blood oxygen saturation level: 90%, 88%, 85% or other pre-determined levels). The primitive sleep profile may include the NREM sleep stages, including wakefulness, drowsiness, NREM-N1, NREM-N2 and NREM-N3 sleep stages, as per the EEG data. (REM sleep stage cannot be accurately assessed due to absence of EOG in this auricular sleep monitoring system 106). Preferably, the auricular sleep monitoring system 106 further comprises a network interface 85, 406, in electronic communication with the processing unit 50, 401. The network interface 85, 406, is in electronic communication with one of the following: a speaker 86, 404A, a vibrator 87, 404B, and a display screen 89, 404C (such as a display screen 89 on the housing structure 60 and/or a display screen 404C on a client device 400). When the blood oxygen saturation dropping below the pre-determined level (for example 90%, 88%, 85% or other pre-determined levels) (suggestive of probable presence of sleep apnea) is detected by the processing unit 50, 401, the processing unit 50, 401, is configured to immediately send signals to the network interface 85, 406. The network interface 85, 406, is configured to automatically send signals to the speaker 86, 404A, (that is configured to send audible notification to the wearer) or to the vibrator 87, 404B, (that is configured to send tactile notification to the wearer.) immediately to alert the wearer to take appropriate actions (appropriate actions such as changing sleep position, or adjusting CPAP or anti-snoring oral device, as described hereinbefore). The network interface 85, 406 is further configured to send signals to the display screen 89 (that is configured to generate a visible notification on the housing structure 60) and/or to the display screen 404C (that is configured to generate a visible notification on a client device 400 of the wearer 900) with description of the wearer's 900 sleep profile and presence or absence of blood oxygen saturation dropping below the pre-determined level. Preferably, the auricular sleep monitoring system 106 may be housed in one of the following: an earbud-style structure 61, an in-the-ear portion 66 of a behind-the-ear-hearing-aid-style structure 63 or a tubular-shaped structure 67, similar to housing structure 60 descriptions hereinbefore.

In some embodiments, the present invention may comprise a novel ear-canal pulse oximeter system 71A, suitable for ambulatory use. The ear-canal pulse oximeter system 71A may comprise an ear-canal pulse oximeter 71A and a processing unit 50, 401. The ear-canal pulse oximeter 71A is in wired or wireless electronic communication with the processing unit 50, 401. In some embodiments, the processing unit 50, 401 may be configured to be housed together with the ear-canal pulse oximeter 71A or be housed in a client device 400 (such as a wearable watch-type client device 400A or a portable smart-phone type client device 400B). Preferably, the ear-canal pulse oximeter 71A is configured to record the wearer's pulse data and blood oxygen saturation data. As commonly accepted, normal range of blood oxygen saturation is about 95-100%, low blood oxygen saturation is about 89-92%, while dangerously low blood oxygen saturation (requiring medical attention) is about 88% or below. During severe chronic obstructive pulmonary disease (COPD) exacerbation, the blood oxygen saturation could drop to below 88% or even lower. The ear-canal pulse oximeter 71A may be a reflectance pulse oximeter having a reflectance oximeter module 40A, and the reflectance pulse oximeter comprises a wired or wireless light generator 41, a wired or wireless light detecting sensor 42 and a detection module 45. The wired or wireless light generator 41 and the wired or wireless light detecting sensor 42 are configured to be coupled to the external ear canal 904 of the wearer's ear 92 to be in contact with the skin of the external ear canal 904 of the wearer's ear. The wired or wireless light generator 41 and the wired or wireless light detecting sensor 42 may be in electronic communication 19 (wired or wireless) with the detection module 45. The light generator 41 includes light-emitting diode configured to emit light of different wavelengths, and the light detecting sensor 42 is configured to measure the absorption of light of different wavelengths including red and infrared wavelengths. An amplifier of amplifiers and filters 43 is responsible for amplifying the weak electrical signals received from the light generator 41 and the light detecting sensor 42. Filters of amplifiers and filters 43 are used to remove unwanted noise and interference from the electrical signals before being communicated to the detection module 45. The detection module 45 is in electronic communication with the light generator 41 and the light detecting sensor 42, and the detection module 45 is configured to analyze the data transmitted from the light generator 41 and data transmitted from the light detecting sensor 42 to assess pulse data and blood oxygen saturation data of the wearer 900. The ear-canal pulse oximeter 71A is in electronic communication with the processing unit 50, 401. The processing unit 50, 401, is configured to receive the pulse data and blood oxygen saturation data (from ear-canal pulse oximeter 71A) to assess the wearer's pulse profile and blood oxygen saturation profile and to detect presence of blood oxygen saturation dropping below a pre-determined level. (Example of a pre-determined blood oxygen saturation level: 90%, 88%, 85% or other pre-determined levels). Preferably, the ear-canal pulse oximeter system 71A further comprises a network interface 85, 406, in electronic communication with the processing unit 50, 401. The network interface 85, 406, is in electronic communication with one of the following: a speaker 86, 404A, a vibrator 87, 404B, and a display screen 404C (such as a display screen 404C on a client device 400). When the blood oxygen saturation dropping below the pre-determined level (for example 90%, 88%, 85% or other pre-determined levels) is detected by the processing unit 50, 401, the processing unit 50, 401, is configured to immediately send signals to the network interface 85, 406. The network interface 85, 406, is configured to automatically send signals to the speaker 86, 404A, (that is configured to send audible notification to the wearer) or to the vibrator 87, 404B, (that is configured to send tactile notification to the wearer.) immediately to alert the wearer to take appropriate actions (For example, an appropriate action may include adjusting the oxygen output from an oxygen tank if a COPD patient carries an oxygen tank.). The network interface 85, 406 is further configured to send signals to the display screen 404C (that is configured to generate a visible notification on a client device 400 of the wearer 900) with description of the wearer's 900 pulse data and blood oxygen saturation data. Preferably, the ear-canal pulse oximeter system 71A may be housed in one of the following: an earbud-style structure 61, an in-the-ear portion 66 of a behind-the-ear-hearing-aid-style structure 63 or a tubular-shaped structure 67, similar to housing structure 60 descriptions hereinbefore.

Almost all of the conventional at-home sleep monitoring systems do not have EEG capability and thus unable to gather accurate sleep data. The concise at-home sleep monitoring system 102 of the present invention is able to solve this problem. This concise at-home sleep monitoring system 102 can be easily used at home and can be easily self-installed or self-removed, without the need of being continuously monitored by a certified technologist. The system 102 can be repeatedly used every night, and it can also be used in the daytime during wakeful time for monitoring of health conditions.

In some embodiments, the present invention may comprise a comprehensive at-home sleep monitoring system 103 that comprises an integration of the aforementioned auricular electroencephalography (EEG) monitoring system 20, the auricular electrooculogram (EOG) system 101, and an ancillary sleep surveillance system 70. In some embodiments, an ancillary sleep surveillance system 70 may comprise at least one of the following sensors or monitors: a pulse oximeter 71, a peripheral arterial tonometry (PAT) monitor 72, an airflow sensor (airflow meter) 73, an actigraphy sensor (or motion sensor) 74, a breathing monitor (respiratory inductance plethysmography (RIP) monitor) 75, a leg movement sensor 76 a body temperature sensor 77, an electromyogram (EMG) sensor (usually EMG of submental muscle [chin] and/or anterior tibialis muscle [leg]) 78, an electrocardiogram (ECG) sensor 79, a body position sensor 80, a blood pressure monitor 81, and/or any other body parameter measuring sensor. Optionally, a comprehensive at-home sleep monitoring system 103 may also comprise an auricular electrocardiogram (ECG) system 30 to gather data of wearer's heart rate and heart rhythm and other cardiac conditions. The comprehensive at-home sleep monitoring system 103 further comprises a processing unit 50, 401. The processing unit 50, 401, may be in electronic communication with the auricular EEG monitoring system 20, the auricular EOG system 101, and the auricular ECG system 30. The processing unit 50, 401, may also be in electronic communication with each comprising sensor or monitor of the ancillary sleep surveillance system 70, (The ancillary sleep surveillance system 70 comprises at least one of the following: pulse oximeter 71, peripheral arterial tonometer (PAT) monitor 72, airflow sensor 73, actigraphy sensor (motion sensor) 74, breathing monitor (respiratory inductance plethysmography (RIP) monitor) 75, leg movement sensor 76, EMG sensor 78, body temperature sensor 77, blood pressure monitor 81 and body position sensor 80.) The processing unit 50, 401, may be configured to analyze the data collected by the auricular EEG monitoring system 20, auricular EOG system 101, auricular ECG system 30, and data collected from each comprising sensor or monitor of the ancillary sleep surveillance system 70. With these data, using sleep analysis algorithms, the processing unit 50, 401, may be further configured to assess the wearer's sleep profile. The sleep profile may include detailed sleep architecture, sleep stages, sleep latency, duration of each sleep stage, sleep quality, sleep density, presence of obstructive sleep apnea and presence of central sleep apnea. The sleep profile preferably also includes Apnea-Hypopnea Index (AHI) score. The AHI score can be used to classify the severity of sleep apnea. With the help of sleep analysis algorithms, the processing unit 50, 401, may be further configured to detect presence of sleep disorders, which may include narcolepsy, restless leg syndrome, periodic limb movement disorder, REM sleep behavior disorder, parasomnias and insomnia.

Preferably, this comprehensive at-home sleep monitoring system 103 may be housed in a housing structure 60 that may be an earbud style structure 61 (earbud or airpod-like structure) or a tubular-shaped structure 67. Alternatively, this comprehensive at-home sleep monitoring system 103 may be housed in a housing structure 60 that may be an in-the-ear portion 66 of a structure adapted from a behind-the-ear-hearing-aid-style structure 63. The comprehensive sleep monitoring system 103 can monitor nearly all of the important parameters in sleep studies, similar to a polysomnogram (PSG). While PSG is usually done in a sleep center or a medical facility, this comprehensive at-home sleep monitoring system 103 can be easily used at home and can be easily self-installed or self-removed by the wearer 900, without the need of being continuously monitored by a certified technologist. This system 103 can be repeatedly used every night for sleep monitoring. Some of the components (wearable components such as auricular EEG monitoring system 20, auricular EOG system 101, auricular ECG system 30, ear-canal pulse oximeter 71A etc.) can also be used in the daytime during wakeful time for monitoring of the wearer's health profiles, including the EEG profile, EOG profile, ECG profile and pulse profile and blood oxygen saturation profile. For example, combination of auricular EEG monitoring system 20 and auricular ECG system 30 is wearable and can be easily used in the daytime for monitoring of health conditions. Combination of auricular EEG monitoring system 20, ear-canal pulse oximeter 71A, auricular ECG system 30, and auricular EOG system 101 is also wearable and can be easily used in daytime or nighttime. These fully wearable components (and combination thereof) are very convenient and suitable for daytime use for monitoring of health conditions since the wearer can be freely ambulatory. The auricular EEG monitoring system 20 and auricular EOG system 101 may also be combined and used in industries (for example robotics and gaming industries) to guide brain-computer interface.

This comprehensive at-home sleep monitoring system 103 preferably further comprises a network interface 85, 406, and one or more of the following: a speaker 86, 404A, a vibrator 87, 404B, and/or a display screen 404C, 89 (e.g. a display screen 404C on a client device 400 of the wearer 900 and/or a display screen 89 on the housing structure 60). The network interface 85, 406, may be in electronic communication with the processing unit 50, 401. The speaker 86, 404A, vibrator 87, 404B and/or the display screen 89, 404C are in electronic communication with the network interface 85, 406. The processing unit 50, 401, is configured to send electronic signals to the network interface 85, 406. Preferably, the network interface 85, 406, is configured to send signals (notification) to the display screen 404C which is configured to generate a visual display on client device 400 of the wearer 900 describing the wearer's sleep profile and wearer's EOG profile, EEG profile, ECG profile, pulse data and blood oxygen saturation data. Optionally, the network interface 85, 406, is configured to send signals to the display screen 89, and the display screen 89 is configured to generate a visible notification on the housing structure 60 describing the wearer's sleep profile and wearer's EOG profile, EEG profile, ECG profile, pulse data and blood oxygen saturation data. (For example, the display screen 89 on the housing structure 60 may show very brief information to remind the wearer 900 to see more detailed information on the display screen 404C on the client device 400 of the wearer 900). When obstructive sleep apnea is detected by the processing unit 50, 401, the processing unit 50, 401 is configured to automatically send electronic signals to the network interface 85, 406 immediately. The network interface 85, 406, is configured to automatically send electronic signals to the speaker 86, 404A, to start audible notification immediately and/or to automatically send electronic signals to the vibrator 87, 404B, to start tactile notification immediately. The notifications (warnings) may prompt the wearer 900 to change the sleep position or elevate the head to alleviate (or even stop) the obstructive sleep apnea (OSA). If the wearer 900 is using a device (such as continuous positive airway pressure or CPAP) for OSA treatment, the warning may prompt the wearer to adjust the settings of the CPAP or to re-attach the CPAP if the CPAP became detached during sleep. If the wearer is using an anti-snoring oral device for obstructive sleep apnea (OSA) treatment, the warning may prompt the wearer to adjust the setting of the anti-snoring oral device. Optionally, when the processing unit 50, 401, detects cessation of OSA, the processing unit 50, 401, may be configured to send electronic signals to the network interface 85, 406, to stop audible notification and/or tactile notification.

Figure 6:
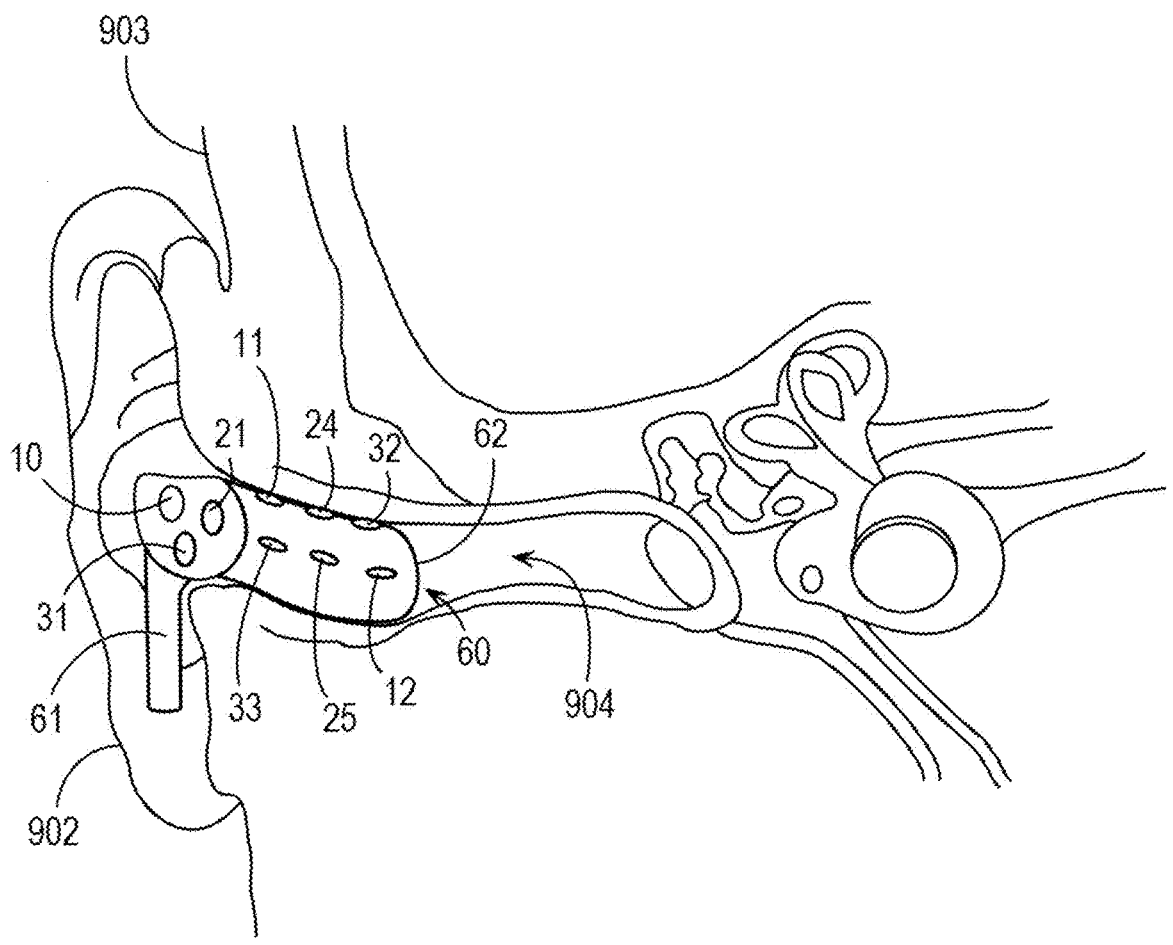
FIG. 6-FIG. 6 shows a perspective view of a housing structure coupled to an ear of a wearer and configured as an earbud style structure housing an EOG recording module, an auricular EEG recording module, and an auricular ECG recording module according to various embodiments described herein.

The earbud-style structure 61 would be particularly preferred as a housing structure 60 for the auricular EEG monitoring system 20, auricular ECG system 30, and auricular EOG system 101. All of the EEG electrodes 24, 25, 26, 27, ECG electrodes 32, 33, and EOG electrodes 11, 12, are partially embedded in the surface 62A of the horizontal portion 62 with slight protrusion at the surface 62A of the horizontal portion 62 of the earbud-style structure 61. (FIG. 6). Preferably, the horizontal portion 62 of the earbud-style structure 61 is configured to be made with elastic flexible and adaptable material (for example soft foam or ultra-soft silicone material, such as pacifier-grade silicone). The material of the horizontal portion 62 of the earbud-style structure 61 is configured to have appropriate elasticity, flexibility and adaptability such that when the horizontal portion 62 of the earbud-style structure 61 is inserted into a wearer's external ear canal 904, the horizontal portion 62 of the earbud-style structure 61 will naturally adapt to the contour of wearer's external ear canal 904 and will snugly fill the interior of the wearer's external ear canal 904. This set-up of electrodes 11, 12, 24, 25, 26, 27, 32, 33, being partially embedded with slight protrusion at the surface 62A and the flexibility, elasticity and adaptability of the material will allow all of these electrodes 11, 12, 24, 25, 26, 27, 32, 33, to be naturally and snugly in close contact with the skin of the wearer's external ear canal 904 and also allow very easy self-installation and self-removal. Installing and removing these electrodes 11, 12, 24, 25, 26, 27, 32, 33, will be as easy as inserting and removing the earbud-style structure 61 from the wearer's external ear canal 904. There will be no need for a certified technologist to install the electrodes 11, 12, 24, 25, 26, 27, 32, 33. Applying adhesive material to secure these electrodes 11, 12, 24, 25, 26, 27, 32, 33, will also be unnecessary. This is feasible due to the unique anatomical features of the human external ear canal 904. This will provide a huge convenience for the user. The soft foam or ultra-soft silicone-type material will facilitate steady uniform and easy installation of the EOG, EEG and ECG electrodes 11, 12, 24, 25, 26, 27, 32, 33. Since these electrodes 11, 12, 24, 25, 26, 26, 32, 33 are partially embedded in the surface 62A (with slight protrusion at the surface 62A) of the horizontal portion 62 of the earbud-style structure 61, accidental dislodgement of an individual electrode 11, 12, 24, 25, 26, 27, 32, 33 can be avoided. Being snugly filled inside the external ear canal 904 will help to avoid movement interference during EOG, EEG and ECG recordings. This will allow the wearer (user) 900 to freely move around while the EOG, EEG, ECG recordings are taking place.

Figure 7:
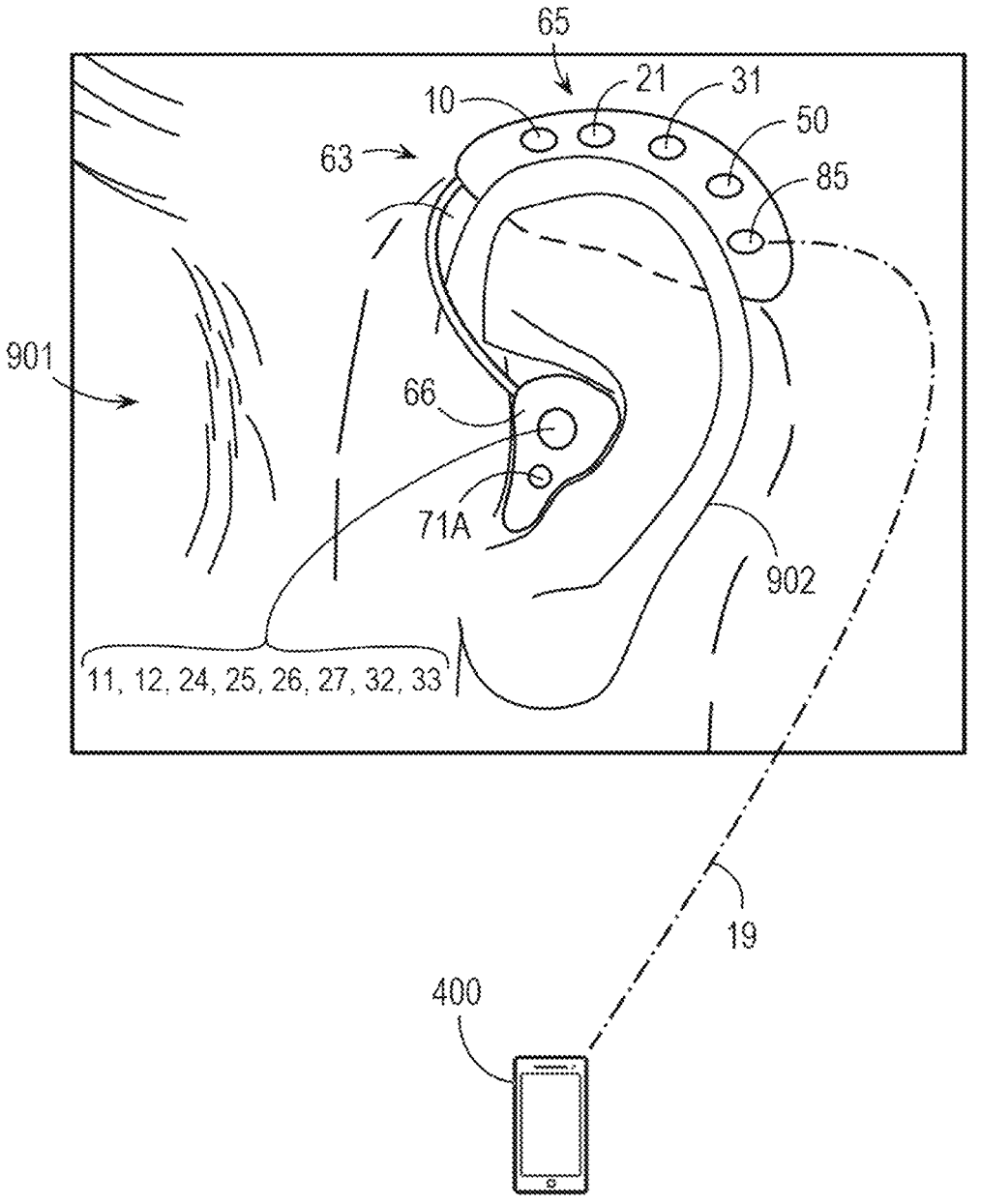
FIG. 7-FIG. 7 depicts a perspective view of a housing structure coupled to an ear of a wearer and configured as a behind-the-ear-hearing-aid-style structure housing an EOG recording module, an auricular EEG recording module, an auricular ECG recording module and an ear-canal pulse oximeter according to various embodiments described herein.
Figure 8:
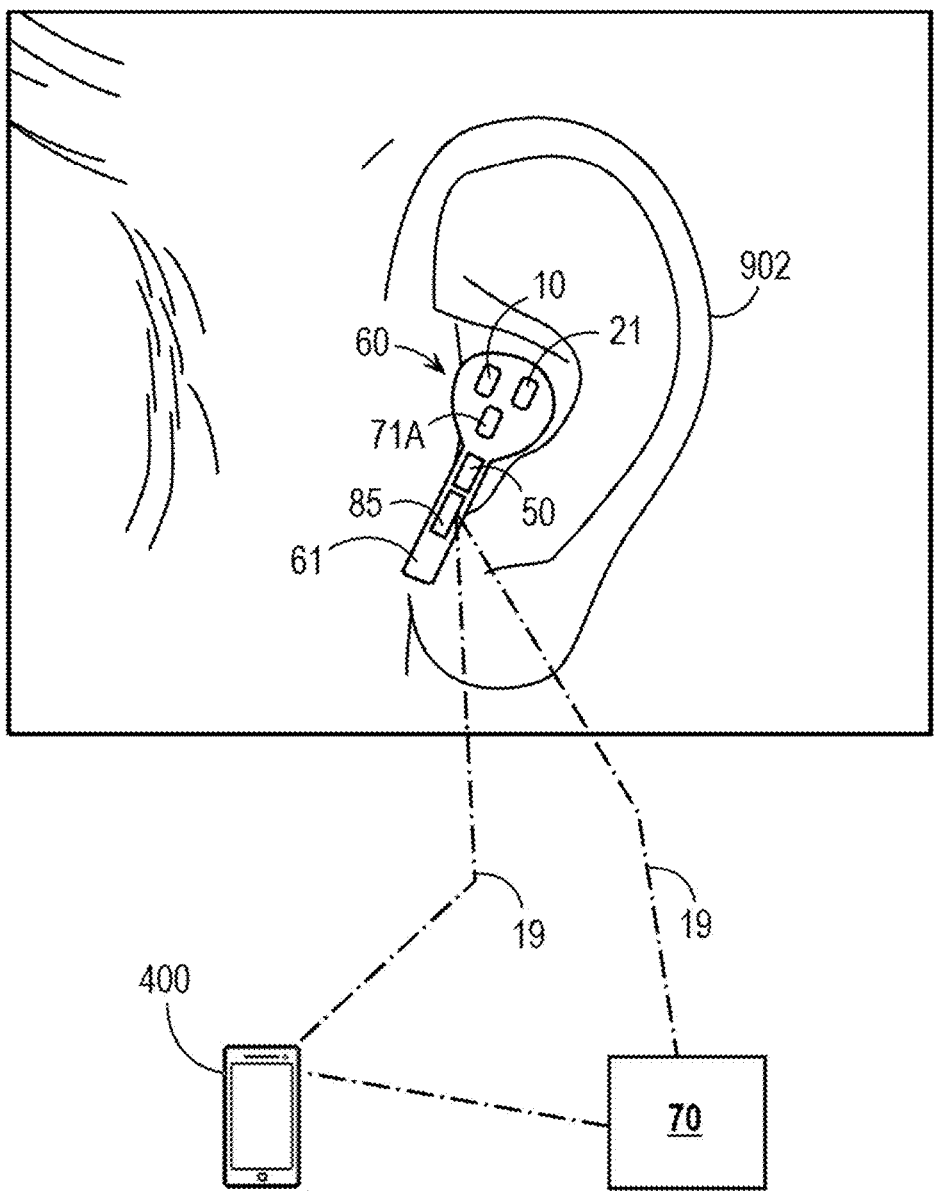
FIG. 8-FIG. 8 illustrates a perspective view of a housing structure of an at-home sleep monitoring system coupled to an ear of a wearer and configured as an earbud style structure housing an EOG recording module, an EEG recording module, and an ear-canal pulse oximeter according to various embodiments described herein.
Figure 18:
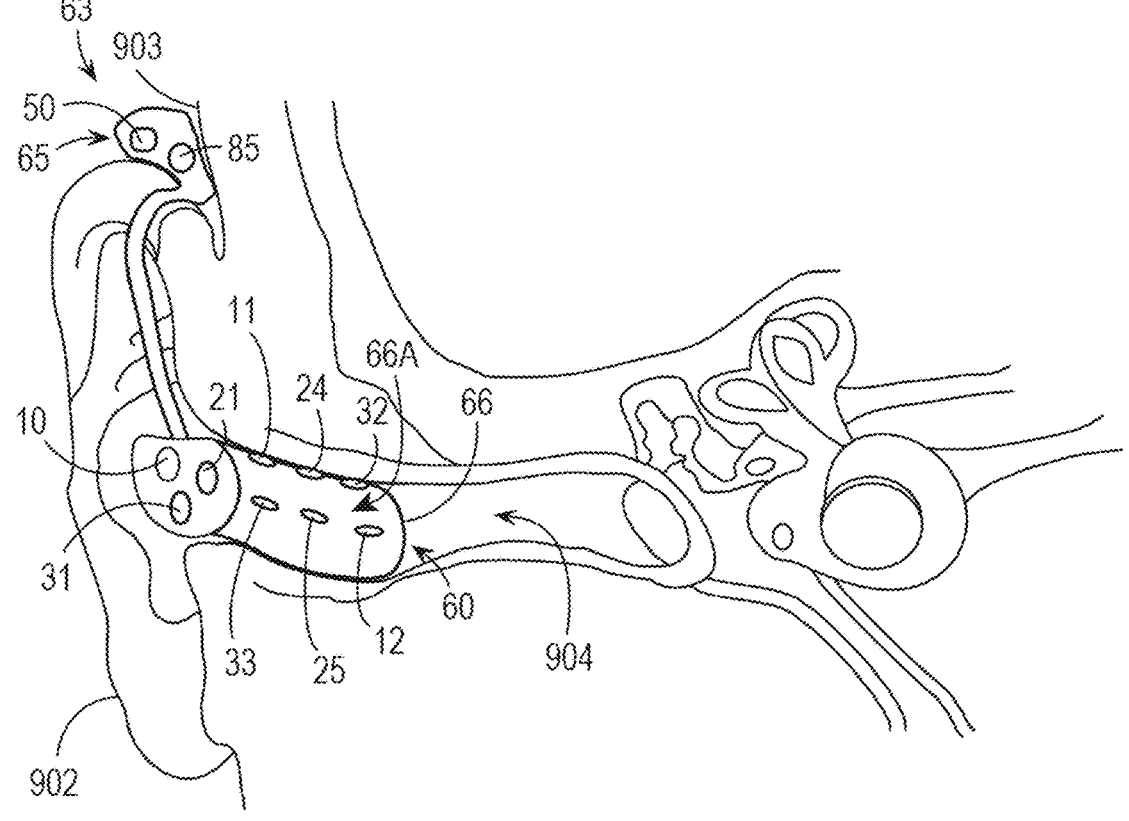
FIG. 18-FIG. 18 shows a perspective view of a housing structure coupled to an ear of a wearer and configured as a behind-the-ear-hearing-aid-style structure housing an EOG recording module, an auricular EEG recording module, and an auricular ECG recording module according to various embodiments described herein.
Figure 19:
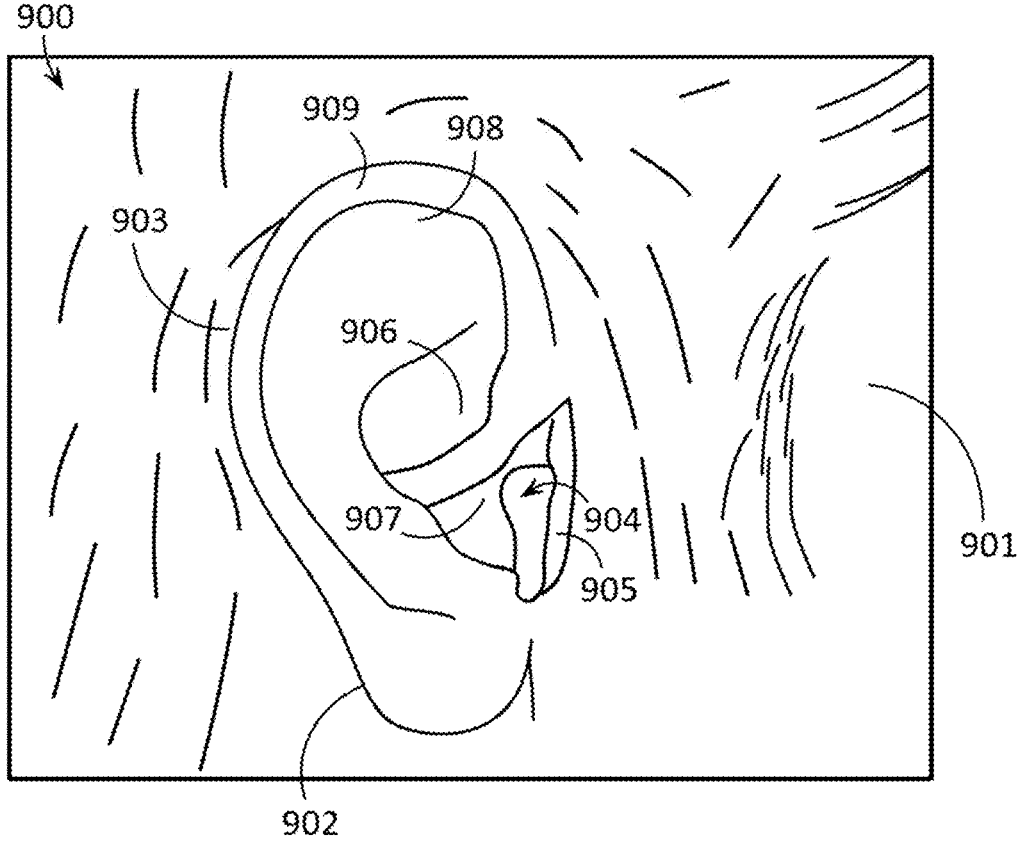
FIG. 19-FIG. 19 depicts a perspective view of a portion of a head of a wearer and areas on the ear and head of the wearer.

These advantages can be similarly achieved when using a housing structure 60 that comprises a behind-the-ear-hearing-aid-style structure 63. The EEG electrodes 24, 25, 26, 27, ECG electrodes 32, 33, and EOG electrodes 11, 12, are preferably housed within the in-the-ear portion 66 of a behind-the-ear-hearing-aid-style structure 63. (FIGS. 7, 18). The in-the-ear portion 66 is configured to be made with elastic flexible and adaptable material (for example: soft foam or ultra-soft silicone type material). The elastic flexible and adaptable material of the in-the-ear portion 66 is configured to have appropriate elasticity, flexibility and adaptability such that it will naturally adapt to the contour of the wearer's external ear canal 904 and snugly fill the interior of the wearer's external ear canal 904 when it is inserted into the wearer's external ear canal 904. All of the electrodes 11, 12, 24, 25, 26, 27, 32, 33, may be partially embedded in the surface 66A of the in-the-ear portion 66 with slight protrusion at the surface 66A of the in-the-ear portion 66 so that all of these electrodes 11, 12, 24, 25, 26, 27, 32, 33, will be naturally and snugly in contact with the skin of the wearer's external ear canal 904. Installing and removing these electrodes 11, 12, 24, 25, 26, 27, 32, 33, will be as easy as inserting and removing the in-the-ear portion 66 from the wearer's external ear canal 904. There will be no need for a certified technologist to apply the electrodes 11, 12, 24, 25, 26, 27, 32, 33. Applying adhesive material to secure these electrodes 11, 12, 24, 25, 26, 27, 32, 33, will be unnecessary. The soft foam or ultra-soft silicone-type material will facilitate steady uniform and easy installation of the EOG EEG and ECG electrodes 11, 12, 24, 25, 26, 27, 32, 33. Since these electrodes 11, 12, 24, 25, 26, 26, 32, 33 are partially embedded in the surface 66A (with slight protrusion at the surface 66A) of the in-the-ear portion 66, accidental dislodgement of an individual electrode 11, 12, 24, 25, 26, 27, 32, 33 can be avoided. Being snugly filled inside the external ear canal 904 will help to avoid movement interference during EOG, EEG and ECG recordings. This will allow the wearer (user) 900 to move around freely while the EOG, EEG, ECG recordings are taking place.

Figure 17:
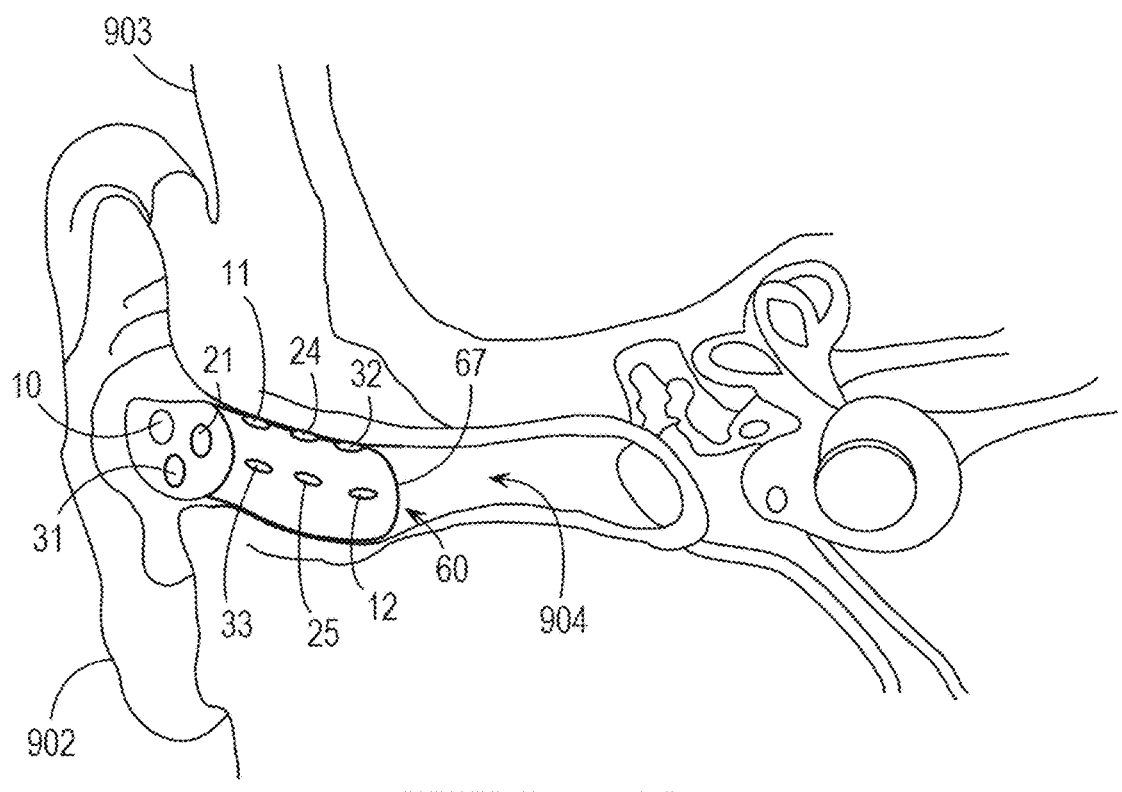
FIG. 17-FIG. 17 illustrates a perspective view of a housing structure coupled to an ear of a wearer and configured as a tubular-shaped structure housing an EOG recording module, an auricular EEG recording module, and an auricular ECG recording module according to various embodiments described herein.

In preferred embodiments, all of the EEG electrodes 24, 25, 26, 27, ECG electrodes 32, 33, and EOG electrodes 11, 12, of the comprehensive at-home sleep monitoring system 103 may be housed in a tubular-shaped structure 67. (FIGS. 16, 17). The tubular-shaped structure 67 is configured to be made from elastic flexible and adaptable material (such as soft foam or ultra-soft silicone-type material). The elastic flexible and adaptable material of the tubular-shaped structure 67 is configured to have appropriate elasticity, flexibility and adaptability such that it will naturally adapt to the contour of the wearer's external ear canal 904 and snugly fill the interior of the wearer's external ear canal 904 when the tubular-shaped structure 67 is inserted into the wearer's external ear canal 904. All of the electrodes 11, 12, 24, 25, 26, 27, 32, 33, are configured to be partially embedded in the surface 67A of the tubular-shaped structure 67 with slight protrusion at the surface 67A of the tubular-shaped structure 67, such that all of these electrodes 11, 12, 24, 25, 26, 27, 32, 33, will be naturally and snugly in contact with the skin of the wearer's external ear canal 904. Installing and removing these electrodes 11, 12, 24, 25, 26, 27, 32, 33, will be as easy as inserting and removing the tubular-shaped structure 67 from the wearer's external ear canal 904. There will be no need for a certified technologist to apply the electrodes 11, 12, 24, 25, 26, 27, 32, 33. Applying adhesive material to secure these electrodes 11, 12, 24, 25, 26, 27, 32, 33, will be unnecessary. The soft foam or ultra-soft silicone-type material will facilitate steady uniform and easy installation of the EOG, EEG and ECG electrodes 11, 12, 24, 25, 26, 27, 32, 33. Since these electrodes 11, 12, 24, 25, 26, 26, 32, 33 are partially embedded in the surface 67A (with slight protrusion at the surface 67A) of the tubular-shaped structure 67, accidental dislodgement of an individual electrode 11, 12, 24, 25, 26, 27, 32, 33 can be avoided. Being snugly filled inside the external ear canal 904 will help to avoid movement interference during EOG, EEG and ECG recordings. This will allow the wearer (user) 900 to move around freely while the EOG, EEG, ECG recordings are taking place.

In preferred embodiments, the comprehensive at-home sleep monitoring system 103 may be configured to be housed in a tubular-shaped structure 67, and all of the electrodes 11, 12, 24, 25, 26, 27, 32, 33, are housed in the tubular-shaped structure 67 and are configured to be located at the surface 67A of the tubular-shaped structure 67. In preferred embodiments, one or more of the electrodes 11, 12, 24, 25, 26, 27, 32, 33, is/are configured to be located at the upper surface 91 (upper surface 91 at approximately 90 degrees above horizontal level 92) of the tubular-shaped structure 67. (The horizontal level 92 being perpendicular to the direction of gravity.) (FIGS. 16, 17). In preferred embodiments, one or more of the electrodes 11, 12, 24, 25, 26, 27, 32, 33, is/are configured to be located at between 0 and 60 degrees, and more preferably at approximately 30 degrees (plus or minus 30 degrees) above the horizontal level 92 of the tubular structure 67 and is/are configured to face forward-upward direction 93. In preferred embodiments, one or more of the electrodes 11, 12, 24, 25, 26, 27, 32, 33, is/are configured to be located at approximately between 120 and 180 degrees, and more preferably at approximately 150 degrees (plus or minus 30 degrees) above the horizontal level 92 of the tubular structure 67 and is/are configured to face backward-upward direction 94. (Upper surface 91, horizontal level 92, forward, backward, upward, forward-upward direction 93, backward-upward direction 94, all refer to directions relative to the head 901 of the wearer 900 with the wearer 900 is in an upright position after the tubular-shaped structure 67 has been inserted into a wearer's external ear canal 904.)

Earbuds or in-the-ear pieces specially designed for sleep have been known in the art. With elastic flexible and adaptable materials (ultra-soft materials, such as foam or pacifier-grade silicone), these sleep-friendly designs provide comfort during sleep, including side sleeping position. The designs also ensure staying in place throughout the night. Examples for wireless sleep-friendly earbuds include Soundcore Sleep A20 by Anker Sleep Earbuds (Ontario, California), Google Pixel Buds Pro wireless (Mountain View, California) and Bose Sleepbuds 2 or 3 (Framingham, Massachusetts). Ear wax (cerumen) repellant earbuds are also known in the art. By using hydrophobic materials, such as silicone or nano-coatings, these earbuds can help decrease earwax from accumulating.

Figure 13:
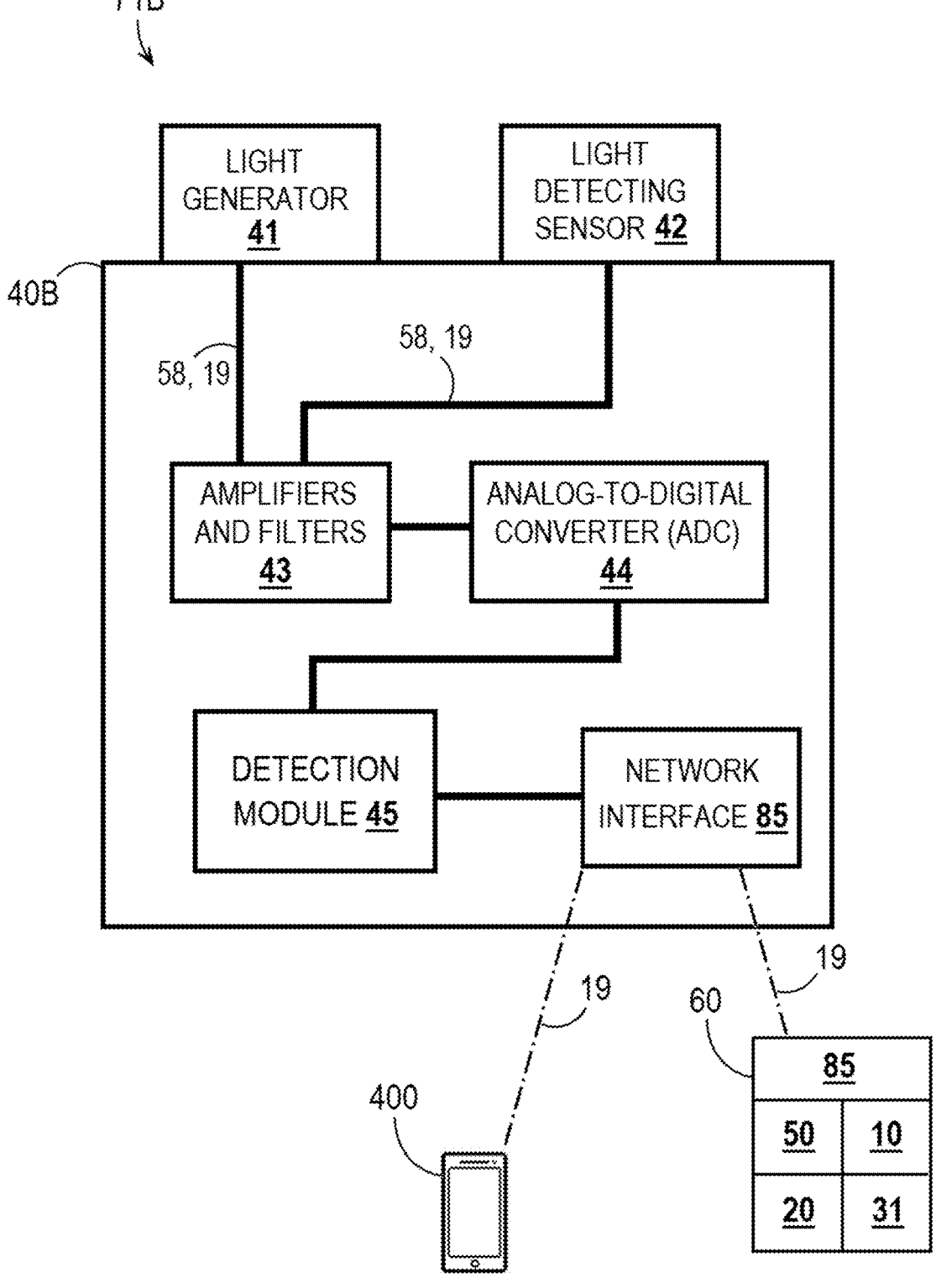
FIG. 13-FIG. 13 depicts a block diagram of an example of a transmittance pulse oximeter having a transmittance oximeter module according to various embodiments described herein.
Figure 14:
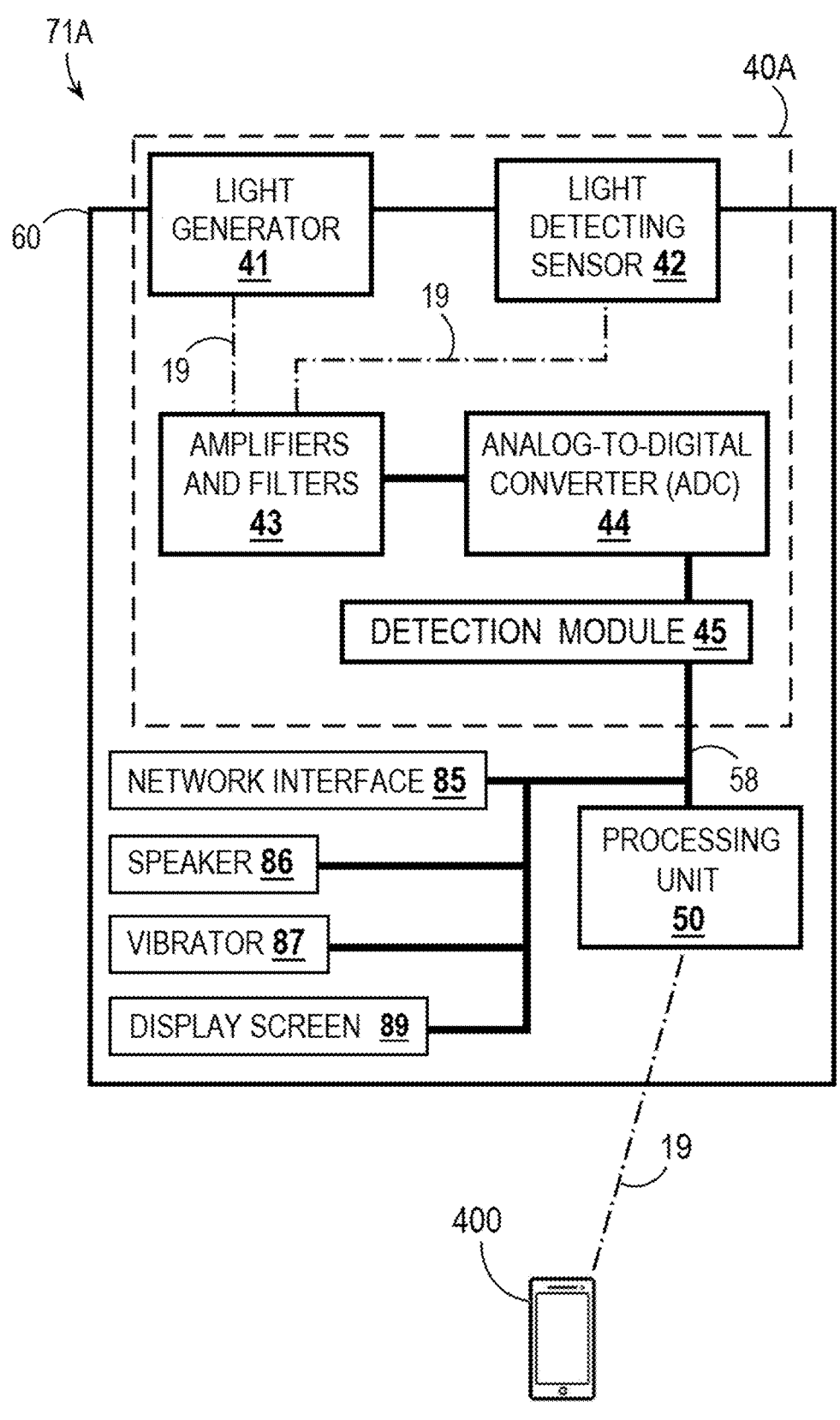
FIG. 14-FIG. 14 illustrates a block diagram of an example of a reflectance pulse oximeter having a reflectance oximeter module housed in a housing structure according to various embodiments described herein.
Figure 15:
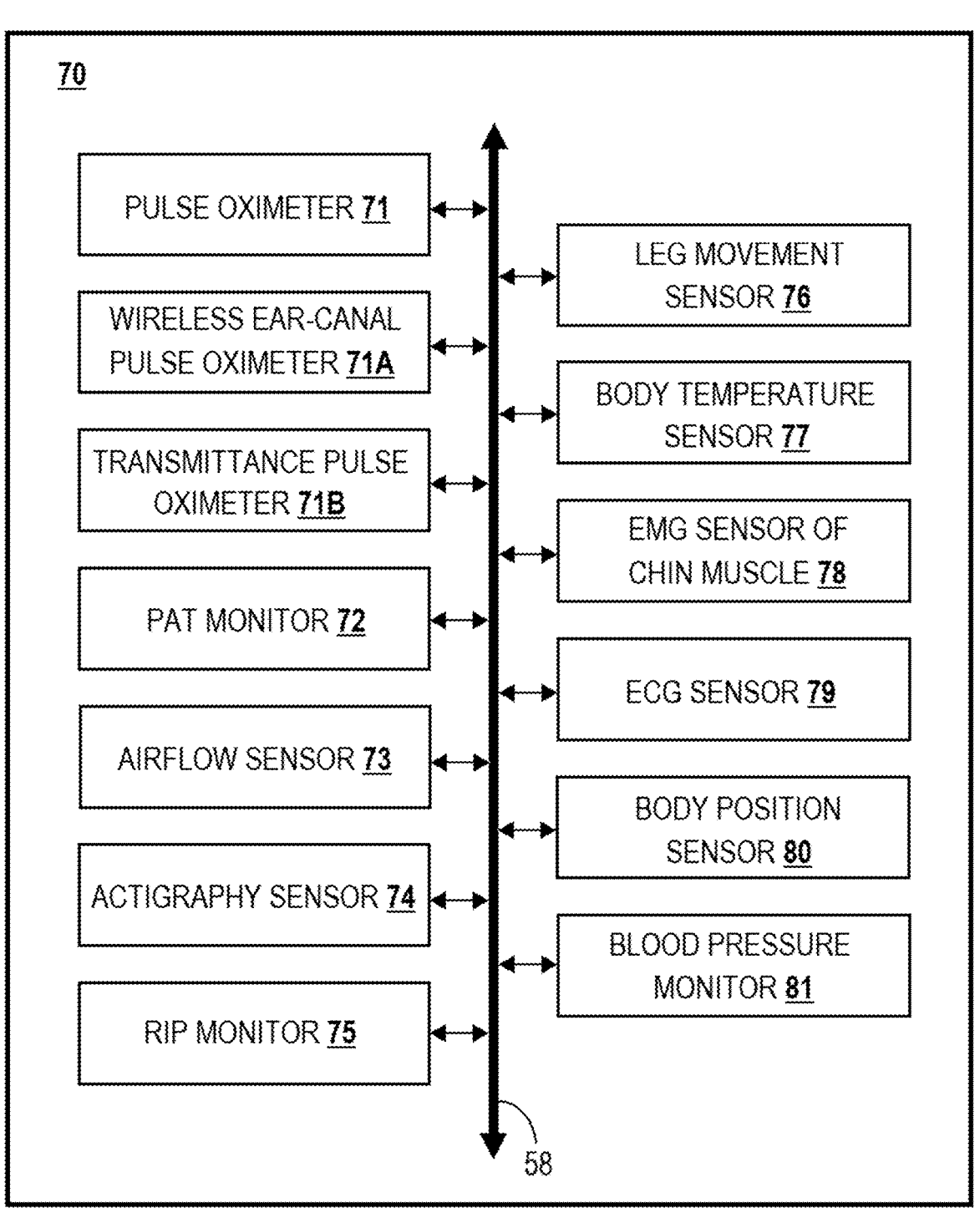
FIG. 15-FIG. 15 shows a block diagram of an example of an ancillary sleep surveillance system having one or more sensors and/or monitors according to various embodiments described herein.

The most common pulse oximeters are transmittance (transmissive mode) pulse oximeters and they are usually worn on a thin body part like finger, toe or earlobe (lobule of ear). For the present invention, the pulse oximeter 71 may be a transmittance pulse oximeter 71B worn on the finger, toe, or earlobe, and the pulse oximeter 71 may be in electronic communication with the processing unit 50, 401. (FIG. 13). Alternatively, a reflectance (reflective-mode) pulse oximeter may be incorporated into an earbud-style structure 61, a behind-the-ear-hearing-aid-style structure 63 or a tubular-shaped structure 67 forming an ear-canal pulse oximeter 71A. (FIGS. 2, 3, 14). A novel ear-canal pulse oximeter 71A can be provided by incorporating a reflectance pulse oximeter into an earbud-style structure 61 or an in-the-ear portion 66 of a behind-the-ear-hearing-aid-style structure 63 or a tubular-shaped structure 67. The ear-canal pulse oximeter 71A includes a reflectance oximeter module 40A. The reflectance oximeter module 40A is in wired (via local interface 58) or wireless electronic communication 19 with a wired or wireless light generator 41 and a wired or wireless light detecting sensor 42. (Examples for wireless pulse oximeters currently available: Wireless pulse oximeters from Turner Medical, Colchester, Connecticut; or Nonin wireless pulse oximeter from Nonin Medical Inc. Plymouth, Minnesota.) The light generator 41 and the light detecting sensor (photodiode) 42 are configured to be coupled to the wearer's external ear canal 904 and may be configured to be housed in a horizontal portion 62 of an earbud-style structure 61 or in an in-the-ear portion 66 of a behind-the-ear-hearing-aid-style structure 63 or a tubular-shaped structure 67. The light generator 41 and the light detecting sensor 42 are configured to be located on the surface 62A of the horizontal portion 62 of the earbud-style structure 61 or on the surface 66A of the in-the-ear portion 66 of a behind-the-ear-hearing-aid-style structure 63 or on the surface 67A of the tubular-shaped structure 67. The horizontal portion 62 of the earbud-style structure 61 or the in-the-ear portion 66 of the behind-the-ear-hearing-aid-style structure 63 or the tubular-shaped structure 67 is configured to be made with flexible elastic and adaptable material (e.g., ultra-soft silicone material). The flexible elastic and adaptable material is configured to have appropriate flexibility, elasticity and adaptability such that the light generator 41 and light detecting sensor 42 of the ear-canal pulse oximeter 71A will be naturally in close contact with the skin of the wearer's external ear canal 904 when the horizontal portion 62 of the earbud-style structure 61 or the in-the-ear portion 66 of the behind-the-ear-hearing-aid-style structure 63 or the tubular-shaped structure 67 is inserted into the wearer's external ear canal 904. (FIGS. 2, 3). The ear-canal pulse oximeter 71A may be configured to be in wireless and/or wired electronic communication with a processing unit 50, 401. The processing unit 50, 401 may analyze the data transmitted from the light generator 41 and the light detecting sensor 42 to assess the wearer's pulse data and blood oxygen saturation data. Ear-canal pulse oximeter 71A is one of the novel features of the present invention. Utilizing an ear-canal pulse oximeter (preferably incorporated with auricular EEG recording module 21) can save the users one less device to install and one less device to interfere with sleep when undergoing sleep studies. The ear-canal pulse oximeter 71A is easier to use because no clip or wrist band or adhesive material is needed to attach or secure the pulse oximeter. This will provide a lot of convenience for the wearer (user). A user 900 of this ear-canal pulse oximeter 71A can be fully ambulatory and this provides significant advantage when used in non-sleeping hours for health monitoring. Unlike the conventional fingertip pulse oximeter, this ear-canal pulse oximeter 71A will not hinder finger-hand functions. This ear-canal pulse oximeter 71A is also better than conventional wrist-based (like Apple Watch series 6 or later) pulse oximeters. The accuracy of conventional wrist-based pulse oximeter is often influenced by difficulty to maintain a constant and uniform fitting of the watch band. Movements of the user's arm often affect the accuracy. Potential inaccuracies are also a problem for Apple Watch pulse oximeter readings below 90%. These problems will be solved by the ear-canal pulse oximeter 71A because the soft foam or ultra-soft silicone-type material can facilitate steady uniform mounting (installation) and being snugly filled inside the external ear canal 904 can easily avoid movement interference.

Since the human external ear canal 904 is a small space, miniature electrodes will be used for the EEG electrodes 24, 25, 26, 27, ECG electrodes 32, 33, and EOG electrodes 11, 12. Sharing of the electrodes 11, 12, 24, 25, 26, 27, 32, 33, will further help to save space. At least two of the electrodes 11, 12, 24, 25, 26, 27, 32, 33, may be used or shared by an auricular EEG monitoring system 20, an auricular EOG system 101, and/or an auricular ECG system 30. For example, for wired electrodes, two wires of a local interface 58 may connect these two shared electrodes 11, 12, 24, 25, 26, 27, 32, 33, to the EEG recording module 21, while two different wires of a local interface 58 may connect these two shared electrodes 11, 12, 24, 25, 26, 27, 32, 33, to the EOG recording module 10 and two other wires of a local interface 58 may connect these two shared electrodes 11, 12, 24, 25, 26, 27, 32, 33, to the ECG recording module 31. Alternatively, for wireless electrodes, two shared wireless electrodes 11, 12, 24, 25, 26, 27, 32, 33 may be wirelessly connected with a wireless EEG amplifier 22, a wireless EOG amplifier 13 and a wireless ECG amplifier 34. Thus, two shared electrodes 11, 12, 24, 25, 26, 27, 32, 33, may be shared with the EEG 21, EOG 10, and ECG 31 recording modules. Different amplifiers and different filters 13, 22, 34, may be used by the EOG recording module 10, the EEG recording module 21, and the ECG recording module 31 to obtain EEG data, EOG data and ECG data from these two shared electrodes 11, 12, 24, 25, 26, 27, 32, 33. Two electrodes 11, 12, 24, 25, 26, 27, 32, 33, are needed for a single-lead ECG data recording although more electrodes are needed for multi-lead ECG data recording. Two electrodes 11, 12, 24, 25, 26, 27, 32, 33, are needed for usual EOG data recording by the EOG recording module 10 although more than two EOG electrodes may help to enhance the accuracy or to detect specific types of extra-ocular movements. The EEG recording module 21 may be in wired or wireless electronic communication 19 with at least two electrodes 11, 12, 24, 25, 26, 27, 32, 33, but preferably more than two electrodes for EEG data recording. Alternatively, the EEG recording module 21 may be in wired or wireless electronic communication 19 with multiple electrodes 24, 25, 26, 27, to provide multi-channel EEG data recording. Since the earbud-style structure 61 must be of small size in order to be inserted into the external ear canal 904, the EEG 21, ECG 31, and EOG 10 recording modules sharing two electrodes 11, 12, 24, 25, 26, 27, 32, 33, would help to save space.

The amplifier of amplifiers and filters 13 used for EOG recording module 10 is different from amplifier of EEG amplifiers and filters 22 and amplifier of ECG amplifiers and filters 34. There are well-established EOG, EEG and ECG amplifiers available, including wireless amplifiers, such as:

EOG Electrooculogram Smart Amplifier (Part #: EOG100D), or BioNomadix 2Ch Wireless EOG Amplifier (Part #BN-EOG2), both are available from BIOPAC Systems, Inc. (Goleta, California).

EEG Electroencephalogram Smart Amplifier (Part #: EEG100D), or BioNomadix 2Ch Wireless EEG Amplifier (Part #: BN-EEG2), both are available from BIOPAC Systems, Inc. (Goleta, California).

ECG Electrocardiogram Smart Amplifier (Part #ECG100D), or BioNomadix 2Ch Wireless ECG Amplifier (Part #BN-ECG2). Both are also available from BIOPAC Systems, Inc. (Goleta, California).

By incorporating an auricular EEG monitoring system 20 and an auricular EOG system 101 into a sleep monitoring system the present invention provides a comprehensive at-home sleep monitoring system 103 with similar parameters as polysomnogram (PSG). It is convenient and easy for a wearer 900 to use at home, like the conventional at-home sleep studies. It is more accurate and can gather more detailed sleep profile data than the conventional at-home sleep monitoring systems. It is also better than PSG because it does not require sleeping in a sleep center or a medical facility, does not require presence of licensed technologist and is much less expensive. It can be repeatedly used every night and thus is suitable for monitoring purpose. Since sleep apnea is a long-term problem, these at-home sleep monitoring systems 102, 103, of the present invention, being suitable for long-term repeated use, will offer major advantages. Another advantage is that it can automatically notify the wearer 900 immediately when obstructive sleep apnea (OSA) is detected to prompt the wearer 900 to take action, such as changing sleep position or elevating the head 901 to alleviate or stop the OSA. If the wearer 900 is using any device (such as continuous positive airway pressure or CPAP) to treat OSA, the warning can alert the wearer 900 to adjust the setting of the CPAP device or to re-attach the CPAP if the CPAP became detached during sleep. Similarly, if the wearer 900 is using an anti-snoring oral device for OSA, the warning can prompt the wearer 900 to adjust the setting of the anti-snoring oral device or to re-attach the device if the device became detached during sleep.

In sleep apnea evaluation and diagnosis, it is important to score the patient's Apnea-Hypopnea Index (AHI) score. By definition, an apnea event is when the patient stops breathing or has reduced breathing to about 10% for 10 seconds or longer. A hypopnea event is when the patient constricts breathing by over 30% for 10 seconds or longer. The AHI score is the average number of times of these two events per hour of sleep. For adults, less than 5 events per hour is normal; for children, less than one event per hour is normal. For adults, the severity of sleep apnea is determined by the following AHI scores: Mild: 5 to 14, Moderate: 15 to 29, Severe: 30+. With availability of EEG, polysomnogram can assess the accurate sleep time and thus can arrive at accurate AHI scores. Most conventional at-home sleep studies do not have EEG and usually use total recorded time or inactivity time, rather than actual sleep time, to calculate the AHI score. Because of this, the conventional at-home sleep studies often underestimate the severity of sleep apnea. By incorporating an auricular EEG monitoring system 20 into the at-home sleep monitoring systems 102, 103, of the present invention, these at-home sleep monitoring systems 102, 103, can achieve much higher accuracy since actual sleep time can be determined, rather than using the total recorded time or inactivity time as surrogate.

In some embodiments, a separate client device 400 may be used for housing of some of the components of the present invention. For example, an EEG recording module 21, an EOG recording module 10, an ECG recording module 31, and/or the processing unit 50, 401 may be housed in a wearable or portable client device 400, such as a wearable watch-type structure 400A or a portable smart-phone-type structure 400B. Wireless EEG electrodes 24, 25, 26, 27, wireless EOG electrodes 11, 12, and wireless ECG electrodes 32, 33, may be housed in one of the following: a horizontal portion 62 of an earbud-type structure 61, an in-the-ear portion 66 of a behind-the-ear-hearing-aid-style structure 63, and a tubular-shaped structure 67. (Wireless electrodes 11, 12, 24, 25, 26, 27, 32, 33, are known in the art, such as that described by Ryan Kaveh et al. in Nature Communications on Aug. 2, 2024. Wireless dry EEG electrodes are available from Zeto, Inc. headquarter in Santa Clara, California.) There are well-known wireless amplifiers available, such as BioNomadix 2Ch Wireless EEG Amplifier (Part #: BN-EEG2), BioNomadix 2Ch Wireless EOG Amplifier (Part #BN-EOG2) and BioNomadix 2Ch Wireless ECG Amplifier (Part #BN-ECG2), all being made by BIOPAC Systems, Inc. (Goleta, California). Using these wireless amplifiers as amplifiers and filters 22, 13, 34, the EEG recording module 21, the EOG recording module 10, and/or the ECG recording module 31 may be configured to be in wireless electronic communication 19 with the wireless EEG electrodes 24, 25, 26, 27, wireless EOG electrodes 11, 12, and wireless ECG electrodes 32, 33. Thus, the EEG recording module 21, the EOG recording module 10, and the ECG recording module 31 may be separated from their electrodes 11, 12, 24, 25, 26, 27, 32, 33, and, (together with the processing unit 50, 401), be housed in a wearable (watch-type) client device 400A, or a portable smart-phone-type client device 400B, etc.

It should be understood that the housing structure 60 of the present invention is preferably configured to be made with flexible elastic and adaptable material, for example ultra-soft silicone-type material. All of the electrodes 11, 12, 24, 25, 26, 27, 31, 32, (for EOG, EEG, ECG) and the light generator 41 and light detecting sensor 42 (for the ear-canal pulse oximeter 71A) are configured to be partially embedded in a surface (with slight protrusion at the surface) of the housing structure 60 (including earbud-style structure 61, in-the-ear portion 66 of the behind-the-ear-hearing-aid-style structure 63 or tubular-shaped structure 67). This is much more secure than conventional EOG, EEG and ECG electrodes that are usually attached or glued on the surface of the wearer's (user) 900 skin. This feature of the present invention will ensure that the electrodes 11, 12, 24, 25, 26, 27 and the light generator 41 and light detecting sensor 42 will not be easily dislodged and will be suitable for repeated long-time use.

A First Preferred Embodiment

In preferred embodiments, the present invention may comprise a novel auricular electrooculogram (EOG) system 101 which may be used in ophthalmology and neuropsychiatric evaluations or in robotics, gaming and brain-computer interface (EOG together with EEG). The auricular EOG system 101 can also be used as a component of sleep assessment and sleep monitoring. REM (rapid eye movement) sleep is a very important stage of sleep. Electrooculogram (EOG) is essential for accurate REM sleep monitoring. The traditional EOG includes two EOG electrodes, one being placed 1 cm above the outer canthus of the right eye and the other one being placed 1 cm below the outer canthus of the left eye. Certified technician is required for the placement of these electrodes. These two electrodes can pick up the extra-ocular movements of the eyes by measuring the electrical potential difference between the cornea and retina, or more precisely, in virtue of changing orientation of the corneo-retinal potential as caused by eyeball movements by extra-ocular muscles.

In some embodiments, an auricular EOG system 101 may comprise an EOG recording module 10 that may be in wired or wireless electronic communication 19 with at least two wired or wireless EOG electrodes 11, 12. The EOG electrodes 11, 12, may be coupled to an ear 902 or a peri-auricular area 903 around the ear 902. When the EOG electrodes 11, 12, are coupled to the ear 902 or the peri-auricular area 903 around the ear 902, the EOG electrodes are configured to contact the skin of separated areas selected from at least one of the following: the external ear of a wearer's ear 902, external ear canal 904 of the wearer's ear, and the peri-auricular area 903 around the wearer's ear.

In some embodiments, an auricular EOG system 101 may comprise a housing structure 60 which may be configured as an earbud style structure 61. Preferably, the auricular EOG system 101 may comprise an EOG recording module 10 that may be housed in the earbud-style structure 61. Preferably, the earbud-style structure 61 may comprise a horizontal portion 62 and each of the EOG electrodes 11, 12, may be located on or placed at separate locations on the surface 62A of the horizontal portion 62 of the earbud-style structure 61 which can be inserted into the wearer's external ear canal 904. (FIG. 6). Each EOG electrode 11, 12, may be partially embedded in the surface 62A of the horizontal portion 62 with slight protrusion at the surface 62A of the horizontal portion 62. The horizontal portion 62 may comprise a flexible elastic and adaptable material (such as soft foam or ultra-soft silicone-type material), and the flexible elastic and adaptable material may be configured to have appropriate flexibility, elasticity and adaptability such that the EOG electrodes 11, 12, are naturally and snugly in contact with skin of the external ear canal 904 of the wearer's ear 902 when the horizontal portion 62 is inserted into the external ear canal 904 of the wearer's ear 902.

In some embodiments, an auricular EOG system 101 may comprise a housing structure 60 which may be configured as a behind-the-ear-hearing-aid-style structure 63. Preferably, the auricular EOG system 101 may comprise an EOG recording module 10 that may be housed in the behind-the-ear-hearing-aid-style structure 63, the behind-the-ear-hearing-aid-style structure 63 having an in-the-ear portion 66 and a behind-the-ear portion 65. (FIG. 7). The EOG electrodes 11, 12, may be configured to be partially embedded in the surface 66A of the in-the-ear portion with slight protrusion at the surface 66A of the in-the-ear portion 66. The EOG electrodes 11, 12, may be located on or placed at separate locations on the surface 66A of the in-the-ear portion 66 which can be inserted into the wearer's external ear canal 904. The in-the-ear portion 66 may comprise a flexible elastic and adaptable material (such as soft foam or ultra-soft silicone-type material) and the flexible elastic and adaptable material is configured to have appropriate flexibility elasticity and adaptability such that the EOG electrodes 11, 12, are naturally and snugly in close contact with the skin the external ear canal 904 of the wearer's ear 902 when the in-the-ear portion 66 is inserted into the external ear canal 904 of the wearer's ear 902.

The peri-auricular area 903 refers to a portion of the head around the auricle (pinna) and this portion of the head is typically hairless. The peri-auricular area 903 includes a portion of the head in front of the auricle (pre-auricular area) and a portion of the head above and behind the auricle (post-auricular area). The pre-auricular area is small, about one inch wide and two inches long and curved along the anterior edge of the auricle. The post-auricular area is also small, about one inch wide and about three inches long and curved along the superior and posterior edges of the auricle (pinna). The post-auricular area is where a behind-the-ear hearing aid is usually located. These small pre-auricular area and post-auricular area together will be called "peri-auricle area 903" herein. (Anterior, posterior, superior, in front of and behind etc. all refer to the directions relative to the wearer's head 901 when the wearer 900 is in an upright position.)

Alternatively, these two EOG electrodes 11, 12, may be placed at separate locations of a housing structure 60 (e.g., a horizontal portion 62 of an earbud-style structure 61, an in-the-ear portion 66 of a behind-the-ear-hearing-aid-style structure 63 or a tubular-shaped structure 67). Preferably, these EOG electrodes 11, 12, are placed at different heights and different depth since the extra-ocular movements are two-dimensional movements rather than single-dimensional movements. For example, a first EOG electrode 11, 12, may be placed on the upper surface of the horizontal portion 62 of an earbud-style structure 61 while a second EOG electrode 11, 12, may be place on the anterior surface of the horizontal portion 62 of the earbud-style structure 61. (Upper, anterior and horizontal all refer to the directions of the earbud referenced to the wearer's head after the earbud horizontal portion 62 is inserted into the wearer's external ear canal 904 with the wearer in an upright position.) The EOG electrodes 11, 12, may also be placed at different depths of the earbud-style structure 61. One EOG electrode 11, 12, may be linked with an EOG recording module 10 through a wire of a local interface 58 and the other EOG electrode 11, 12, may be linked with the EOG recording module 10 through another wire of a local interface 58. The EOG recording module 10 may be configured to detect changes of electro-potential differences between the cornea and the retina as generated by extra-ocular movements of the eyes and detect the extra-ocular eye movement data of the wearer 900. Alternatively, the EOG electrodes 11, 12, may be wireless electrodes and may be configured to be in wireless electronic communication 19 with the EOG recording module 10. The EOG recording module 10 is in electronic communication 19 with a processing unit 50, 401. The processing unit 50, 401 is configured to analyze the EOG data to detect extra-ocular movements of the wearer's eyes. The processing unit 50, 401 is further configured to detect both saccadic eye movements (rapid eye movements) and slow eye movements. The extra-ocular movement data can help determination of REM sleep stage. The extra-ocular movement data is also valuable in ophthalmological and neuro-psychiatric evaluations.

In some embodiments, the EOG electrodes 11, 12, of the auricular EOG system 101 may be housed in a tubular-shaped structure 67. The tubular-shaped structure 67 is configured to be made from elastic flexible and adaptable material (such as soft foam or ultra-soft silicone-type material). The elastic flexible and adaptable material of the tubular-shaped structure 67 is configured to have appropriate elasticity, flexibility and adaptability such that it will naturally adapt to the contour of the wearer's external ear canal 904 and snugly fill the interior of the wearer's external ear canal 904 when the tubular-shaped structure 67 is inserted into the wearer's external ear canal 904. All of the electrodes 11, 12, may be configured to be partially embedded in the surface 67A of the tubular-shaped structure 67 with slight protrusion at the surface 67A of the tubular-shaped structure such that all of these electrodes 11, 12, will be naturally in contact with the skin of the wearer's external ear canal 904. Installing and removing these electrodes 11, 12, will be as easy as inserting and removing the tubular-shaped structure 67 from the wearer's external ear canal 904.

In some embodiments, an auricular EOG system 101 may optionally comprise two EOG recording modules 10 that may be utilized by a wearer 900, with the EOG electrodes 11, 12, of the first EOG recording module 10 being placed in one ear 902 and the EOG electrodes 11, 12 of the second EOG recording module 10 being place in the other ear. Preferably, the EOG electrodes 11, 12, of these two EOG recording modules 10 are placed in mirror-image way in regard to heights depths and sequence. For example, for the first EOG electrodes 11, 12, set, the inner (deeper) EOG electrode 11, 12, may be placed on the upper surface of the horizontal portion 62 of the earbud-style structure 61, while the outer (less deep) EOG electrode 11, 12, may be placed on the anterior surface of the horizontal portion 62 of the earbud-style structure 61. For the second EOG electrodes 11, 12, set, the inner (deeper) EOG electrode 11, 12, may be also placed on the upper surface of the horizontal portion 62 of the earbud-style structure 61 while the outer (less deep) EOG electrode 11, 12, may be placed on the anterior surface of the earbud-style structure 61. Since the two human eyes are usually making conjugate movements, the mirror-image locations of the bilateral EOG electrodes 11, 12, may enhance the sensitivity for these two EOG electrode 11, 12, sets to pick up extra-ocular movements.

A Second Preferred Embodiment

In some embodiments, the present invention may comprise a concise at-home sleep monitoring system 102. The concise at-home sleep monitoring system 102 preferably comprises an auricular electroencephalography (EEG) monitoring system 20 and an ancillary sleep surveillance system 70. The auricular EEG monitoring system 20 may comprise a first auricular EEG recording module 21. The first auricular EEG recording module 21 optionally comprises a first set of a plurality of (at least two, but preferably more than two) wired or wireless miniature EEG electrodes 24, 25, 26, 27, which are linked with the first EEG recording module 21 through electronic communication 19 (such as via wires of a local interface 58 or wirelessly). All of the first set EEG electrodes 24, 25, 26, 27, are configured to be coupled to a wearer's first ear 902 or peri-auricular area 903 around the wearer's first ear. The EEG recording module 21 is configured to record EEG data via the first set EEG electrodes 24, 25, 26, 27. The first set EEG electrodes 24, 25, 26, 27, are configured to be in close contact with separate areas of the skin of the wearer 900, the separate areas comprising at least one of the following locations: external ear 902 of the wearer's first ear 902, external ear canal 904 of the wearer's first ear 902, and the peri-auricular area 903 around the wearer's first ear 902 when the first set EEG electrodes 24, 25, 26, 27, are coupled to the wearer's first ear 902 or the peri-auricular area 903 around the wearer's first ear 902. (FIG. 2).

The auricular EEG recording module 21 may be in electronic communication with a processing unit 50, 401 through Bluetooth, wired or other electronic connection communication 19 means. The first EEG recording module 21 collects or records EEG data via the first set EEG electrodes 24, 25, 26, 27, and these data are transmitted to the processing unit 50, 401. With the help of various EEG analysis algorithms (prior art), the processing unit 50, 401 is configured to analyze the EEG data for assessment of the brain activities of the wearer. The brain activities collected by the processing unit 50, 401 include EEG data for classification of different sleep stages. The EEG data collected by the processing unit 50, 401 are also very useful for evaluation of neuropsychiatric disorders.

In some embodiments, a concise at-home sleep monitoring system 102 may comprise an auricular EEG monitoring system 20 which includes two EEG recording modules 21 that may be utilized by a wearer 900, with the first EEG recording module 21 optionally being configured to record EEG from the first ear 902 or the peri-auricular area 903 around the first ear 902 and the second EEG recording module 21 optionally being configured to record EEG from the second ear 902 or the peri-auricular area 903 around the second ear 902. The second EEG recording module 21 may be in wired or wireless electronic communication 19 with a second set of a plurality of miniature EEG electrodes 24, 25, 26, 27. The first EEG recording module 21 is configured to record EEG data via its first set of miniature EEG electrodes 24, 25, 26, 27. The second EEG recording module 21 is configured to record EEG data via its second set of miniature EEG electrodes 24, 25, 26, 27. The second set EEG electrodes 24, 25, 26, 27, are configured to be coupled with the wearer's second ear 902 or peri-auricular area 903 around the wearer's second ear. The second set EEG electrodes 24, 25, 26, 27, are configured to be in contact with separate areas of the skin of at least one of the following locations: external ear canal 904 of the wearer's second ear, external ear 902 of the wearer's second ear, and peri-auricular area 903 around the wearer's second ear when the second set EEG electrodes are coupled to the wearer's second ear 902 or the peri-auricular area 903 around the wearer's second ear. The second auricular EEG recording module 21 is also in electronic communication 19 with the processing unit 50, 401 through Bluetooth or other connection means. With combination of two EEG recording modules 21, this auricular EEG monitoring system 20 will be more capable to assess the brain activities of both sides of the brain of the wearer 900.

In preferred embodiments, a concise (at-home) sleep monitoring system 102 may comprise an auricular EEG monitoring system 20 and an ancillary sleep surveillance system 70. In some embodiments, an ancillary sleep surveillance system 70 may comprise at least one of the following sensors or monitors for assessment and monitoring of sleep profile: a pulse oximeter 71, a peripheral arterial tonometry (PAT) monitor 72, an airflow sensor (airflow meter) 73, an actigraphy sensor (or motion sensor) 74, a breathing monitor (respiratory inductance plethysmography (RIP) monitor) 75, a leg movement sensor 76, a body temperature sensor 77, an electromyogram (EMG) sensor (usually EMG of submental muscle [chin] and/or anterior tibialis muscle [leg]) 78, an electrocardiogram (ECG) sensor 79, a body position sensor 80, a blood pressure monitor 81, and/or any other body parameter measuring sensor.

The concise at-home sleep monitoring system 102 further comprises a processing unit 50, 401. The processing unit 50, 401 is in electronic communication 19 with the auricular EEG monitoring system 20, and the processing unit 50, 401 is also in electronic communication with each comprising (incorporated) monitor or sensor of the ancillary sleep surveillance system 70, e.g., a pulse oximeter 71, a peripheral arterial tonometry (PAT) monitor 72, an airflow sensor (airflow meter) 73, an actigraphy sensor (or motion sensor) 74, a breathing monitor (respiratory inductance plethysmography (RIP) monitor) 75, leg movement sensor 76, body temperature sensor 77, electromyogram (EMG) sensor (usually EMG of submental muscle [chin] and/or anterior tibialis muscle [leg]) 78, electrocardiogram (ECG) sensor 79, body position sensor 80, blood pressure monitor 81, and/or any other body parameter measuring sensor. With the help of various EEG analysis algorithms, the processing unit 50, 401, is configured to analyze the EEG data for assessment of the wearer's brain activities, including brain waves data which are used in classification of sleep stages. With the help of sleep analysis algorithms, the processing unit 50, 401, is further configured to analyze the data collected by the EEG recording module 21, and the data collected from any incorporated sensor or monitor of the ancillary sleep surveillance system 70 (incorporated sensor or monitor of the ancillary sleep surveillance system 70 may include at least one of the following: pulse oximeter 71, PAT monitor 72, airflow sensor 73, actigraphy sensor or motion sensor 74, RIP monitor 75, leg movement sensor 76, body temperature sensor 77, electromyogram (EMG) sensor 78, electrocardiogram (ECG) sensor 79, body position sensor 80, blood pressure monitor 81, and/or any other body parameter measuring sensor) to assess the wearer's sleep profile and also to detect presence of obstructive sleep apnea (OSA), presence of central sleep apnea (CSA) and presence of sleep disorders. The sleep profile may include one or more of the following: sleep architecture, sleep stages, sleep latency, sleep density, sleep duration, sleep quality, OSA and CSA. The sleep profile preferably may also include Apnea-Hypopnea Index (AHI). The AHI score can be used to classify the severity of sleep apnea. The sleep disorders may include narcolepsy, restless leg syndrome, periodic limb movement disorder, REM sleep behavior disorder, insomnia and parasomnias.

Preferably, one or more components (20, 71A, 50) of the concise at-home sleep monitoring system 102 may be housed in a housing structure 60 selected from one of the following: an earbud style structure 61, a behind-the-earhearing-aid-style structure 63 (structure adapted from a behind-the-ear hearing aid) and a tubular-shaped structure 67.

The concise at-home sleep monitoring system 102 preferably further comprises a network interface 85, 406, in communication with the processing unit 50, 401. The network interface 85, 406, may be configured to generate a notification to a client device 400 of the wearer about the wearer's sleep profile. The network interface 85, 406, may be configured to generate a report of the sleep profile of the wearer 900, that may include one or more of the sleep architecture, sleep stages, sleep latency, sleep duration, sleep density, sleep quality, presence of central sleep apnea (CSA) and presence of obstructive sleep apnea (OSA). In some embodiments, when the processing unit 50, 401, detects presence of OSA, the network interface 85, 406, is configured to automatically send or generate a warning notification immediately to the client device 400 of the wearer 900 of the concise sleep monitoring system 102. Preferably, a speaker 86, 404A, a vibrator 87, 404B, and/or a display screen 89, 404C is in electronic communication with the network interface 85, 406. The display screen 89, 404C may be configured to generate a notification with visual display of the wearer's sleep profile and EEG profile. In some embodiments, a concise at-home sleep monitoring system 102 may comprise a display screen 89, 404C (such as a display screen 89 on the housing structure 60 and/or a display screen 404C on a client device 400). Preferably, the network interface 85 is configured to send signals to the display screen 404C that is configured to generate a visible notification on the client device 400 of the wearer 900 describing the wearer's sleep profile and EEG profile. Optionally, the network interface 85 is configured to send signals to the display screen 89 that is configured to generate a visible notification on the housing structure 60 describing the wearer's sleep profile and EEG profile. (For example, the display screen 89 on the housing structure 60 may show very brief visible information to remind the wearer 900 to see more detailed visible information on the display screen 404C on the client device 400 of the wearer 900). The speaker 86, 404A, may be configured to automatically generate an audible notification to the wearer 900 immediately to alert the wearer 900 to take appropriate action when the processing unit 50, 401, detects presence of obstructive sleep apnea. The vibrator 87, 404B, may be configured to automatically generate a tactile notification to the wearer 900 immediately to alert the wearer 900 to take appropriate action when the processing unit 50, 401, detects presence of obstructive sleep apnea. The notifications may serve as a warning may help to alert the wearer 900 to change the sleep position in order to alleviate or stop the OSA. If the wearer 900 is using any device (such as continuous positive airway pressure or CPAP, or anti-snoring oral devices) to treat OSA, the warning can alert the wearer 900 to adjust the settings of the device or to re-attach the device (such as CPAP or anti-snoring oral device) if the device became detached during sleep.

The earbud style structure 61 would be particularly preferred for housing purpose for a concise at-home sleep monitoring system 102. All of the EEG electrodes 24, 25, 26, 27, may be configured to be partially embedded in the surface 62A of the horizontal portion 62 with slight protrusion at the surface 62A of the horizontal portion 62 of the earbud-style structure 61. Preferably the horizontal portion 62 of the earbud-style structure 61 may comprise an elastic, flexible and adaptable material (for example soft foam or ultra-soft pacifier-grade silicone material) so that the material for the horizontal portion 62 is configured to have appropriate elasticity, flexibility and adaptability such that when the horizontal portion 62 of the earbud-style structure 61 is inserted into a wearer's external ear canal 904, the horizontal portion 62 of the earbud-style structure 61 will naturally adapt to the contour of wearer's external ear canal 904 and will snugly fill the interior of the wearer's external ear canal 904. This set-up and the flexibility, elasticity and adaptability of the material will allow all of the EEG electrodes 24, 25, 26, 27, to be naturally and snugly in contact with the skin of the wearer's external ear canal 904. (FIG. 6). Installing or removing these EEG electrodes 24, 25, 26, 27, will be as easy as inserting or removing the earbud style structure 61 from the wearer's external ear canal 904. There will be no need for a certified technologist to apply the EEG electrodes 24, 25, 26, 27. Applying adhesive material to secure these EEG electrodes 24, 25, 26, 27, will also be unnecessary. This will provide huge convenience for the wearer 900. The ultra-soft silicone-type material will facilitate steady uniform and easy installation of the EEG electrodes 24, 25, 26, 27. Since the EEG electrodes 24, 25, 26, 26 are partially embedded in the surface 62A (with slight protrusion at the surface 62A) of the horizontal portion 62 of earbud-style structure 61, accidental dislodgement of an individual electrode 24, 25, 26, 27 can be avoided. Being snugly filled inside the external ear canal 904 will help to avoid movement interference during EEG recording. This will allow the wearer (user) 900 to move around freely while the EEG recording is taking place.

These advantages can be similarly achieved when using a housing structure 60 comprising a behind-the-ear-hearing-aid-style structure 63 to contain or house the auricular EEG monitoring system 20. The EEG electrodes 24, 25, 26, 27, may be configured to be housed within the in-the-ear portion 66 of a behind-the-ear-hearing-aid-style structure 63. The in-the-ear portion 66 may be made with an elastic flexible and adaptable material (for example: soft foam or very soft silicone type material), such that the material for the in-the-ear portion 66 is configured to have appropriate elasticity, flexibility and adaptability such that the in-the-ear portion 66 will naturally adapt to the contour of the wearer's external ear canal 904 and snugly fill the interior of the external ear canal 904 when it is inserted into the wearer's external ear canal 904. All of the EEG electrodes 24, 25, 26, 27, may be configured to be partially embedded in the surface 66A of the in-the-ear portion 66 with slight protrusion at the surface 66A of the in-the-ear portion 66 so that all of these EEG electrodes 24, 25, 26, 27, will be naturally and snugly in contact with the skin of the wearer's external ear canal 904. Installing or removing these EEG electrodes 24, 25, 26, 27, will be as easy as inserting or removing the in-the-ear portion 66 from the wearer's external ear canal 904. There will be no need for a certified technologist to apply the EEG electrodes 24, 25, 26, 27. Applying adhesive material to secure these EEG electrodes 24, 25, 26, 27, will not be needed. The soft foam or ultra-soft silicone-type material will facilitate steady uniform and easy installation of the EEG electrodes 24, 25, 26, 27. Since the EEG electrodes 24, 25, 26, 26 are partially embedded in the surface 66A (with slight protrusion at the surface 66A) of the in-the-ear portion 65, accidental dislodgement of an individual electrode 24, 25, 26, 27 can be avoided. Being snugly filled inside the external ear canal 904 will help to avoid movement interference during EEG recording. This will allow the wearer (user) 900 to move around freely while the EEG recording is taking place. Similar advantages can be achieved when a tubular-shaped structure 67 is configured to be used for housing purpose for a concise at-home sleep monitoring system 102. The EEG electrodes 24, 25, 26, 27, may be configured to be housed (partially embedded) in the surface 67A of the tubular-shaped structure 67. The tubular-shaped structure 67 may be made with an elastic flexible and adaptable material (for example: soft foam or very soft silicone type material), such that the material for the tubular-shaped structure 67 is configured to have appropriate elasticity, flexibility and adaptability such that the tubular-shaped structure 67 will naturally adapt to the contour of the wearer's external ear canal 904 and snugly fill the interior of the external ear canal 904 when it is inserted into the wearer's external ear canal 904. All of the EEG electrodes 24, 25, 26, 27, may be configured to be partially embedded in the surface 67A of the tubular-shaped structure 67 with slight protrusion at the surface 67A of the tubular-shaped structure 67 so that all of these EEG electrodes 24, 25, 26, 27, will be naturally and snugly in contact with the skin of the wearer's external ear canal 904. Installing or removing these EEG electrodes 24, 25, 26, 27, will be as easy as inserting or removing the tubular-shaped structure 67 from the wearer's external ear canal 904.

Earbuds or in-the-ear pieces specially designed for sleep have been known in the art. With ultra-soft material (such as pacifier-grade silicone), these sleep-friendly designs provide comfort during sleep, including side sleeping position. The designs also ensure staying in place throughout the night. Examples for wireless sleep-friendly earbuds include Soundcore Sleep A20 by Anker Sleep Earbuds (Ontario, California), Google Pixel Buds Pro wireless (Mountain View, California) and Bose Sleepbuds 2 or 3 (Framingham, Massachusetts). Ear wax (cerumen) repellant earbuds are also known in the art. By using hydrophobic materials, such as silicone or nano-coatings, these earbuds can help decrease earwax from accumulating.

Most of the conventional pulse oximeters 71 are the transmittance pulse oximeter 71B (transmissive mode) type (FIG. 13) and they are usually worn on thin parts of the body, like fingers, toes or earlobes (lobule of ear). For the present invention, the pulse oximeter 71 may be a conventional transmittance pulse oximeter 71B worn on the finger (or toe or earlobe) and be in electronic communication with a processing unit 50, 401. Alternatively, a concise sleep monitoring system 102 may comprise a reflectance (reflective-mode) pulse oximeter 71 having a reflectance oximeter module 40A (FIG. 14) which may be housed in an earbud-style structure 61, or a behind-the-ear-hearing-aid-style structure 63, or a tubular-shaped structure 67, forming an ear-canal pulse oximeter 71A.

In some embodiments, a concise at-home sleep monitoring system 102 preferably further comprises a wired or wireless ear-canal pulse oximeter 71A. The ear-canal pulse oximeter 71A preferably comprises a reflectance oximeter module 40A having a wired or wireless light generator 41, a wired or wireless light detecting sensor (photodiode) 42, and a detection module 45. The light generator 41 and the light detecting sensor 42 are configured to be coupled to the external ear canal 904 of a wearer 900 to be in contact with the skin of the external ear canal of the wearer's ear 902. The light generator 41 comprises a light emitting diode configured to generate light of different wavelengths that are commonly used to measure oxygen saturation in tissue. The light detecting sensor 42 is configured to measure light absorption of different wavelengths, including red and infrared wavelengths. The light generator 41 and the light detecting sensor 42 may be in electronic communication 19 with the detection module 45 through local interface 58 (wire) or wirelessly. The detection module 45 is configured to analyze the data from the light generator 41 and the light detecting sensor 42 to record, assess, determine, etc., the wearer's pulse data and the data of the wearer's blood oxygen saturation level. The ear-canal pulse oximeter 71A may be configured to be housed in the horizontal portion 62 of an earbud-style structure 61 or a tubular-shaped structure 67 or the in-the-ear portion 66 of a behind-the-ear-hearing-aid-style structure 63. The light generator 41 and the light detecting sensor (photodiode) 42 of the ear-canal pulse oximeter 71A may be configured to be located at a surface and partially embedded in the surface of a housing structures 60, for example: the surface 62A of the horizontal portion 62 of the earbud-style structure 61 or the surface 67A of a tubular-shaped structure 67 or the surface 66A of the in-the-ear portion 66 of the behind-the-ear-hearing-aid-style structure 63. The horizontal portion 62 of the earbud-style structure 61 or the tubular-shaped structure 67 or the in-the-ear-portion 66 of the behind-the-ear-hearing-aid-style structure 63 is configured to be made with flexible elastic adaptable material (e.g., soft foam or ultra-soft silicone material) that is configured to have appropriate flexibility elasticity and adaptability such that the light generator 71 and the light detecting sensor 72 of the ear-canal pulse oximeter 71A will be naturally in close contact with the skin of the wearer's external ear canal 904 and snugly fill the interior of the wearer's external ear canal 904 when the earbud-style structure 61 or the tubular-shaped structure 67 or in-the-ear portion 66 of the behind-the-ear-hearing-aid-style structure 63 is inserted into the wearer's external ear canal 904. (FIGS. 1-3, 14, 16). Wireless pulse oximeters are readily available (such as Aulisa GA 1000-A or GA 1000-P from Turner Medical, Colchester, Connecticut). The ear-canal pulse oximeter 71A is configured to be in wireless and/or wired electronic communication with a processing unit 50, 401, of the sleep-monitoring systems 102, 103 or the auricular health monitoring systems 104. (FIGS. 1-4, 14, 16).

In some embodiments, a separate client device 400 may be used for housing of some of the components of concise at-home sleep monitoring system 102. For example, one or more of an EEG recording module 21 and the processing unit 50, 401, may be housed in a wearable watch-type client device 400A which can be worn on wrist, or a portable smart-phone-type client device 400B which can be carried or put on a nearby table. The EEG electrodes 24, 25, 26, 27, may comprise or be configured as wireless electrodes, and the wireless EEG electrodes 24, 25, 26, 27, may be housed in a housing structure 60 that may be one of the following: an earbud-type structure 61, an in-the-ear portion 66 of a behind-the-ear-hearing-aid-style structure 63, and a tubular-shaped structure 67. (Wireless electrodes such as that described by Ryan Kaveh et al. in Nature Communications on Aug. 2, 2024. Wireless dry EEG electrodes are also available from Zeto, Inc. in Santa Clara, California). The EEG recording module 21 may comprise a wireless EEG amplifier 22 (such as those amplifiers made by the BIOPAC Systems, Inc. in Goleta, California), and the ear-canal pulse oximeter 71A may comprise a wireless reflectance oximeter module 40A and the EEG recording module 21, the wireless reflectance oximeter module 40A and the processing unit 50, 401, may be housed in a wearable watch-type client device 400A and/or a portable smart-phone-type client device 400B.

The sleep monitoring by conventional smart watches and health trackers is not very accurate because they use other parameters to "guess" the sleep stages. These conventional smart watches and health trackers do not have EEG, making them unable to accurately monitor the sleep stages. With the auricular EEG of this invention, this concise at-home sleep monitoring system will become much more accurate.

The concise at-home sleep monitoring system 102 of the present invention may be more accurate than the traditional polysomnogram (PSG) since wearer 900 of this concise at-home sleep monitoring system 102 may sleep in the wearer's own bedroom while user of polysomnogram sleeps in a sleep center or a medical facility. This concise at-home sleep monitoring system 102 also has another advantage that it could notify the wearer 900 to change sleep position or adjust the CPAP or anti-snoring oral device on the spot when OSA is detected. Another advantage is that this concise at-home sleep monitoring system 102 can be used repeatedly every night. This is very important for wearer 900 who has sleep apnea since sleep apnea is a long-term problem.

In some embodiments, a concise sleep monitoring system 102 may be configured as a simplified sleep monitoring system that may comprise an auricular EEG monitoring system 20, an ancillary sleep surveillance system 70, and a processing unit 50, 401. The ancillary sleep surveillance system 70 comprises a pulse oximeter 71 and the simplified sleep monitoring system may use the pulse oximeter 71 as a surrogate for sleep apnea detection.

There is a trade-off regarding how many sensors to be used in an at-home sleep monitoring study. Using more sensors may improve the accuracy of the sleep study and provide more detail about the sleep profile. However, more sensors may make it more cumbersome and more inconvenient for people to use at home and also increase the risk of sensors falling off or being dislodged during sleep. More sensors also might interfere with sleep. A concise limited sleep monitoring system 102 configured as a simplified sleep monitoring system will be very easy to use and very practical for the purpose of monitoring sleep apnea. It will be very suitable for long-term nightly use.

Alternatively, a separate client device 400 may be used for housing of some of the components of a concise limited sleep monitoring system 102 configured as a simplified sleep monitoring system. For example, an EEG recording module 21 and the processing unit 401 may be housed in a client device 400, such as a wearable client device 400A (e.g., wearable watch-type structure) or a portable smart-phone-type client device 400B (portable smart-phone-type structure). Wireless EEG electrodes 24, 25, 26, 27, may be utilized. (Wireless electrodes such as that described by Ryan Kaveh et al. in Nature Communications on Aug. 2, 2024. Wireless dry EEG electrodes are available from Zeto, Inc. headquarter in Santa Clara, California.) The wireless EEG electrodes 24, 25, 26, 27, and the wireless light generator 41 and wireless light-detecting sensor 42 of the ear-canal pulse oximeter 71A may be housed in one of the following: an earbud style structure 61, an in-the-ear portion 66 of a behind-the-ear-hearing-aid-style structure 63 or a tubular-shaped structure 67. There are well-known wireless EEG amplifiers available, such as BioNomadix 2Ch Wireless EEG Amplifier (Part #: BN-EEG2), made by BIOPAC Systems, Inc. (Goleta, California). Using wireless amplifier for EEG amplifiers and filters 22 and wireless amplifier for ear-canal pulse oximeter amplifier and filter 43, the EEG recording module 21, the reflectance oximeter module of the ear-canal pulse oximeter and the processing unit 401 may be separated from the EEG electrodes 24, 25, 26, 27, and the light generator 41 and light-detecting sensor 42, and be housed remotely in a wearable client device 400A or a portable smart-phone-type client device 400B.

By incorporating an auricular EEG monitoring system 20 into the at-home sleep monitoring systems of the present invention, these at-home sleep monitoring systems can achieve much higher accuracy since actual sleep time can be determined, rather than just "guessed". This is important when calculating AHI (Apnea-Hypopnea Index) score. AHI score is the average number of times a person has apnea and hypopnea events per one hour of sleep. AHI score is the cornerstone for the diagnosis of sleep apnea. For adults, a normal AHI score is less than 5. The sleep apnea severity is classified with the AHI scores as follows: Mild: 5 to 14, Moderate: 15 to 29, Severe: 30+. Accurate scoring of AHI is one of the major advantages of the present invention.

A Third Preferred Embodiment

In some embodiments, the present invention may comprise a novel auricular sleep monitoring system 106 suitable for at home use. The auricular sleep monitoring system 106 may comprise an auricular EEG monitoring system 20, an ear-canal pulse oximeter 71A and a processing unit 50, 401. The auricular EEG monitoring system 20 is as described hereinbefore. Preferably, the auricular sleep monitoring system 106 uses the ear-canal pulse oximeter 71A as a surrogate for sleep apnea detection. The ear-canal pulse oximeter 71A is configured to record the wearer's pulse data and blood oxygen saturation data. Sleep apnea (including obstructive sleep apnea, central sleep apnea or mixed sleep apnea) is usually associated with significant drop of blood oxygen saturation. As commonly accepted, normal range of blood oxygen saturation is about 95-100%, low blood oxygen saturation is about 89-92%, while dangerously low blood oxygen saturation (requiring medical attention) is about 88% or below. During very severe sleep apnea, the blood oxygen saturation could drop to as low as 70% or even lower temporarily. The ear-canal pulse oximeter 71A (with a light generator 41 and a light-detecting sensor 42 of a reflectance oximeter module 40A placed inside an external ear canal 904, as described hereinbefore). Wireless ear-canal pulse oximeter 71A is particularly preferred for the auricular sleep monitoring system 106 since ear-canal pulse oximeter 71A is very easy, comfortable and convenient for wearer to use. Wireless pulse oximeters are readily available (such as Aulisa GA 1000-A or GA 1000-P from Turner Medical, Colchester, Connecticut). The ear-canal pulse oximeter 71A may be a reflectance pulse oximeter that may comprise a wired or wireless reflectance oximeter module 40A having a wired or wireless light generator 41, a wired or wireless light detecting sensor (photodiode) 42, and a detection module 45. The wired or wireless light generator 41 and the wired or wireless light detecting sensor 42 are configured to be coupled to the external ear canal 904 of a wearer 900 to be in contact with the skin of the external ear canal of the wearer's ear 902. The wired or wireless light generator 41 comprises a light emitting diode configured to generate light of different wavelengths including red and infrared wavelengths, that are commonly used to measure oxygen saturation in tissue. The wired or wireless light detecting sensor 42 is configured to measure light absorption of different wavelengths, including red and infrared wavelengths. The wired or wireless light generator 41 and the wired or wireless light detecting sensor 42 may be in electronic communication with the detection module 45 through local interface 58 (wire) or wirelessly. The detection module 45 is configured to analyze the data communicated or transmitted from the wired or wireless light generator 41 and the wired or wireless light detecting sensor 42 to record, assess, determine, etc., the wearer's pulse data and the data of the wearer's blood oxygen saturation level (blood oxygen saturation data). Wireless pulse oximeters are readily available (such as Aulisa GA 1000-A or GA 1000-P from Turner Medical, Colchester, Connecticut). The ear-canal pulse oximeter 71A is configured to be in wireless and/or wired electronic communication with a processing unit 50, 401. Preferably, the wireless ear-canal pulse oximeter 71A is configured to be in wireless communication with the processing unit 50, 401.

Preferably, the auricular sleep monitoring system 106 may be housed in one of the following: an earbud-style structure 61, an in-the-ear portion 66 of a behind-the-ear-hearing-aid-style structure 63 or a tubular-shaped structure 67. The EEG electrodes 24, 25, 26, 27, and the light generator 41 and the light detecting sensor 42 of the ear-canal pulse oximeter 71A may be all configured to be located (partially embedded in the surface with slight protrusion at the surface, as described hereinbefore) on one of the following housing structures 60: the surface 62A of the earbud-style structure 61, the surface 66A of the in-the-ear portion 66 of a behind-the-ear-hearing-aid-style structure 63 or the surface 67A of the tubular-shaped structure 67. The earbud-style structure 61, the in-the-ear portion 66 of the behind-the-ear-hearing-aid-style structure 63 and the tubular-shaped structure 67 may comprise a flexible elastic and adaptable material. The flexible elastic and adaptable material of the earbud-style structure 61 or the in-the-ear portion 66 or the tubular-shaped structure 67 is configured to have appropriate elasticity flexibility and adaptability (for example soft foam or very soft silicone-type material) such that the EEG electrodes 24, 25, 26, 27, and the light generator 41 and light-detecting sensor 42 of the ear-canal pulse oximeter 71A will be naturally in close contact with the skin of the wearer's external ear canal 904 when the earbud-style structure 61 or the in-the-ear portion 66 or the tubular-shaped structure 67 is inserted into the wearer's external ear canal 904. The auricular EEG monitoring system 20 and the ear-canal pulse oximeter 71A are in electronic communication with a processing unit 50, 401. The processing unit 50, 401, is configured to receive the EEG data (from auricular EEG monitoring system 20), pulse data and blood oxygen saturation data (from ear-canal pulse oximeter 71A) to assess the wearer's primitive sleep profile and detect presence of blood oxygen saturation dropping below a pre-determined level (suggestive of probable presence of sleep apnea). (Example of a pre-determined blood oxygen saturation level: 90%, 88%, 85% or other pre-determined levels). The primitive sleep profile may include the NREM sleep stages, including wakefulness, drowsiness, NREM-N1, NREM-N2 and NREM-N3 sleep stages, as per the EEG data. (REM sleep stage cannot be accurately assessed due to absence of EOG in this auricular sleep monitoring system 106).

Preferably, the auricular sleep monitoring system 106 further comprises a network interface 85, 406, in electronic communication with the processing unit 50, 401. The network interface 85, 406, is in electronic communication with one of the following: a speaker 86, 404A, a vibrator 87, 404B, and a display screen 89, 404C (such as a display screen 89 on the housing structure 60 and/or a display screen 404C on a client device 400). When the blood oxygen saturation dropping below the pre-determined level (for example 90%, 88%, 85% or other pre-determined levels) (suggestive of probable presence of sleep apnea) is detected by the processing unit 50, 401, the processing unit 50, 401, is configured to immediately send signals to the network interface 85, 406. The network interface 85, 406, is configured to automatically send signals to the speaker 86, 404A, (that is configured to send audible notification to the wearer) or to the vibrator 87, 404B, (that is configured to send tactile notification to the wearer.) immediately to alert the wearer to take appropriate actions (appropriate actions such as changing sleep position, or adjusting CPAP or anti-snoring oral device, as described hereinbefore). The network interface 85, 406, is further configured to send signals to the display screen 89 (that is configured to generate a visible notification on the housing structure 60) and/or to the display screen 404C (that is configured to generate a visible notification on a client device 400 of the wearer 900) with description of the wearer's 900 sleep profile and presence or absence of blood oxygen saturation dropping below the pre-determined level.

The auricular sleep monitoring system 106 may further comprise a wireless EEG amplifier 22, a wireless reflectance oximeter module 40A, together with the processing unit 50, 401, and the display screen 404C may be housed remotely in a client device 400 (such as a wearable watch-type client device 400A or a portable smart phone-type client device 400B), as described hereinbefore. The entire auricular sleep monitoring system 106 can be easily installed or easily removed and is very convenient for nightly use to monitor sleep apnea. The entire auricular sleep monitoring system 106 is also very useful for daytime use to monitor health conditions since it is fully wearable and the wearer can be freely ambulatory.

A Fourth Preferred Embodiment

Figure 5:
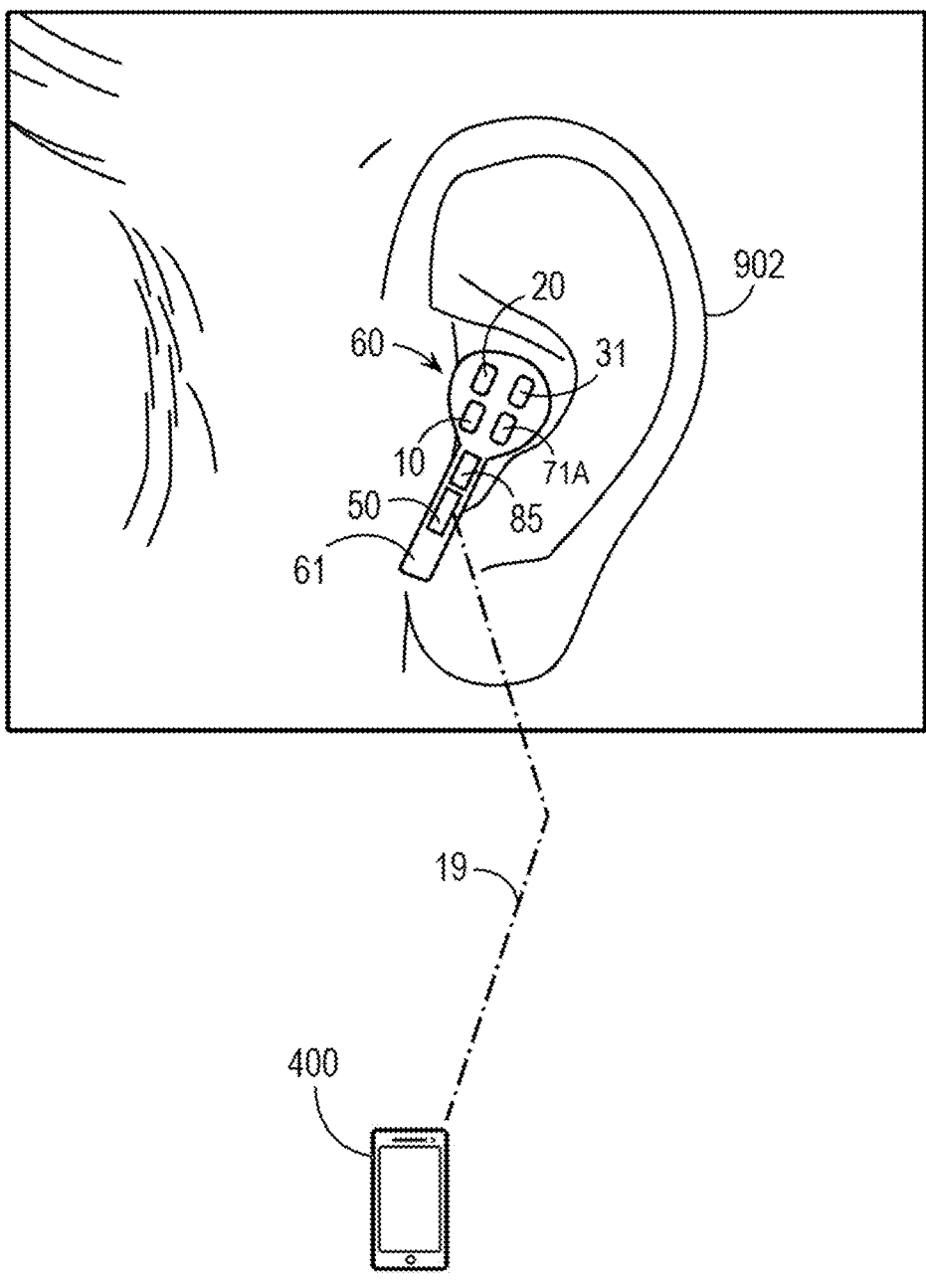
FIG. 5-FIG. 5 illustrates a perspective view of a housing structure configured as an earbud style structure housing an EOG recording module, an auricular EEG monitoring system, auricular ECG recording module, and an ear-canal pulse oximeter according to various embodiments described herein.

In some embodiments, the present invention may comprise a novel comprehensive at-home sleep monitoring system 103. The comprehensive at-home sleep monitoring system 103 may comprise an auricular EOG system 101, an auricular EEG monitoring system 20, and an ancillary sleep surveillance system 70. In some embodiments, an ancillary sleep surveillance system 70 may comprise at least one of the following sensors or monitors: a pulse oximeter 71, a peripheral arterial tonometry (PAT) monitor 72, an airflow sensor (airflow meter) 73, an actigraphy sensor (or motion sensor) 74, a breathing monitor (respiratory inductance plethysmography (RIP) monitor) 75, leg movement sensor 76, a body temperature sensor 77, an electromyogram (EMG) sensor (usually EMG of submental muscle [chin] and/or anterior tibialis muscle [leg]) 78, an electrocardiogram (ECG) sensor 79, a body position sensor 80, a blood pressure monitor 81, and/or any other body parameter measuring sensor. (FIGS. 3, 5)

An auricular EOG system 101 may comprise an EOG recording module 10 that may be in wired or wireless electronic communication 19 with at least two wired or wireless EOG electrodes 11, 12. The EOG electrodes 11, 12, may be coupled to an ear 902 or a peri-auricular area 903 around the ear 902. When the EOG electrodes are coupled to the ear 902 or the peri-auricular area 903 around the ear 902, the EOG electrodes 11, 12, are configured to contact the skin of separated areas selected from at least one of the following: the external ear of a wearer's ear 902, external ear canal 904 of the wearer's ear, and the peri-auricular area 903 around the wearer's ear. The EOG electrodes 11, 12, may be in electronic communication (e.g., wired or wireless communication) with the EOG recording module 10 which is configured to measure the electro-potential differences between the cornea and the retina of the wearer's eye and detect the extra-ocular eye movement data of the wearer 900. The EOG recording module 10 may be in electronic communication with a processing unit 50, 401. The EOG recording module 10 may be configured to record or collect EOG data of the wearer 900 via the EOG electrodes 11, 12, which can be used to detect, access, determine, etc., the extra-ocular movements of the wearer's eyes, such as for determining rapid-eye-movement (REM) sleep stage.

An auricular EEG monitoring system 20 may comprise an EEG recording module 21. The EEG recording module 21 optionally comprises a first set of a plurality of (at least two, but preferably more than two) wired or wireless EEG electrodes 24, 25, 26, 27. The first set EEG electrodes 24, 25, 26, 27, may be in electronic communication (e.g., wired or wireless communication) with the EEG recording modules 21. Preferably, each EEG electrode 24, 25, 26, 27, may be configured as a wireless EEG electrode 24, 25, 26, 27. All of the first set EEG electrodes 24, 25, 26, 27, may be configured to be coupled to a wearer's first ear 902 or a peri-auricular area 903 around the wearer's first ear. When the first set EEG electrodes 24, 25, 26, 27, are coupled to the wearer's first ear 902 or the peri-auricular area 903 around the wearer's first ear, the first set EEG electrodes 24, 25, 26, 27, are positioned in contact with separate locations on an area of the wearer 901, the area selected from one or more of the following: the external ear 902 of the wearer's first ear, the external ear canal 904 of the wearer's first ear, and the peri-auricular area 903 around the wearer's first ear. The EEG recording module 21 may be configured to record EEG data of the wearer 901 via the first set EEG electrodes 24, 25, 26, 27. The EEG recording module 21 may be in electronic communication with a processing unit 50, 401, which is configured to analyze the EEG data of the wearer 901.

In some embodiments, a comprehensive at-home sleep monitoring system 103 may comprise an auricular EEG monitoring system 20 having two sets of EEG recording modules 21 that may be utilized by a wearer 900, with the first EEG recording module 21 optionally being configured to record EEG from the first ear 902 or the peri-auricular area 903 around the first ear 902 and the second EEG recording module 21 optionally being configured to record EEG from the second ear 902 or the peri-auricular area 903 around the second ear 902. The second EEG recording module 21 comprises a second set of a plurality of miniature wired or wireless EEG electrodes 24, 25, 26, 27, linked with the second EEG recording module 21 through electronic communication 19 (such as via wires or wirelessly). The first EEG recording module 21 is configured to record EEG data via its first set miniature EEG electrodes 24, 25, 26, 27. The second EEG recording module 21 is configured to record EEG data via its second set miniature EEG electrodes 24, 25, 26, 27. The second set EEG electrodes 24, 25, 26, 27, are configured to be in contact with separate areas of the skin of at least one of the following locations: external ear canal 904 of the wearer's second ear, external ear 902 of the wearer's second ear, and peri-auricular area 903 around the wearer's second ear when the second set EEG electrodes are coupled to the wearer's second ear 902 or the peri-auricular area 903 around the wearer's second ear. The second auricular EEG recording module 21 is also in electronic communication 19 with the processing unit 50, 401 through Bluetooth or other connection means. With combination of two EEG recording modules 21, this auricular EEG monitoring system 20 will be more capable to assess the brain activities of both sides of the brain of the wearer 900.

The comprehensive (at-home) sleep monitoring system 103 further comprises a processing unit 50, 401. The processing unit 50, 401, may be in electronic communication with the auricular EEG monitoring system 20 and the auricular EOG system 101. The processing unit 50, 401, is also in electronic communication with each incorporated monitor or sensor of the ancillary sleep surveillance system 70. The incorporated sensor or monitor of the ancillary sleep surveillance system 70 include one or more of the following: pulse oximeter 71, PAT monitor 72, airflow sensor 73, actigraphy sensor (motion sensor) 74, RIP monitor 75, leg movement sensor 76, a body temperature sensor 77, an electromyogram (EMG) sensor (usually EMG of submental muscle [chin] and/or anterior tibialis muscle [leg]) 78, an electrocardiogram (ECG) sensor 79, a body position sensor 80, a blood pressure monitor 81, and/or any other body parameter measuring sensor. With the help of various EEG analysis algorithms, the processing unit 50, 401, is configured to analyze the EEG data for assessment of the wearer's brain activities, including brain waves data which are used in classification of sleep stages. Utilizing sleep analysis algorithms, the processing unit 50, 401, is further configured to analyze all of the data collected by the auricular EEG monitoring system 20, auricular EOG system 101, and each incorporated sensor or monitor from the ancillary sleep surveillance system 70 to assess the wearer's sleep profile and also to detect presence of sleep apnea. The sleep profile may include one or more of: sleep architecture, sleep stages, sleep latency, sleep density, sleep duration, sleep quality, presence of obstructive sleep apnea and presence of central sleep apnea. The sleep profile preferably may include an Apnea-Hypopnea Index (AHI) score. The AHI score can be used to classify the severity of sleep apnea. With the help of sleep analysis algorithms, the processing unit 50, 401, is further configured to detect presence of sleep disorders, which may include narcolepsy, restless leg syndrome, periodic limb movement disorder, REM sleep behavior disorder, parasomnias and insomnia.

In some embodiments, a comprehensive at-home sleep monitoring system 103 may comprise an auricular electrocardiogram (ECG) system 30 that comprises an auricular ECG recording module 31. The ECG recording module 31 may comprise at least two wired or wireless ECG electrodes 32, 33. The ECG electrodes 32, 33 are in electronic communication 19 with the ECG recording module 31. The ECG electrodes 32, 32, may be configured to be coupled to a wearer's ear 902 or a peri-auricular area 903 around the wearer's ear 902. When the ECG electrodes 32, 33, are coupled to the wearer's ear 902 or the peri-auricular area 903 around the wearer's ear 902 the ECG electrodes 32, 33, are positioned in contact with separate locations on an area of the wearer 900, the area selected from at least one of the following: external ear of the wearer's ear 902, external ear canal 904 of the wearer's ear, and the peri-auricular area 903 around the wearer's ear. These locations that the ECG electrodes 32, 33, are attached to may be adequately separated (with different angles or directions) relative to the location of the heart of the wearer 900 so that they can pick up some differences of the cardiac action potentials in order to enable the ECG recording module 31 to perform an electrocardiogram. The ECG recording module 31 may be configured to record ECG data of the wearer 90 via the ECG electrodes 32, 33, and the ECG recording module 31 may be in electronic communication with a processing unit 50, 401, which may be configured to analyze the ECG data from the ECG recording module 31. Preferably, the processing unit 50, 401, may be configured to analyze the EEG data from the EEG monitoring system 20, the EOG data from the EOG monitoring system 101, the ECG data from the ECG recording module 31, and the data from each incorporated sensor or monitor from the ancillary sleep surveillance system 70 to assess the wearer's EEG profile, EOG profile, ECG profile and the wearer's sleep profile. The wearer's sleep profile may comprise one or more of the following: sleep architecture, sleep stages, sleep latency, sleep density, sleep duration, sleep quality, apnea-hypopnea index score, presence of obstructive sleep apnea, presence of central sleep apnea, and presence of one or more sleep disorders. The one or more sleep disorders may include one or more of the following: narcolepsy, restless leg syndrome, periodic limb movement disorder, parasomnias, and rapid-eye-movement (REM) sleep behavior disorder.

Preferably, the auricular EEG recording module 21 and the auricular EOG recording module 10 may be housed in a housing structure 60 selected from one of the following: an earbud style structure 61 (earbud or airpod-like structure), a behind-the-ear-hearing-aid-style structure 63 (structure adapted from a behind-the-ear hearing aid) and a tubular-shaped structure 67.

The comprehensive at-home sleep monitoring system 103 preferably further comprises a network interface 85, 406 and one or more of the following: a speaker 86, 404A, a vibrator 87, 404B, a display screen 89 on the housing structure 60, and a display screen 404C on a client device 400, The network interface 85, 406 is in electronic communication with the processing unit 50, 401 and at least one of the following: the speaker 86, 404A, the vibrator 87, 404B, the display screen 89 on the housing structure 60 and the display screen 404C on a client device 400. Preferably, the network interface 85, 406, may be configured to generate signals to the display screen 404C and the display screen 404C is configured to generate a visible notification on the client device 400 of the wearer 900 with description of a report of the wearer's EEG profile, EOG profile, ECG profile, and/or sleep profile. Optionally, the network interface 85, 406, may be configured to generate signals to the display screen 89 and the display screen 89 may be configured to generate a visible notification on the housing structure 60 with description of the EEG profile, EOG profile, ECG profile and sleep profile of the wearer 900. (For example, the display screen 89 on the housing structure 60 may show very brief visible information to remind the wearer 900 to see more detailed visible information on the display screen 404C on the client device 400 of the wearer 900). The wearer's sleep profile might include one or more of the following: sleep architecture, sleep stages, sleep latency, sleep duration, sleep density, sleep quality, presence of central sleep apnea (CSA), presence of obstructive sleep apnea (OSA), and presence of sleep disorders. In some embodiments, when the processing unit 50, 401, detects presence of OSA, the network interface 85, 406, is configured to automatically send or generate a warning notification immediately to the client device 400 of the wearer 900 of the comprehensive sleep monitoring system 103. Preferably, a speaker 86, 404A, and/or a vibrator 87, 404B, is in electronic communication with the network interface 85, 406. The speaker 86, 404A, may be configured to automatically generate an audible notification to the wearer 900 immediately to alert the wearer 900 to take appropriate action when the processing unit 50, 401, detects presence of obstructive sleep apnea. The vibrator 87, 404B, may be configured to automatically generate a tactile notification to the wearer 900 immediately to alert the wearer 900 to take appropriate action when the processing unit 50, 401, detects presence of obstructive sleep apnea. The notifications may serve as a warning might help to alert the wearer 900 to change the sleep position in order to alleviate or stop the OSA. If the wearer 900 is using any device (such as continuous positive airway pressure or CPAP, or anti-snoring oral devices) to treat OSA, the warning can alert the wearer 900 to adjust the settings of the device or to re-attach the device (such as CPAP or anti-snoring oral device) if the device became detached during sleep.

The comprehensive at-home sleep monitoring system 103 of the present invention may be more accurate than the traditional polysomnogram since wearer 900 of this sleep monitoring system 103 may sleep in the wearer's own bedroom while user of polysomnogram sleeps in a sleep center or a medical facility. This comprehensive at-home sleep monitoring system 103 also has other advantages including much less expensive and being reusable nightly and could notify the wearer 900 to change sleep position or adjust CPAP or anti-snoring oral device on the spot when OSA is detected.

The earbud-style structure 61 would be particularly preferred for housing purpose to contain or house the EEG electrodes 24, 25, 26, 27, EOG electrodes 11, 12 (and ECG electrodes 32, 33 if auricular ECG system 30 is incorporated). All of the EEG electrodes 24, 25, 26, 27, EOG electrodes 11, 12, (and ECG electrodes 32, 33, if auricular ECG system 30 is incorporated) may be configured to be partially embedded in the surface 62A of the horizontal portion 62 of the earbud-style structure 61 with slight protrusion at the surface 62A of the horizontal portion 62 of the earbud-style structure 61. Preferably the horizontal portion 62 of the earbud-style structure 61 may comprise an elastic, flexible and adaptable material (for example soft foam or ultra-soft silicone material) so that the material for the horizontal portion 62 is configured to have appropriate elasticity, flexibility and adaptability such that when the horizontal portion 62 of the earbud-style structure 61 is inserted into a wearer's external ear canal 904, the horizontal portion 62 of the earbud-style structure 61 will naturally adapt to the contour of wearer's external ear canal 904 and will snugly fill the interior of the wearer's external ear canal 904. This set-up and the flexibility, elasticity and adaptability of the material will allow all of these electrodes 11, 12, 24, 25, 26, 27, 32, 33, to be naturally and snugly in contact with the skin of the wearer's external ear canal 904. (FIG. 6). Installing and removing these electrodes 11, 12, 24, 25, 26, 27, 32, 33, will be as easy as inserting and removing the earbud-style structure 61 from the wearer's external ear canal 904. There will be no need for a certified technologist to apply the electrodes 11, 12, 24, 25, 26, 27, 32, 33. Applying adhesive material to secure these electrodes 11, 12, 24, 25, 26, 27, 32, 33, will also be unneeded. The soft foam or ultra-soft silicone-type material will facilitate steady uniform and easy installation of the EOG, EEG and ECG electrodes 11, 12, 24, 25, 26, 27, 32, 33. Since these electrodes 11, 12, 24, 25, 26, 26, 32, 33 are partially embedded in the surface 62A (with slight protrusion at the surface 62A) of the horizontal portion 62 of the earbud-style structure 61, accidental dislodgement of an individual electrode 11, 12, 24, 25, 26, 27, 32, 33 can be avoided. Being snugly filled inside the external ear canal 904 will help to avoid movement interference during EOG, EEG and ECG recordings. This will allow the wearer (user) 900 to move around freely while the EOG, EEG, ECG recordings are taking place.

These advantages can be similarly achieved when using a housing structure 60 comprising a behind-the-ear-hearing-aid-style structure 63 to contain or house the EEG electrodes 24, 25, 26, 27, EOG electrodes 11, 12 (and ECG electrodes 32, 33 if auricular ECG system 30 is incorporated). The EEG electrodes 24, 25, 26, 27, and the EOG electrodes 11, 12, (and ECG electrodes 32, 33, if ECG system 30 is included)

may be configured to be housed within the in-the-ear portion 66 of a behind-the-ear-hearing-aid-style structure 63. (FIGS. 7, 18). The in-the-ear portion 66 may be made with an elastic flexible and adaptable material (for example: soft foam or ultra-soft silicone type material), such that the material for the in-the-ear portion 66 is configured to have appropriate elasticity, flexibility and adaptability such that the in-the-ear portion 66 will naturally adapt to the contour of the wearer's external ear canal 904 and snugly fill the interior of the external ear canal 904 when it is inserted into the wearer's external ear canal 904. All of the EEG electrodes 24, 25, 26, 27, and the EOG electrodes 11, 12, (and ECG electrodes 32, 33, if ECG system 30 is included) may be configured to be partially embedded in the surface 66A of the in-the-ear portion with slight protrusion at the surface 66A of the in-the-ear portion 66 so that all of these electrodes 11, 12, 24, 25, 26, 27, 32, 33, will be naturally and snugly in contact with the skin of the wearer's external ear canal 904. Installing and removing these electrodes 11, 12, 24, 25, 26, 27, 32, 33, will be as easy as inserting and removing the in-the-ear portion 66 from the wearer's external ear canal 904. There will be no need for a certified technologist to apply the electrodes 11, 12, 24, 25, 26, 27, 32, 33. Applying adhesive material to secure these electrodes 11, 12, 24, 25, 26, 27, 32, 33, will also be unneeded. The soft foam or ultra-soft silicone-type material will facilitate steady uniform and easy installation of the EOG, EEG and ECG electrodes 11, 12, 24, 25, 26, 27, 32, 33. Since these electrodes 11, 12, 24, 25, 26, 26, 32, 33 are partially embedded in the surface 66A (with slight protrusion at the surface 66A) of the in-the-ear portion 66, accidental dislodgement of an individual electrode 11, 12, 24, 25, 26, 27, 32, 33 can be avoided. Being snugly filled inside the external ear canal 904 will help to avoid movement interference during EOG, EEG and ECG recordings. This will allow the wearer (user) 900 to move around freely while the EOG, EEG, ECG recordings are taking place.

Optionally, all of the EEG electrodes 24, 25, 26, 27, and the EOG electrodes 11, 12, (and ECG electrodes 32, 33, if ECG system 30 is incorporated) may be housed in a housing structure 60 that comprises a tubular-shaped structure 67 (FIGS. 16, 17). The tubular-shaped structure 67 may be made with an elastic flexible and adaptable material (for example: soft foam or ultra-soft silicone type material), such that the material for the tubular-shaped structure 67 is configured to have appropriate elasticity, flexibility and adaptability such that the tubular-shaped structure 67 will naturally adapt to the contour of the wearer's external ear canal 904 and snugly fill the interior of the external ear canal 904 when it is inserted into the wearer's external ear canal 904. All of the electrodes 11, 12, 24, 25, 26, 27, 32, 33, may be configured to be partially embedded in the surface 67A of the tubular-shaped structure with slight protrusion at the surface 67A of the tubular-shaped structure 67 such that all of these electrodes 11, 12, 24, 25, 26, 27, 32, 33, will be naturally and snugly in contact with the skin of the wearer's external ear canal 904. Installing and removing these electrodes 11, 12, 24, 25, 26, 27, 32, 33, will be as easy as inserting and removing the tubular-shaped structure 67 from the wearer's external ear canal 904. There will be no need for a certified technologist to apply the electrodes 11, 12, 24, 25, 26, 27, 32, 33. Applying adhesive material to secure these electrodes 11, 12, 24, 25, 26, 27, 32, 33, will be unnecessary. The soft foam or ultra-soft silicone-type material will facilitate steady uniform and easy installation of the EOG, EEG and ECG electrodes 11, 12, 24, 25, 26, 27, 32, 33. Since these electrodes 11, 12, 24, 25, 26, 26, 32, 33 are partially embedded in the surface 67A (with slight protrusion at the surface 67A) of the tubular-shaped structure 67, accidental dislodgement of an individual electrode 11, 12, 24, 25, 26, 27, 32, 33 can be avoided. Being snugly filled inside the external ear canal 904 will help to avoid movement interference during EOG, EEG and ECG recordings. This will allow the wearer (user) 900 to move around freely while the EOG, EEG, ECG recordings are taking place.

In some embodiments, one or more components of the comprehensive at-home sleep monitoring system 103 may be configured to be housed in a tubular-shaped structure 67. All of the EEG electrodes 24, 25, 26, 27, and the EOG electrodes 11, 12, (and ECG electrodes 32, 33, if ECG system 30 is included) may be located at the surface 67A of the tubular-shaped structure 67 and so that all of the EEG electrodes 24, 25, 26, 27, EOG electrodes 11, 12, and ECG electrodes 32, 33, are housed in the tubular-shaped structure 67. (FIG. 16). In preferred embodiments, one or more of the EEG electrodes 24, 25, 26, 27, EOG electrodes 11, 12, and ECG electrodes 32, 33, is/are configured to be located at the upper surface 91 (upper surface 91 at approximately 90 degrees above horizontal level 92) of the tubular-shaped structure 67. In preferred embodiments, one or more of the electrodes 11, 12, 24, 25, 26, 27, 32, 33, is/are configured to be located at between 0 and 60 degrees, and more preferably at approximately 30 degrees (plus or minus 30 degrees) above the horizontal level 92 of the tubular-shaped structure 67 and is/are configured to face forward-upward direction 93. In preferred embodiments, one or more of the electrodes 11, 12, 24, 25, 26, 27, 32, 33, is/are configured to be located at between approximately 120 and 180 degrees, and more preferably at approximately 150 degrees (plus or minus 30 degrees) above the horizontal level 92 of the tubular-shaped structure 67 and is/are configured to face backward-upward direction 94. (Upper surface 91, horizontal level 92, forward, backward, upward, forward-upward direction 93, backward-upward direction 94, all refer to directions relative to the head 901 of the wearer 900 with the wearer 900 in an upright position after the tubular-shaped structure 67 has been inserted into a wearer's external ear canal 904.)

The most common pulse oximeters are transmittance (transmissive mode) pulse oximeters and they are usually worn on a thin body part like finger, toe or earlobe (lobule of ear). For the present invention, the pulse oximeter 71 may be a transmittance pulse oximeter 71B worn on the finger, toe, or earlobe, and the pulse oximeter 71 may be in electronic communication with the processing unit 50, 401. Alternatively, a light generator 41 and a light-detecting sensor 42 of a reflectance (reflective-mode) pulse oximeter may be incorporated into one of the following housing structures 60: an earbud-style structure 61, a behind-the-ear-hearing-aid-style structure 63 and a tubular-shaped structure 67 and be worn inside wearer's external ear canal 904. (FIGS. 2, 3, 14).

The comprehensive at-home sleep monitoring system 103 preferably further comprises a wired or wireless ear-canal pulse oximeter 71A. In some embodiments, a novel wired or wireless ear-canal pulse oximeter 71A comprises a wired or wireless light generator 41 and a wired or wireless light detecting sensor 42 of a reflectance pulse oximeter. The wired or wireless light generator 41 and the wired or wireless light detecting sensor 42 are mounted or located on one of the following: a surface 62A of a horizontal portion 62 of an earbud-style structure 61, a surface 66A of an in-the-ear portion 66 of a behind-the-ear-hearing-aid-style structure 63 or a surface 67A of a tubular-shaped structure 67. (Examples for wireless pulse oximeters currently available: Wireless pulse oximeters from Turner Medical, Colchester, Connecticut; or Nonin wireless pulse oximeter from Nonin Medical Inc. Plymouth, Minnesota.) The wired or wireless light generator 41 and the wired or wireless light-detecting sensor 42 of the ear-canal pulse oximeter 71A are configured to be coupled to the external ear canal 904 of a wearer's ear 902 to be in contact with the skin of the external ear canal 904 of the wearer's ear 902. The ear-canal pulse oximeter 71A may be a wired or wireless reflectance pulse oximeter having a reflectance oximeter module 40A in wired or wireless communication with the light generator 41 and the light detecting sensor 42. The reflectance oximeter module 40A is configured to record pulse data and blood oxygen saturation data of the wearer 900 by analyzing the data from the light generator 41 and the light detecting sensor 42. The ear-canal pulse oximeter 71A may be in wireless communication with a processing unit 50, 401, (preferably via a network interface 85 that is in communication with the reflectance oximeter module 40A).

In some embodiments, a novel wired or wireless ear-canal pulse oximeter 71A comprises a light generator 41, a light detecting sensor 42, and a detection module 45. The light generator 41 and the light detecting sensor 42 are housed in a housing structure 60 and are in electronic communication with the detection module 45. The detection module 45 is configured to analyze the data from the light generator 41 and the data from the light detecting sensor 42 to assess, determine, record, etc., the wearer's pulse data and blood oxygen saturation data. The ear-canal pulse oximeter 71A further comprises a network interface 85 and a display screen 404C, 89 (such as a display screen 404C on a client device 400 of a wearer 900 and/or a display screen 89 on the housing structure 60). The network interface 85 may be in electronic communication with the display screen 404C on a client device 400 and/or the display screen 89 on the housing structure 60. The network interface 85 is in electronic communication with the detection module 45. Preferably, the network interface 85 may be configured to send signals to the display screen 404C and the display screen 404C is configured to generate a visible notification (visual display) on the client device 400 of the wearer 900 describing the wearer's pulse data and blood oxygen saturation data. Optionally, the network interface 85 may be configured to send signals to the display screen 89 that is configured to generate a visible notification on the housing structure 60 describing the wearer's pulse data and blood oxygen saturation data. The light generator 41 and the light detecting sensor (photodiode) 42 of the reflectance oximeter module 40A and the display screen 89 may be configured to be housed in the housing structure 60 selected from one of the following: the surface 62A of an earbud-style structure 61, the surface 66A of an in-the-ear portion 66 of a behind-the-ear-hearing-aid-style structure 63 or the surface 67A of a tubular-shaped structure 67. The horizontal portion 62 of the earbud-style structure 61 or the in-the-ear portion of the behind-the-ear-hearing-aid-style structure 63 or the tubular-shaped structure 67 may be made with flexible elastic and adaptable material (e.g., ultra-soft silicone material or soft foam). The flexible elastic and adaptable material is configured to have appropriate flexibility, elasticity and adaptability such that the light generator 41 and light detecting sensor 42 of the ear-canal pulse oximeter 71A will be naturally in close contact with the skin of the wearer's external ear canal 904 when the horizontal portion 62 of the earbud-style structure 61 or the in-the-ear portion 66 of the behind-the-ear-hearing-aid-style structure 63 or the tubular-shaped structure 67 is inserted into the wearer's external ear canal 904. Wireless pulse oximeters are readily available. (Examples for wireless pulse oximeters available: Wireless pulse oximeters from Turner Medical, Colchester, Connecticut; or Nonin wireless pulse oximeter from Nonin Medical Inc. Plymouth, Minnesota.) The wireless ear-canal pulse oximeter 71A is preferably configured to be in wireless electronic communication with a processing unit 50, 401. Wireless ear-canal pulse oximeter 71A may be a component of a comprehensive sleep monitoring system 103. The conventional transmittance pulse oximeter 71B is usually put on the fingertips and that might interfere with the finger functions. The conventional transmittance pulse oximeter 71B may also be put on toes or lobule of ear but that might not be suitable for ambulatory use. The ear-canal pulse oximeter 71A of the present invention is hand-free, fully ambulatory and very ease for self-installation and self-removal. The soft foam or ultra-soft silicone-type material will facilitate steady uniform and easy installation of the light generator 41 and light detecting sensor 42. Being snugly filled inside the external ear canal 904 will help to avoid movement interference during pulse oximeter recording. This will allow the wearer (user) 900 to move around freely while the pulse oximeter monitoring is taking place. These advantages will be very useful for high-altitude travelers/climbers and for patients with asthma, chronic obstructive pulmonary disease (COPD) or heart failure.

Some smart watches (for example, Apple Watch after series 6) include reflectance pulse oximeter to measure the wearer's pulse data and oxygen saturation data from the wearer's wrist. However, difficulty to maintain a constant and uniform fitting of the watch's wrist band and wearer's arm movements often influence the accuracy of the readings. Potential inaccuracies are also a problem particularly for readings below 90%. Because of these drawbacks, Apple Watch pulse oximeter is generally not a perfect medical-grade device and it is mainly used for detecting the trends in blood oxygen saturation (SpO2). Due to these problems, wrist-based reflectance pulse oximeters (even though they are wearable) are usually used only for snapshot readings. They are not suitable for continuous real-time monitoring. The ear-canal pulse oximeter 71A of the present invention can solve these problems since ear-canal pulse oximeter 71A can avoid movement interference and can also avoid the pitfalls from variable and changing fitting. The ear-canal pulse oximeter 71A of the present invention is suitable for continuous real-time monitoring and will not interfere with hand functions, unlike the medical-grade transmittance fingertip pulse oximeters.

In some embodiments, a separate client device 400 may be used for housing of some of the components of this comprehensive at-home sleep monitoring system 103. For example, EEG recording module(s) 21, EOG recording module 10, ECG recording module 31 (if ECG system 30 is included) and the processing unit 401 may be housed in a wearable client device 400A, such as a watch-type structure which can be worn on wrist, or a portable smart-phone-type client device 400B which can be carried or put on a bedside table. The comprehensive at-home sleep monitoring system 103 may comprise wireless EEG electrodes 24, 25, 26, 27, wireless EOG electrodes 11, 12, and wireless ECG electrodes 32, 33, that may be configured to be housed in one of the following: an earbud-type structure 61, an in-the-ear portion 66 of a behind-the-ear-hearing-aid-style structure 63 or a tubular-shaped structure 67. (Wireless electrodes such as that described by Ryan Kaveh et al. in Nature Communications on Aug. 2, 2024. Wireless dry EEG electrodes are also available from Zeto, Inc. in Santa Clara, California). The EEG recording module 20 may have amplifiers and filters 22 that may comprise a wireless EEG amplifier, EOG recording module 10 may have amplifiers and filters 13 that may comprise a wireless EOG amplifier, and ECG recording module 31 may have amplifiers and filters 34 that may comprise a wireless ECG amplifier (such as those amplifiers made by the BIOPAC Systems, Inc. in Goleta, California), together with the processing unit 401 may be housed in a wearable watch-type client device 400A or a portable smartphone-type client device 400B.

Since the human external ear canal 904 is a small space, EOG electrodes 11, 12, EEG electrodes 24, 25, 26, 27, and ECG electrodes 32, 33, may comprise miniature electrodes. Sharing of the electrodes 11, 12, 24, 25, 26, 27, 32, 33, will further help to save space. At least two of the electrodes 11, 12, 24, 25, 26, 27, 32, 33, may be used or shared by an auricular EEG monitoring system 20, an auricular EOG system 101, and/or an auricular ECG recording module 31. For example, when using wired electrodes, two wires of a local interface 58 may connect these two shared electrodes 11, 12, 24, 25, 26, 27, 32, 33, to the EEG recording module 21, while two different wires of a local interface 58 may connect these two shared electrodes 11, 12, 24, 25, 26, 27, 32, 33, to the EOG recording module 10 and two other wires of a local interface 58 may connect these two shared electrodes 11, 12, 24, 25, 26, 27, 32, 33, to the ECG recording module 31. Alternatively, when using wireless electrodes, two shared wireless electrodes 11, 12, 24, 25, 26, 27, 32, 33 may be wirelessly connected with a wireless EEG amplifier 22, a wireless EOG amplifier 13 and a wireless ECG amplifier 34. Thus, two shared electrodes 11, 12, 24, 25, 26, 27, 32, 33, may be shared with the EEG 21, EOG 10, and ECG 31 recording modules. For example, at least two of the EEG electrodes 24, 25, 26, 27, may be configured to be used as EOG electrodes 11, 12, by an EOG recording module 10. As another example, at least two of the EEG electrodes 24, 25, 26, 27, may be configured to be used as ECG electrodes 32, 33, by an ECG recording module 31. Different amplifiers and different filters 13, 22, 34, may be used by the EOG recording module 10, the EEG recording module 21, and the ECG recording module 31 to obtain EEG data, EOG data and ECG data from these two shared electrodes 11, 12, 24, 25, 26, 27, 32, 33. At least two electrodes 11, 12, 24, 25, 26, 27, 32, 33, are needed for a single-lead ECG data recording although more than two ECG electrodes are needed for multi-lead ECG recording. At least two electrodes 11, 12, 24, 25, 26, 27, 32, 33, are needed for the usual EOG data recording by the EOG recording module 10 although more than two EOG electrodes may be needed to enhance sensitivity or for special extra-ocular movement recording. The EEG recording module 21 may be in wired or wireless electronic communication 19 with at least two electrodes 11, 12, 24, 25, 26, 27, 32, 33, but preferably more than two electrodes for EEG data recording. Alternatively, the EEG recording module 21 may be in wired or wireless electronic communication 19 with multiple electrodes 11, 12, 24, 25, 26, 27, 32, 33, to provide multi-channel EEG data recording. Since the earbud-style structure 61 must be of small size in order to be inserted into the external ear canal 904, the EEG 21, ECG 31, and EOG 10 recording modules sharing two electrodes 11, 12, 24, 25, 26, 27, 32, 33, would help to save space.

The sleep monitoring by conventional at-home sleep monitoring systems is not very accurate because they use other parameters to "guess" the sleep stages. These conventional at-home sleep monitoring systems do not have EEG, making them unable to accurately monitor the sleep stages. They also do not have EOG and thus are unable to assess REM sleep accurately. With auricular EEG functionality and auricular EOG functionality of the present invention, this comprehensive at-home sleep monitoring system 103 is much more accurate.

The comprehensive at-home sleep monitoring system 103 may collect nearly all of the data as traditional polysomnogram (PSG) does. This comprehensive at-home sleep monitoring system 103 may be more accurate than the traditional PSG since wearer 900 of this comprehensive at-home sleep monitoring system 103 may sleep in the wearer's own bedroom while user of polysomnogram sleeps in a sleep center or a medical facility. This comprehensive at-home sleep monitoring system 103 is much more convenient and much less expensive. It has another advantage that it could automatically notify the wearer 900 to change sleep position or adjust the CPAP or anti-snoring oral device (if the wearer uses a CPAP or an anti-snoring oral device) on the spot when obstructive sleep apnea (OSA) is detected. Another advantage is that it can be self-installed and self-removed for repeated nightly use for long-term. This will be particularly helpful for patients with OSA since OSA is a long-term problem.

In some embodiments, a comprehensive sleep monitoring system 103 may be configured as a health monitoring system that is configured to monitor the wearer's health profiles when the wearer 900 is not sleeping, and the wearer's health profiles may include an extra-ocular eye movement profile of the wearer 900 and an electroencephalographic profile of the wearer 900. The processing unit 50, 401, is configured to analyze the EOG data as recorded by an EOG recording module 10 and the EEG data as recorded by the EEG recording module 21 to assess the extra-ocular eye movement profile of the wearer 900 and the electroencephalographic profile of the wearer 900. Alternatively, the wearer's health profiles may include one or more of the following: an extra-ocular eye movement profile of the wearer, an electroencephalographic profile of the wearer, an electrocardiographic profile of the wearer and a pulse and blood oxygen saturation profile of the wearer. The processing unit 50, 401, may be configured to analyze one or more of the following: the EOG data as recorded by an EOG recording module 10, the EEG data as recorded by an EEG recording module 21, the ECG data as recorded by an ECG recording module 31 and the pulse data and blood oxygen saturation data as recorded by the ear-canal pulse oximeter 71A to assess one or more of the following: the extra-ocular eye movement profile of the wearer, the electroencephalographic profile of the wearer, the electrocardiographic profile of the wearer and pulse profile and blood oxygen saturation profile of the wearer.

A Fifth Preferred Embodiment

In some embodiments, the present invention may comprise a novel auricular health monitoring system 104 and/or a novel auricular hybrid brain-computer interface (hBCI) system 105. The auricular health monitoring system 104 may be configured mainly for monitoring of health conditions. The auricular hybrid brain-computer interface system 105 (with auricular EEG monitoring system 20 and auricular EOG system 101) may comprise a processing unit configured to analyze and process the EEG data and EOG data to guide a hybrid brain-computer interface (hBCI) system, to be used in control of robotic arms or legs, control of wheelchair, control of gaming devices and control of cursors or keyboard of computer etc.

In some embodiments, novel auricular health monitoring systems 104 may comprise an auricular health surveillance complex that may include one or more (and more preferably at least two or more) of the following health-relevant monitoring systems in various combinations: an auricular electroencephalogram (EEG) monitoring system 20, an auricular electrooculogram (EOG) system 101, an auricular electrocardiogram (ECG) system 30, and an ear-canal pulse oximeter 71A. Each of these or a combination of these may form an auricular health monitoring system 104. Using a single location to monitor various physiological functions of the human body is one of the novel features of this invention. Combining EEG, EOG and ECG into a single monitoring system will provide easy convenient monitoring of very important health conditions and will provide significant advantage since simultaneous EEG/EOG/ECG recordings might help to improve accuracy as compared with EEG, EOG or ECG alone (or separately) by enhancing artifacts detection and by digital subtraction of other's interferences. Combining EEG/EOG/ECG into a single device will make it much easier to use the advanced algorithms and processing techniques in digital subtraction (digital subtraction as known in the art).

In some embodiments, an auricular health monitoring system 104 may comprise an auricular health surveillance complex that may include an auricular electrocardiogram (ECG) system 30 and an auricular electroencephalogram (EEG) monitoring system 20. The auricular health monitoring system 104 may further comprise a processing unit 50, 401. The auricular ECG system 30 comprises an auricular ECG recording module 31 that may comprise at least two wired or wireless ECG electrodes 32, 33, that are in wired or wireless electronic communication 19 with the ECG recording module 31. The ECG electrodes 32, 33, may be configured to be coupled to a wearer's first ear 902 or a peri-auricular area 903 around the wearer's first ear. When the ECG electrodes 32, 33, are coupled to the wearer's first ear 902 or the peri-auricular area around the wearer's first ear 903 the ECG electrodes 32, 33, are positioned in contact with separate locations on an area of the wearer 900, in which the area comprises at least one of the following: external ear 902 of the wearer's first ear, external ear canal 904 of the wearer's first ear, and the peri-auricular area 903 around the wearer's first ear, and the ECG recording module 31 may be configured to record ECG data of the wearer 900 via the ECG electrodes 32, 33. The auricular EEG monitoring system 20 may comprise a first EEG recording module 21. The first EEG recording module 21 may comprise a first set of a plurality of wired or wireless EEG electrodes 24, 25, 26, 27. Each electrode 24, 25, 26, 27, of the first set EEG electrodes 24, 25, 26, 27 is in wired or wireless electronic communication 19 with the first EEG recording module 21. The first set EEG electrodes 24, 25, 26, 27, may be configured to be coupled to the wearer's first ear 902 or the peri-auricular area 903 around the wearer's first ear 902. When the first set EEG electrodes 24, 25, 26, 27, are coupled to the wearer's first ear 902 or the peri-auricular area 903 around the wearer's first ear the first set EEG electrodes 24, 25, 26, 27, are positioned in contact with separate locations on an area of the wearer 900, in which the area comprises at least one of the following: external ear 902 of the wearer's first ear, external ear canal 904 of the wearer's first ear, and the peri-auricular area 903 around the wearer's first ear, and the first EEG recording module 21 is configured to record EEG data of the wearer 900 via the first set EEG electrodes 24, 25, 26, 27. The auricular ECG recording module 31 and the auricular EEG monitoring system 20 (together with the first EEG recording module 21) may be in wired or wireless electronic communication 19 with the processing unit 50, 401. The processing unit 50, 401, may be configured to analyze the ECG data recorded by the auricular ECG recording module 31 and the EEG data recorded by the first EEG recording module 21 to assess the wearer's health profile, and the wearer's health profile preferably includes an electrocardiographic profile of the wearer 900 and an electroencephalographic profile of the wearer 900. Each of the two wired or wireless ECG electrodes 32, 33 and each of the first set EEG electrodes 24, 25, 26, 27, are configured to be housed in a housing structure 60. The auricular health monitoring system 104 preferably further comprises a network interface 85 and a display screen 89, 404C (such as a display screen 89 on the housing structure 60 and/or a display screen 404C on a client device 400). The network interface 85 is in electronic communication with the processing unit 50, 401, and the display screen 89, 404C. The network interface 85 is configured to generate a visible notification to the display screen 89 on the housing structure 60 and/or the display screen 404C on a client device 400 of the wearer 900 describing the wearer's electrocardiographic profile and electroencephalographic profile. (FIGS. 4, 10, 11, 23). (For example, the display screen 89 on the housing structure 60 may show very brief visible information to remind the wearer 900 to see more detailed visible information on the display screen 404C on the client device 400 of the wearer 900). Optionally, the auricular EEG monitoring system 20 may further comprise a second EEG recording module 21 that may be in wired or wireless electronic communication 19 with a second set of a plurality of wired or wireless EEG electrodes 24, 25, 26, 27, that are coupled to a second ear 902 of the wearer 900 or a peri-auricular area 903 around the wearer's second ear. When the second set EEG electrodes 24, 25, 26, 27, are coupled to the wearer's second ear 902 or the peri-auricular area 903 around the wearer's second ear the second set EEG electrodes 24, 25, 26, 27, are positioned in contact with separate locations on an area of the wearer 900, in which the area comprises at least one of the following: external ear 902 of the wearer's second ear, external ear canal 904 of the wearer's second ear, and the peri-auricular area 903 around the wearer's second ear, and the second EEG recording module 21 is configured to record EEG data of the wearer 900 via the second set EEG electrodes 24, 25, 26, 27. The second EEG recording module 21 is in wired or wireless (preferably wireless) electronic communication 19 with the processing unit 50, 401, similar to descriptions hereinbefore. The processing nit 50, 401, is configured to analyze EEG data from both the first and the second EEG recording modules 21 to obtain the wearer's 900 EEG profile from both sides of the wearer's 900 brain.

In some embodiments, an auricular health monitoring system 104 may comprise an auricular health surveillance complex that may include an auricular electrocardiogram (ECG) system 30, an auricular electroencephalogram (EEG) monitoring system 20 and an auricular electrooculogram (EOG) system 101. The auricular ECG system 30 and the auricular EEG monitoring system 20 are as described hereinbefore. The auricular EOG system 101 comprises an EOG recording module 10. The EOG recording module 10 may be in wired or wireless electronic communication 19 with at least two wired or wireless EOG electrodes 11, 12. The EOG electrodes 11, 12, may be configured to be coupled to a wearer's first ear 902 or a peri-auricular area 903 around the wearer's first ear. When the EOG electrodes 11, 12, are coupled to the wearer's first ear 902 or the peri-auricular area 903 around the wearer's first ear the EOG electrodes 11, 12, are positioned in contact with separate locations on an area of the wearer 900, the area comprising at least one of the following: external ear 902 of the wearer's first ear, external ear canal 904 of the wearer's first ear, and the peri-auricular area 903 around the wearer's first ear. The EOG recording module 10 may be configured to record EOG data of the wearer 900 via the EOG electrodes 11, 12. The EOG recording module 10 is in wired or wireless electronic communication 19 with a processing unit 50, 401, and the processing unit 50, 401, is configured to analyze the ECG data recorded by the ECG recording module 31, the EEG data recorded by the EEG recording module 21, and the EOG data recorded by the EOG recording module 10 to assess the wearer's health profile. The wearer's health profile preferably includes the electrocardiographic profile of the wearer 900, the electroencephalographic profile of the wearer 900, and an electrooculographic profile of the wearer 900.

Figure 23:
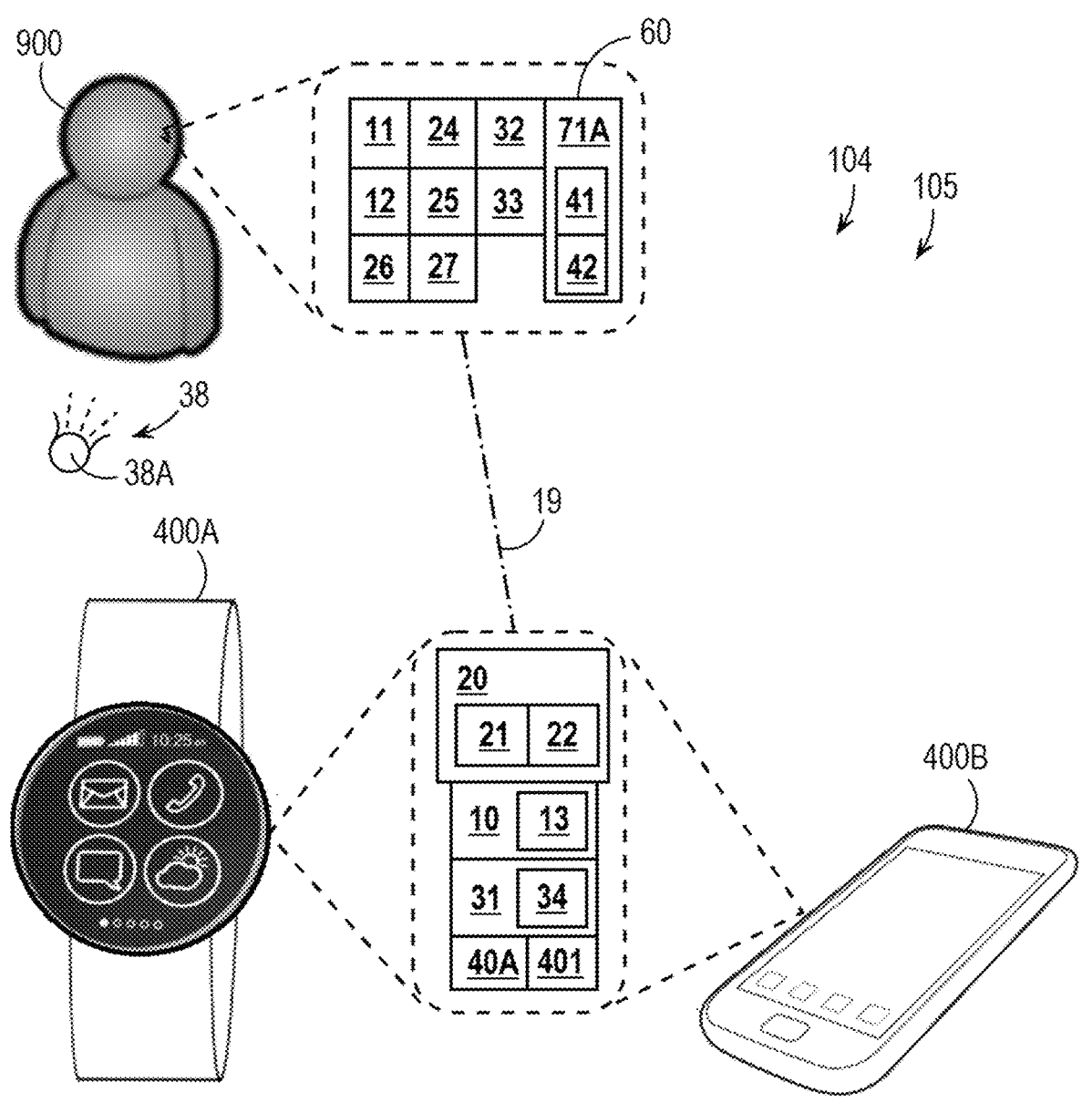
FIG. 23-FIG. 23 illustrates a schematic diagram of some exemplary components of another example of an auricular health monitoring system and an auricular hybrid brain-computer interface system according to various embodiments described herein.

In some embodiments, an auricular health monitoring system 104 may comprise an auricular health surveillance complex that may include an auricular electrocardiogram (ECG) system 30, an auricular electroencephalogram (EEG) monitoring system 20 and an ear-canal pulse oximeter 71A. The auricular ECG system 30 and the auricular EEG monitoring system 20 are as described hereinbefore. Preferably, the ear-canal pulse oximeter 71A may be a reflectance pulse oximeter having a reflectance oximeter module 40A. The reflectance oximeter module 40A may comprise a wired or wireless light generator 41, a wired or wireless light detecting sensor 42, and a detection module 45. The light generator 41 and light detecting sensor 42 may be configured to be coupled to the external ear canal 904 of a wearer's first ear 902 to be in contact with the skin of the external ear canal 904 of the wearer's first ear 902. The light generator 41 preferably includes light-emitting diode configured to emit light of different wavelengths, and the light detecting sensor 42 is configured to measure the absorption of light of different wavelengths by the wearer's skin, including red and infrared wavelengths. The detection module 45 is in wired or wireless electronic communication 19 with the light generator 41 and the light detecting sensor 42, and the detection module 45 is configured to analyze the data transmitted from the light generator 41 and data transmitted from the light detecting sensor 42 to record the wearer's pulse data and blood oxygen saturation data. The ear-canal pulse oximeter 71A may be in wireless communication with a processing unit 50, 401, and the processing unit 50, 401, is configured to analyze the ECG data recorded by the ECG recording module 31, the EEG data recorded by the EEG recording module 21, and the wearer's pulse data and blood oxygen saturation data recorded by the ear-canal pulse oximeter 71A to assess the wearer's health profile. The wearer's health profile preferably includes one or more of the electrocardiographic profile of the wearer 900, electroencephalographic profile of the wearer 900, and the wearer's pulse data and blood oxygen saturation data. The auricular health monitoring system 104 preferably further comprises a network interface 85 and a display screen 89, 404C (such as a display screen 89 on the housing structure 60 and/or a display screen 404C on a client device 400). The network interface 85 is in electronic communication with the processing unit 50, 401, and the display screen 89, 404C. Preferably, the network interface 85 is configured to send signals to the display screen 404C that is configured to generate a visible notification on the client device 400 of the wearer 900 describing the wearer's electrocardiographic profile, electroencephalographic profile, pulse data and blood oxygen saturation data. Optionally, the network interface 85 is configured to send signals to the display screen 89 that is configured to generate a visible notification on the housing structure 60 describing the wearer's electrocardiographic profile, electroencephalographic profile, pulse data and blood oxygen saturation data and/or profile. (FIGS. 14, 23). (For example, the display screen 89 on the housing structure 60 may show very brief visible information to remind the wearer 900 to see more detailed visible information on the display screen 404C on the client device 400 of the wearer 900).

In some embodiments, an auricular health monitoring system 104 may comprise an auricular health surveillance complex that may include at least one or more (and preferably at least two or more) of the following health-relevant monitoring systems: an auricular EEG monitoring system 20, an auricular EOG system 101, an auricular ECG system 30, and an ear-canal pulse oximeter 71A. Each of these health-relevant monitoring systems or a combination of these health-relevant monitoring systems may form an auricular health monitoring system 104. In some embodiments, an auricular health monitoring system 104 may have an auricular health surveillance complex that may comprise at least two of the health-relevant monitoring systems. In some embodiments, an auricular health monitoring system 104 may have an auricular health surveillance complex that may comprise all of the following health-relevant monitoring systems: an auricular EEG monitoring system 20, an auricular EOG system 101, an auricular ECG system 30 and an ear-canal pulse oximeter 71A. The auricular EEG monitoring system 20 (with EEG recording module 21), the auricular ECG system 30 (with ECG recording module 31), the auricular EOG system 101 (with EOG recording module 10) and the ear-canal pulse oximeter 71A are as described hereinbefore. All of the EEG electrodes 24, 25, 26, 27, the EOG electrodes 11, 12, the ECG electrodes 32, 33, the light generator 41 and the light-detecting sensor 42 of the ear-canal pulse oximeter 71A may be housed in one of the following housing structures 60: a horizontal portion 62 of an earbud style structure 61, an in-the-ear-portion 66 of a behind-the-ear-hearing-aid-style structure 63, and a tubular-shaped structure 67. The horizontal portion 62 of the earbud-style structure 61, the in-the-ear-portion 66 of the behind-the-ear-hearing-aid-style structure 63 and the tubular-shaped structure 67 may be made with an elastic flexible and adaptable material (for example: soft foam or ultra-soft silicone type material such as pacifier-grade silicone), such that the elastic flexible and adaptable material is configured to have appropriate elasticity, flexibility and adaptability such that the horizontal portion 62 of the earbud-style structure 61, the in-the-ear-portion 66 of the behind-the-ear-hearing-aid-style structure 63 and the tubular-shaped structure 67 will naturally adapt to the contour of the wearer's external ear canal 904 and snugly fill the interior of the external ear canal 904 when they are inserted into the wearer's external ear canal 904. All of the electrodes 11, 12, 24, 25, 26, 27, 32, 33, and the light generator 41 and the light detecting sensor 42 of the ear-canal pulse oximeter may be configured to be partially embedded in the surface 62A of the horizontal portion 62 with slight protrusion at the surface 62A of the horizontal portion 62 of the earbud-style structure 61 such that all of these electrodes 11, 12, 24, 25, 26, 27, 32, 33, and the light generator 41 and the light-detecting sensor 42 of the ear-canal pulse oximeter will be naturally and snugly in contact with the skin of the wearer's external ear canal 904 when the horizontal portion 62 of the earbud-style structure 61 is inserted into the wearer's external ear canal

904. All of the electrodes 11, 12, 24, 25, 26, 27, 32, 33, and the light generator 41 and the light-detecting sensor 42 of the ear-canal pulse oximeter may be configured to be partially embedded in the surface 66A of the in-the-ear portion with slight protrusion at the surface 66A of the in-the-ear portion 66 of the behind-the-ear-hearing-aid-style structure 63 such that all of these electrodes 11, 12, 24, 25, 26, 27, 32, 33, and the light generator 41 and the light-detecting sensor 42 of the ear-canal pulse oximeter will be naturally and snugly in contact with the skin of the wearer's external ear canal 904 when the in-the-ear portion 66 of the behind-the-ear-hearing-aid-style structure 63 is inserted into the wearer's external ear canal 904. All of the electrodes 11, 12, 24, 25, 26, 27, 32, 33, and the light generator 41 and the light-detecting sensor 42 of the ear-canal pulse oximeter may be configured to be partially embedded in the surface 67A of the tubular-shapes structure 67 with slight protrusion at the surface 67A of the tubular shaped structure 67 such that all of these electrodes 11, 12, 24, 25, 26, 27, 32, 33, and the light generator 41 and the light-detecting sensor 42 of the ear-canal pulse oximeter will be naturally and snugly in contact with the skin of the wearer's external ear canal 904 when the tubular-shaped structure 67 is inserted into the wearer's external ear canal 904. Installing and removing these electrodes 11, 12, 24, 25, 26, 27, 32, 33, and the light generator 41 and the light-detecting sensor 42 of the ear-canal pulse oximeter will be as easy as inserting and removing the earbud-style structure 61, the behind-the-ear-hearing-aid-style structure 63 and the tubular-shaped structure 67 from the wearer's external ear canal 904. This set-up of partially embedded (with slight protrusion at the surface) electrodes 11, 12, 24, 25, 26, 27, 32, 33, and partially embedded light generator 41 and the light-detecting sensor 42 of the ear-canal pulse oximeter and the flexibility, elasticity and adaptability of the material will allow all of these electrodes 11, 12, 24, 25, 26, 27, 32, 33, and the light generator 41 and light detecting sensor 42 to be naturally and snugly in close contact with the skin of the wearer's external ear canal 904 and also allow very easy self-installation and self-removal. There will be no need for a certified technologist to apply the electrodes 11, 12, 24, 25, 26, 27, 32, 33. Applying adhesive material to secure these electrodes 11, 12, 24, 25, 26, 27, 32, 33, will be unnecessary. An auricular health monitoring system 104, including EEG 20, ECG 30, EOG 101 and ear-canal pulse oximeter 71A would provide several advantages, including easy self-installation, self-removal and repeated daily uses. Besides easiness, convenience, free mobility and comprehensiveness, simultaneous EEG/EOG/ECG recordings might help to improve accuracy as compared with EEG, EOG or ECG alone (or separately) by enhancing artifacts detection and by digital subtraction of other's interferences, using advanced algorithms and signal processing techniques to identify and remove artifact signals effectively. (digital subtraction as known in the art).

In some embodiments, a separate client device 400 may be used for housing of some of the components of this auricular health monitoring system 104. For example, EEG recording module 21 (if auricular EEG monitoring system 20 is incorporated), ECG recording module 31 (if auricular ECG system 30 is incorporated), EOG recording module 10 (if auricular EOG system 101 is incorporated), reflectance oximeter module 40A (if ear-canal pulse oximeter 71A is incorporated) and the processing unit 401 may be housed in a wearable client device 400A, such as a watch-type structure which can be worn on wrist, or a portable smart-phone-type client device 400B which can be carried or put on a nearby table. The auricular health monitoring system 104 may comprise wireless EEG electrodes 24, 25, 26, 27, (if auricular EEG monitoring system 20 is incorporated), wireless EOG electrodes 11, 12, (if auricular EOG system 101 is incorporated) wireless ECG electrodes 32, 33, (if auricular ECG system 30 is incorporated) and wireless light generator 41 and wireless light-detecting sensor 42 (if ear-canal pulse oximeter 71A is incorporated) that may be configured to be housed in one of the following: an earbud-type structure 61 or an in-the-ear portion 66 of a behind-the-ear-hearing-aid-style structure 63 or a tubular-shaped structure 67. (Wireless electrodes such as that described by Ryan Kaveh et al. in Nature Communications on Aug. 2, 2024. Wireless dry EEG electrodes are also available from Zeto, Inc. in Santa Clara, California). The EEG recording module 20 may have amplifiers and filters 22 that may comprise a wireless EEG amplifier, EOG recording module 10 may have amplifiers and filters 13 that may comprise a wireless EOG amplifier, and ECG recording module 31 may have amplifiers and filters 34 that may comprise a wireless ECG amplifier (such as those amplifiers made by the BIOPAC Systems, Inc. in Goleta, California), together with the reflectance oximeter module 40A and the processing unit 401 may be housed in a wearable watch-type client device 400A or a portable smart-phone-type client device 400B.

In some embodiments, an auricular health monitoring system 104 may comprise at least one of the following: an auricular EEG monitoring system 20 (with EEG recording module 21), an auricular ECG system 30 (with ECG recording module 31), an auricular EOG system 101 (with EOG recording module 10) and an ear-canal pulse oximeter 71A. The auricular EEG monitoring system 20 is configured to assess (or record or determine) the wearer's EEG profile. The auricular ECG system 30 is configured to assess (or record or determine) the wearer's ECG profile, The auricular EOG system 101 is configured to assess (or record or determine) the wearer's EOG profile. The ear-canal pulse oximeter 71A is configured to assess (or record) the wearer's pulse profile and blood oxygen saturation profile. (EEG system 20, ECG system 30, EOG system 101 and ear-canal pulse oximeter 71A are as described hereinbefore.) The auricular health monitoring system 104 further comprises a network interface 85, 406, and at least one of the following: a speaker 86, 404A, a vibrator 87, 404B, and a display screen 89, 404C (such as a display screen 404C on a client device 400 of the wearer 900 and/or a display screen 89 on a housing structure 60). Preferably, a speaker 86, 404A, a vibrator 87, 404B, and/or a display screen 89, 404C is in electronic communication with the network interface 85, 406. The processing unit 50, 401 is configured to send electronic signals to the network interface 85, 406. Preferably, the network interface 85, 406 is configured to send signals to the display screen 404C which is configured to generate a visible notification on the client device 400 of the wearer 900 describing the wearer's EOG profile, EEG profile, ECG profile, pulse profile and blood oxygen saturation profile. Optionally, the network interface 85, 406 is configured to send signals to the display screen 89 that is configured to generate a visible notification on the housing structure 60 describing the wearer's EOG profile, EEG profile, ECG profile, pulse profile and blood oxygen saturation profile. (For example, the display screen 89 on the housing structure 60 may show very brief visible information to remind the wearer 900 to see more detailed visible information on the display screen 404C on the client device 400 of the wearer 900). Combining EOG 101, EEG 20 and ECG 30 into a single monitoring system will provide easy convenient monitoring of very important health conditions and will provide significant advantage since simultaneous EEG/EOG/ECG recordings might help to improve accuracy as compared with EEG, EOG or ECG alone (or separately) by enhancing artifacts detection and by digital subtraction of other's interferences. (It is well known that ECG artifacts and eye movement artifacts often interfere with recording and interpretation of EEG and vice versa). Combining EEG/EOG/ECG into a single device will make it much easier to use the advanced algorithms and processing techniques in digital subtraction. Using a single location to monitor various physiological functions of the human body is one of the novel features of this invention. Modern technology, like independent component analysis (ICA) can also be more easily applied for removal of artifacts (for example removing eye blink artifacts from EEG recordings or removing ECG signals from EEG recordings) when EEG/EOG/ECG are combined into a single device. The human external ear canal 904 is a very unique location where EOG, EEG and ECG can be easily combined and function together and they can be effortlessly self-installed and self-removed In some embodiments, an auricular hybrid brain-computer interface system 105 may include an auricular EOG system 101 (having at least one EOG recording module 10), an auricular electroencephalogram (EEG) monitoring system 20 (having at least one EEG recording module 21), and a processing unit 50, 401. The auricular EOG system 101 may comprise a first EOG recording module 10 preferably includes a first set of at least two wired or wireless EOG electrodes 11,12, in wired or wireless electronic communication 19 with the first EOG recording module 10. All of the first set EOG electrodes 11, 12, may be configured to be coupled to a first ear 902 of a wearer 900 or a peri-auricular area 903 around the wearer's first ear 902. When the first set EOG electrodes 11,12, are coupled to the wearer's first ear 902 or the peri-auricular area 903 around the wearer's first ear all of the first set EOG electrodes 11, 12, are positioned in contact with separate locations on an area of the wearer 900, in which the area may be at least one of the following: external ear of the wearer's first ear 902, external ear canal 904 of the wearer's first ear, and the peri-auricular area 903 around the wearer's first ear. The first EOG recording module 10 may be configured to record EOG data of the wearer via the first set EOG electrodes 11, 12. The auricular electroencephalogram (EEG) monitoring system 20 may have a first EEG recording module 21. The first EEG recording module 21 includes a first set of a plurality of wired or wireless EEG electrodes 24, 25, 26, 27. The first set EEG electrodes 24, 25, 26, 27, are configured to be coupled to the wearer's first ear 902 or the peri-auricular area 903 around the wearer's first ear, and the first EEG recording module 21 may be in wired or wireless electronic communication with all of the first set EEG electrodes 24, 25, 26, 27. When the first set EEG electrodes 24, 25, 26, 27, are coupled to the wearer's first ear 902 or the peri-auricular area 903 around the wearer's first ear all of the first set EEG electrodes 24, 25, 26, 27, are positioned in contact with separate locations on an area of the wearer 900, in which the area may be at least one of the following: external ear 902 of the wearer's first ear, external ear canal 904 of the wearer's first ear, and the peri-auricular area 903 around the wearer's first ear. The EEG recording module 21 may be configured to record EEG data of the wearer via the first set EEG electrodes 24, 25, 26, 27. The processing unit 50, 401, is configured to analyze the EOG data as recorded by the first EOG recording modules 10 and the EEG data as recorded by the first EEG recording modules 21 and the processing unit is further configured to process the EOG data recorded by the first EOG recording module 10 and the EEG data recorded by the first EEG recording module 21 to guide the auricular hybrid brain-computer interface (hBCI) system 105, utilizing hBCI algorithms (known in the art).

Optionally, the auricular hybrid brain-computer interface (hBCI) system 105 may include an auricular EEG monitoring system 20 that may comprise two sets of EEG recording modules 21. The first EEG recording module 21 is as described hereinbefore. The second EEG recording module 21 is similar to the aforementioned first EEG recording module 21. The second EEG recording module 21 is in electronic communication with a second set of a plurality of wired or wireless EEG electrodes 24, 25, 26, 27. The second set EEG electrodes 24, 25, 26, 27, are configured to be coupled to a wearer's second ear 902 or a peri-auricular area 903 around the wearer's second ear. The second EEG recording module 21 is configured to record EEG via the second set EEG electrodes, 24, 25, 26, 27 and the second EEG recording module 21 is in wired or wireless electronic communication with the processing unit 50, 401. The second EEG recording module 21 may be in wired or wireless (preferably wireless) electronic communication with all of the second set EEG electrodes 24, 25, 26, 27. When the second set EEG electrodes 24, 25, 26, 27, are coupled to the wearer's second ear 902 or the peri-auricular area 903 around the wearer's second ear all of the second set EEG electrodes 24, 25, 26, 27, are positioned in contact with separate locations on an area of the wearer 900, in which the area may be at least one of the following: external ear 902 of the wearer's second ear, external ear canal 904 of the wearer's second ear, and the peri-auricular area 903 around the wearer's second ear. The second EEG recording module 21 may be configured to record EEG data of the wearer via the second set EEG electrodes 24, 25, 26, 27. The auricular hybrid brain-computer interface system 105 may comprises one or two sets of EOG recording modules 10. Optionally, in some embodiments, an auricular EOG system 101 may comprise two EOG recording modules 10 that may be utilized by a wearer 900, with the first set of at least two EOG electrodes 11, 12, (in electronic communication with the first EOG recording module 10) being positioned in contact with separate locations on an area of the wearer 900, in which the area may be at least one of the following: external ear 902 of the wearer's first ear, external ear canal 904 of the wearer's first ear, and the peri-auricular area 903 around the wearer's first ear. The second EOG recording module 10 is in electronic communication with each EOG electrode of the second set of at least two EOG electrodes 11, 12. The second set of at least two EOG electrodes are positioned in contact with separate locations on an area of the wearer 900, in which the area may be at least one of the following: external ear 902 of the wearer's second ear, external ear canal 904 of the wearer's second ear, and the peri-auricular area 903 around the wearer's second ear. The first EOG recording module 10 is configured to record EOG data via the first set of at least two EOG electrodes 11,12 and the second EOG recording module 10 is configured to record EOG data via the second set of at least two EOG electrodes, similar to descriptions hereinbefore. Preferably, the EOG electrodes 11, 12, of these two EOG recording modules 10 are placed in mirror-image way in regard to heights depths and sequence. For example, for the first set EOG electrodes 11, 12, the inner (deeper) EOG electrode 11, 12, may be placed on the upper surface of the horizontal portion 62 of the earbud-style structure 61, while the outer (less deep) EOG electrode 11, 12, may be placed on the anterior surface of the horizontal portion 62 of the earbud-style structure 61. For the second set EOG electrodes 11, 12, the inner (deeper) EOG electrode 11, 12, may be also placed on the upper surface of the horizontal portion 62 of the earbud-style structure 61 while the outer (less deep) EOG electrode 11, 12, may be placed on the anterior surface of the earbud-style structure 61. Since the two human eyes are usually making conjugate movements, these two EOG recording modules 10 may record similar EOG results. Nevertheless. the mirror-image locations of the bilateral EOG electrodes 11, 12, may enhance the sensitivity for these two sets of EOG electrode 11, 12, to pick up more accurate data of extra-ocular movements. The auricular hybrid brain-computer interface system 105 may comprises one or two sets of EEG recording modules 21 and one or two sets of EOG recording modules 10. The first EOG recording module 10 and the first EEG recording module 21 may be in wired or wireless electronic communication 19 with the processing unit 50, 401. Preferably, the second EOG recording module 10 and the second EEG recording module 21 are in wireless electronic communication with the processing unit 50, 401. The processing unit 50, 401, may be configured to analyze the EOG data recorded by at least one of the first and the second EOG recording module(s) 10 and the EEG data recorded by at least one of the first and the second EEG recording module (s) 21 to assess (or record or determine) the wearer's health profile, in which the wearer's health profile includes an electrooculographic profile of the wearer and an electroencephalographic profile of the wearer 900. The processing unit 50, 401, is further configured to analyze the EOG data as recorded by at least one of the first and second EOG recording module(s) 10 and the EEG data as recorded by at least one of the first and the second EEG recording module (s) 21 and the processing unit is further configured to process the EOG data recorded by at least one of the first and second EOG recording module(s) 10 and the EEG data recorded by at least one of the first and second EEG recording module(s) 21 to guide the auricular hybrid brain-computer interface (hBCI) system 105.

Optionally, the auricular hybrid brain-computer interface system 105 (auricular hBCI system 105) may further comprise an auricular electrocardiogram (ECG) system 30. (Auricular ECG system 30 as described hereinbefore.) Although ECG is usually not needed in brain-computer interface (BCI) and robotics, there is significant advantage to include auricular ECG system 30 (with auricular ECG recording module 31) into the auricular hBCI system 105 because it can help to identify and remove cardiac artifacts from the EEG and EOG recordings.

In some embodiments, an auricular hBCI system 105 may comprise an auricular EEG monitoring system 20 (with EEG recording module 21) and an auricular EOG system 101 (with EOG recording module 10). In some embodiments, all of the EEG electrodes 24, 25, 26, 27, and the EOG electrodes 11, 12, may be housed in a housing structure 60, selected from one of the following: a horizontal portion 62 of an earbud style structure 61, an in-the-ear-portion 66 of a behind-the-ear-hearing-aid-style structure 63, and a tubular-shaped structure 67. The horizontal portion 62 of the earbud-style structure 61, the in-the-ear-portion 66 of the behind-the-ear-hearing-aid-style structure 63 and the tubular-shaped structure 67 may be made with an elastic flexible and adaptable material (for example: soft foam or ultra-soft silicone type material such as pacifier-grade silicone), such that the elastic flexible and adaptable material is configured to have appropriate elasticity, flexibility and adaptability such that the horizontal portion 62 of the earbud-style structure 61, the in-the-ear-portion 66 of the behind-the-ear-hearing-aid-style structure 63 and the tubular-shaped structure 67 will naturally adapt to the contour of the wearer's external ear canal 904 and snugly fill the interior of the external ear canal 904 when they are inserted into the wearer's external ear canal 904. All of the EOG electrodes, 11, 12, and the EEG electrodes 24, 25, 26, 27, may be configured to be partially embedded in the surface 62A of the horizontal portion 62 with slight protrusion at the surface 62A of the horizontal portion 62 of the earbud-style structure 61 such that all of these electrodes 11, 12, 24, 25, 26, 27, will be naturally and snugly in contact with the skin of the wearer's external ear canal 904 when the horizontal portion 62 of the earbud-style structure 61 is inserted into the wearer's external ear canal 904. All of the electrodes 11, 12, 24, 25, 26, 27, may be configured to be partially embedded in the surface 66A of the in-the-ear portion with slight protrusion at the surface 66A of the in-the-ear portion 66 of the behind-the-ear-hearing-aid-style structure 63 such that all of these electrodes 11, 12, 24, 25, 26, 27, will be naturally and snugly in contact with the skin of the wearer's external ear canal 904 when the in-the-ear portion 66 of the behind-the-ear-hearing-aid-style structure 63 is inserted into the wearer's external ear canal 904. All of the electrodes 11, 12, 24, 25, 26, 27, may be configured to be partially embedded in the surface 67A of the tubular-shaped structure 67 with slight protrusion at the surface 67A of the tubular shaped structure 67 such that all of these electrodes 11, 12, 24, 25, 26, 27, will be naturally and snugly in contact with the skin of the wearer's external ear canal 904 when the tubular-shaped structure 67 is inserted into the wearer's external ear canal 904. Installing and removing these electrodes 11, 12, 24, 25, 26, 27, will be as easy as inserting and removing the earbud-style structure 61, the behind-the-ear-hearing-aid-style structure 63 and the tubular-shaped structure 67 from the wearer's external ear canal 904. There will be no need for a certified technologist to apply the electrodes 11, 12, 24, 25, 26, 27. Applying adhesive material to secure these electrodes 11, 12, 24, 25, 26, 27, will be unnecessary.

In some embodiments, a separate client device 400 may be used for housing of some of the components of this auricular hybrid brain-computer interface system 105. For example, the EEG recording module 21 and the EOG recording module 10 and the processing unit 50, 401 may be housed in a wearable client device 400A, such as a wearable watch-type client device 400A which can be worn on wrist, or a portable smart-phone-type client device 400B which can be carried or put on a nearby table. The auricular hybrid brain-computer interface system 105 may comprise wireless EEG electrodes 24, 25, 26, 27, wireless EOG electrodes 11, 12, that may be configured to be housed in one of the following: an earbud-type structure 61 or an in-the-ear portion 66 of a behind-the-ear-hearing-aid-style structure 63 or a tubular-shaped structure 67. (Wireless electrodes such as that described by Ryan Kaveh et al. in Nature Communications on Aug. 2, 2024. Wireless dry EEG electrodes are also available from Zeto, Inc. in Santa Clara, California). The EEG recording module 20 may have amplifiers and filters 22 that may comprise a wireless EEG amplifier, while the EOG recording module 10 may have amplifiers and filters 13 that may comprise a wireless EOG amplifier (such as those amplifiers made by the BIOPAC Systems, Inc. in Goleta, California). The EEG recording module 21 and the EOG recording module 10 may be housed in a wearable watch-type client device 400A or a portable smart-phone-type client device 400B.

In some embodiments, an auricular hybrid brain-computer interface system 105 may comprise an auricular EEG monitoring system 20 (with EEG recording module 21), and an auricular EOG system 101 (with EOG recording module 10). The auricular EEG monitoring system 20 is configured to assess the wearer's EEG profile. The EOG recording module 10 is configured to assess the wearer's EOG profile. The auricular hybrid brain-computer interface system 105 further comprises a network interface 85, 406, and at least one of the following: a speaker 86, 404A, a vibrator 87, 404B and a display screen 89, 404C (e.g. a display screen 404C on a client device 400 of the wearer 900 and/or a display screen 89 on the housing structure 60). Preferably, a speaker 86, 404A, a vibrator 87, 404B, and/or a display screen 89, 404C is in electronic communication with the network interface 85, 406. The processing unit 50, 401 is configured to send electronic signals to the network interface 85, 406. Preferably, the network interface 85, 406 is configured to send signals to the display screen 404C which is configured to generate a visible notification on the client device 400 of the wearer 900 describing the wearer's EOG profile and EEG profile. Optionally, the network interface 85, 406 is configured to send signals to the display screen 89 which is configured to generate a visible notification (with visual display) on the housing structure 60 describing the wearer's EOG profile and EEG profile, The human external ear canal 904 is a very unique location where EOG and EEG can be easily combined and function together and they can be effortlessly self-installed and self-removed. In the era of computer-brain interfaces (BCI), combining EOG and EEG into a single convenient and user-friendly device will create a more robust and more reliable hybrid BCI's with enormous usefulness.

In some embodiments, an auricular hybrid brain-computer interface (hBCI) system 105 may further comprise a novel auricular steady-state visual evoked potential (SS-VEP) system 38. The auricular SSVEP system 38 comprises a flickering light generator 38A that is configured to generate a light or pattern of light that flickers at a specific frequency and the light is shone to the wearer's eyes. Examples of flickering light generator 38A suitable for SSVEP include light emitting diodes (LED) or liquid crystal displays (LCD). The brain's response to the repeated flickering light stimulation (from the flickering light generator 38A) can be recorded by the EEG recording module 21 of the auricular EEG monitoring system 20 as steady-state visual evoked potential (SSVEP). The auricular EEG monitoring system 20 is in electronic communication with the processing unit 50, 401, which is configured to analyze the SSVEP data and the processing unit 50, 401, is configured to process the EEG data, the EOG data and the SSVEP data to guide the hybrid brain-computer interface (hBCI) system 105, utilizing hBCI algorithms (prior art). Additionally, other visual evoked potential (VEP) (such as P300 visual evoked potential) may be similarly utilized in hBCI system 105. P300 is a type of VEP that can be recorded by EEG that occurred about 300 milliseconds after a person's eyes are shone with a rare or sudden unexpected light In some embodiments, an auricular hBCI system 105 may further comprise an electromyogram (EMG) sensor 78 that is configured to record EMG data of the wearer 900 (for example: EMG of arm or hand muscles or jaw muscles). The EMG sensor 78 is in electronic communication with the processing unit 50, 401 and the processing unit 50, 401 is configured to analyze the EMG data. By utilizing hBCI algorithms (prior art), the processing unit 50, 401 is further configured to process the EEG data, the EOG data, and the EMG data to guide the hybrid brain-computer interface (hBCI) system 105.

Although this novel auricular hybrid brain-computer interface system 105 may be used for health monitoring, it may be configured to be used in a hybrid brain-computer interface (hBCI) system 105. The processing unit 50, 401 may be configured to analyze and process the EOG data (transmitted from the auricular EOG system 101) and EEG data (transmitted from the auricular EEG monitoring system 20) to guide the hybrid brain-computer interface (hBCI) system and to be used in the wheelchair control, control of robotic arms or legs, control of gaming devices and control of computer cursors or keyboards. There are major advantages in using signals received from the auricular EOG system 101 and the auricular EEG monitoring system 20 to guide the hybrid brain-computer interface system 105 since this auricular hBCI system 105 is very easy, convenient, wearable and non-invasive. No need for the very invasive and risky neural implant (surgery or other invasive procedure required) of conventional BCI device. The unique features of this auricular hybrid BCI system 105 (including features like free mobility, re-usability, simplicity, easy self-installation and self-removal etc.) will be very suitable for the robotics, wheelchair, gaming and automation fields. In the era of computer-brain interfaces (BCI) and robotics, combining EOG and EEG into a single convenient and user-friendly device will create a more robust and more reliable hybrid BCI's with enormous usefulness.

While some materials have been provided, in other embodiments, elements discussed herein may be made from or may comprise durable materials such as aluminum, steel, other metals and metal alloys, wood, hard rubbers, hard plastics, fiber reinforced plastics, carbon fiber, fiberglass, resins, polymers or any other suitable materials including combinations of materials. Additionally, one or more elements may be made from or may comprise durable and slightly flexible materials such as soft plastics, silicone, soft rubbers, or any other suitable materials including combinations of materials. In some embodiments, one or more of the elements discussed herein may be coupled or connected together with heat bonding, chemical bonding, adhesives, clasp type fasteners, clip type fasteners, rivet type fasteners, threaded type fasteners, other types of fasteners, or any other suitable joining method. In other embodiments, one or more of the elements discussed herein may be coupled or removably connected by being press fit or snap fit together, by one or more fasteners such as hook and loop type or Velcro® fasteners, magnetic type fasteners, threaded type fasteners, sealable tongue and groove fasteners, snap fasteners, clip type fasteners, clasp type fasteners, ratchet type fasteners, a push-to-lock type connection method, a turn-to-lock type connection method, a slide-to-lock type connection method or any other suitable temporary connection method as one reasonably skilled in the art could envision to serve the same function. In further embodiments, one or more of the elements discussed herein may be coupled by being one of connected to and integrally formed with another element of elements discussed herein.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. An auricular sleep monitoring system, the system comprising:

an auricular electroencephalogram (EEG) monitoring system comprising a first EEG recording module, wherein the first EEG recording module comprises a first set of a plurality of EEG electrodes, wherein the first EEG recording module is in electronic communication with each EEG electrode of the first set of a plurality of EEG electrodes, wherein the first EEG recording module is configured to record EEG data of a wearer via the first set of a plurality of EEG electrodes, wherein at least one EEG electrode of the first set of a plurality of EEG electrodes is configured to be housed in a first housing structure, wherein at least part of the first housing structure is configured to be inserted into an external ear canal of a first ear of the wearer when in use, and wherein the at least one EEG electrode of the first set of a plurality of EEG electrodes is configured to be naturally snugly in contact with the skin of the external ear canal of the wearer's first ear when the at least part of the first housing structure is inserted into the external ear canal of the wearer's first ear;

an ear-canal pulse oximeter, wherein the ear-canal pulse oximeter is a reflectance pulse oximeter having a reflectance oximeter module, wherein the reflectance oximeter module comprises a wired or wireless light generator, a wired or wireless light detecting sensor, and a detection module, wherein the wired or wireless light generator and the wired or wireless light detecting sensor are configured to be coupled to the external ear canal of the wearer's first ear to be in contact with the skin of the external ear canal of the wearer's first ear, wherein the wired or wireless light generator includes light-emitting diodes configured to emit light of different wavelengths, wherein the wired or wireless light detecting sensor is configured to measure the absorption of light of different wavelengths including red and infrared wavelengths, wherein the detection module is in electronic communication with the wired or wireless light generator and the wired or wireless light detecting sensor, and wherein the detection module is configured to analyze the data transmitted from the wired or wireless light generator and the data transmitted from the wired or wireless light detecting sensor to record the wearer's pulse data and blood oxygen saturation data; and a processing unit;

wherein the processing unit is in electronic communication with the auricular EEG monitoring system;

wherein the processing unit is in electronic communication with the ear-canal pulse oximeter; and wherein the processing unit is configured to analyze the EEG data from the EEG monitoring system and the pulse data and blood oxygen saturation data from the ear-canal pulse oximeter to assess the wearer's sleep profile and the wearer's pulse profile and blood oxygen saturation profile.

2. The auricular sleep monitoring system of claim 1, wherein each EEG electrode of the first set of a plurality of EEG electrodes and the light generator and the light detecting sensor of the ear-canal pulse oximeter are housed in a housing structure, wherein the housing structure is a tubular-shaped structure, wherein each EEG electrode of the first set of a plurality of EEG electrodes and the light generator and the light detecting sensor of the ear-canal pulse oximeter are partially embedded in a surface of the tubular-shaped structure with protrusion at the surface of the tubular-shaped structure, and wherein the tubular-shaped structure comprises a flexible elastic and adaptable material and the flexible elastic and adaptable material is configured to have appropriate flexibility, elasticity and adaptability such that each EEG electrode of the first set of a plurality of EEG electrodes and the light generator and the light detecting sensor of the ear-canal pulse oximeter are naturally and snugly in contact with the skin of the external ear canal of the wearer's first ear when the tubular-shaped structure is inserted into the external ear canal of the wearer's first ear.

3. The auricular sleep monitoring system of claim 1, wherein each EEG electrode of the first set of a plurality of EEG electrodes is configured to be a wireless EEG electrode, wherein the light generator and the light detecting sensor of the ear-canal pulse oximeter are configured as wireless light generator and wireless light detecting sensor, wherein the first EEG recording module comprises a wireless EEG amplifier, wherein the reflectance oximeter module comprises a wireless reflectance oximeter module, wherein each wireless EEG electrode of the first set of a plurality of EEG electrodes and the wireless light generator and the wireless light detecting sensor of the ear-canal pulse oximeter are housed in a housing structure, wherein the housing structure is a tubular-shaped structure, and wherein the EEG recording module, the wireless reflectance oximeter module and the processing unit are housed in one of the following: a wearable watch-type client device and a portable smartphone-type client device.

4. The auricular sleep monitoring system of claim 2, wherein the auricular sleep monitoring system further comprises a network interface, wherein the network interface is in electronic communication with the processing unit, wherein the network interface is configured to automatically generate a notification to a client device of the wearer immediately when the processing unit detects presence of the blood oxygen saturation dropping below a pre-determined level, wherein the network interface is further configured to automatically generate at least one notification to at least one of the following: a speaker that is in electronic communication with the processing unit and is configured to automatically generate an audible notification to the wearer immediately to alert the wearer to take appropriate action when the processing unit detects presence of the blood oxygen saturation dropping below the pre-determined level and a vibrator that is in electronic communication with the processing unit and is configured to automatically generate a tactile notification to the wearer immediately to alert the wearer to take appropriate action when the processing unit detects presence of the blood oxygen saturation dropping below the pre-determined level, wherein the auricular sleep monitoring system further comprises the following:

a display screen on the housing structure, wherein the network interface is in electronic communication with the display screen on the housing structure, wherein the network interface is configured to generate a visible notification on the display screen on the housing structure describing the wearer's sleep profile, pulse profile and blood oxygen saturation profile; and a display screen on the client device of the wearer, wherein the network interface in in electronic communication with the display screen on the client device of the wearer, wherein the network interface is configured to generate a visible notification on the display screen on the client device of the wearer describing the wearer's sleep profile, pulse profile and blood oxygen saturation profile.

5. A sleep monitoring system, the system comprising:

an auricular electroencephalogram (EEG) monitoring system comprising a first EEG recording module, wherein the first EEG recording module comprises a first set of a plurality of EEG electrodes, wherein the first EEG recording module is in electronic communication with each EEG electrode of the first set of a plurality of EEG electrodes, wherein the first EEG recording module is configured to record EEG data of a wearer via the first set of a plurality of EEG electrodes, wherein at least one EEG electrode of the first set of a plurality of EEG electrodes is configured to be housed in a first housing structure, wherein at least part of the first housing structure is configured to be inserted into an external ear canal of a first ear of the wearer when in use, and wherein the at least one EEG electrode of the first set of a plurality of EEG electrodes is configured to be naturally snugly in contact with the skin of the external ear canal of the wearer's first ear when the at least part of the first housing structure is inserted into the external ear canal of the wearer's first ear;

an ancillary sleep surveillance system, the ancillary sleep surveillance system comprising a pulse oximeter, wherein the pulse oximeter is configured to record pulse data of the wearer and blood oxygen saturation data of the wearer; and a processing unit;

wherein the processing unit is in electronic communication with the auricular EEG monitoring system;

wherein the processing unit is in electronic communication with the pulse oximeter of the ancillary sleep surveillance system; and wherein the processing unit is configured to analyze the EEG data from the EEG monitoring system and the pulse data and blood oxygen saturation data from the pulse oximeter of the ancillary sleep surveillance system to assess the wearer's sleep profile and the wearer's pulse profile and blood oxygen saturation profile.

6. The sleep monitoring system of claim 5, wherein the wearer's sleep profile comprises the wearer's sleep architecture, sleep stages, sleep latency, sleep density, sleep duration and sleep quality, wherein the sleep monitoring system is configured to assess the wearer's apnea-hypopnea index score, wherein the sleep monitoring system is further configured to detect presence or absence of obstructive sleep apnea, presence or absence of central sleep apnea, and presence or absence of sleep disorders, wherein the sleep disorders include the following: narcolepsy, restless leg syndrome, periodic limb movement disorder, parasomnias, and rapid-eye-movement (REM) sleep behavior disorder.

7. The sleep monitoring system of claim 5, wherein each EEG electrode of the first set of a plurality of EEG electrodes is housed in a housing structure, the housing structure selected from one of the following:

an earbud-style structure, wherein the earbud-style structure comprises a horizontal portion and each EEG electrode of the first set of a plurality of EEG electrodes is partially embedded in a surface of the horizontal portion with protrusion at the surface of the horizontal portion, wherein the horizontal portion comprises a flexible elastic and adaptable material and the flexible elastic and adaptable material is configured to have appropriate flexibility, elasticity and adaptability such that each EEG electrode of the first set of a plurality of EEG electrodes is naturally and snugly in contact with the skin of the external ear canal of the wearer's first ear when the horizontal portion is inserted into the external ear canal of the wearer's first ear, a behind-the-ear-hearing-aid-style structure, wherein the behind-the-ear-hearing-aid-style structure comprises an in-the-ear portion and a behind-the-ear portion, wherein each EEG electrode of the first set of a plurality of EEG electrodes is partially embedded in a surface of the in-the-ear portion with protrusion at the surface of the in-the-ear portion, wherein the in-the-ear portion comprises a flexible elastic and adaptable material and the flexible elastic and adaptable material is configured to have appropriate flexibility elasticity and adaptability such that each EEG electrode of the first set of a plurality of EEG electrodes is naturally and snugly in contact with the skin of the external ear canal of the wearer's first ear when the in-the-ear portion is inserted into the external ear canal of the wearer's first ear, and a tubular-shaped structure, wherein each EEG electrode of the first set of a plurality of EEG electrodes is partially embedded in a surface of the tubular-shaped structure with protrusion at the surface of the tubular-shaped structure, and wherein the tubular-shaped structure comprises a flexible elastic and adaptable material and the flexible elastic and adaptable material is configured to have appropriate flexibility, elasticity and adaptability such that each EEG electrode of the first set of a plurality of EEG electrodes is naturally and snugly in contact with the skin of the external ear canal of the wearer's first ear when the tubular-shaped structure is inserted into the external ear canal of the wearer's first ear.

8. The sleep monitoring system of claim 5, wherein each EEG electrode of the first set of a plurality of EEG electrodes is configured to be a wireless electrode, wherein the first EEG recording module comprises a wireless EEG amplifier, wherein each wireless EEG electrode of the first set of a plurality of EEG electrodes is housed in a housing structure, wherein the housing structure is selected from one of the following: an earbud-style structure, an in-the-ear portion of a behind-the-ear-hearing-aid-style structure, and a tubular-shaped structure, wherein the EEG recording module and the processing unit are housed in one of the following: a wearable watch-type client device and a portable smart-phone-type client device.

9. The sleep monitoring system of claim 7, further comprising a network interface, wherein the network interface is in electronic communication with the processing unit, wherein the network interface is configured to automatically generate a notification to a client device of the wearer immediately when the processing unit detects presence of obstructive sleep apnea, wherein the sleep monitoring system further comprises at least one of: a speaker that is in electronic communication with the network interface and is configured to automatically generate an audible notification to the wearer immediately to alert the wearer to take appropriate action when the processing unit detects presence of obstructive sleep apnea and a vibrator that is in electronic communication with the network interface and is configured to automatically generate a tactile notification to the wearer immediately to alert the wearer to take appropriate action when the processing unit detects presence of obstructive sleep apnea, wherein the sleep monitoring system further comprises the following:

a display screen on the housing structure, wherein the network interface is in electronic communication with the display screen on the housing structure, wherein the network interface is configured to generate a visible notification on the display screen on the housing structure describing the wearer's sleep profile, pulse profile and blood oxygen saturation profile; and a display screen on the client device of the wearer, wherein the network interface is in electronic communication with the display screen on the client device of the wearer, wherein the network interface is configured to generate a visible notification on the display screen on the client device of the wearer describing the wearer's sleep profile, pulse profile and blood oxygen saturation profile.

10. The sleep monitoring system of claim 5, wherein the auricular EEG monitoring system further comprises a second EEG recording module, wherein the second EEG recording module comprises a second set of a plurality of EEG electrodes, wherein the second EEG recording module is in electronic communication with each EEG electrode of the second set of a plurality of EEG electrodes, wherein each EEG electrode of the second set of a plurality of EEG electrodes is configured to be coupled to a second ear of the wearer or a peri-auricular area around the wearer's second ear, wherein when each EEG electrode of the second set of a plurality of EEG electrodes is coupled to the wearer's second ear or the peri-auricular area around the wearer's second ear each EEG electrode of the second set of a plurality of EEG electrodes is positioned in contact with separate locations on an area of the wearer, the area selected from at least one of the following: an external ear of the wearer's second ear, an external ear canal of the wearer's second ear, and the peri-auricular area around the wearer's second ear, wherein the second EEG recording module is configured to record EEG data of the wearer via the second set of a plurality of EEG electrodes, wherein processing unit is in electronic communication with the first EEG recording module and the second EEG recording module, and wherein the processing unit is configured to analyze the EEG data transmitted from the first EEG recording module and the EEG data transmitted from the second EEG recording module to assess the EEG profile of both sides of the brain of the wearer.

11. The sleep monitoring system of claim 5, wherein the pulse oximeter of the ancillary sleep surveillance system is an ear-canal pulse oximeter, wherein the ear-canal pulse oximeter is a reflectance pulse oximeter, wherein the reflectance pulse oximeter comprises a wired or wireless light generator, a wired or wireless light detecting sensor and a detection module, wherein the wired or wireless light generator and the wired or wireless light detecting sensor are configured to be coupled to the external ear canal of the wearer's first ear to be in contact with the skin of an external ear canal of the wearer's first ear, wherein the wired or wireless light generator includes light-emitting diodes configured to emit light of different wavelengths, wherein the wired or wireless light detecting sensor is configured to measure the absorption of light of different wavelengths including red and infrared wavelengths, wherein the detection module is in electronic communication with the wired or wireless light generator and the wired or wireless light detecting sensor, wherein the detection module is configured to analyze the data transmitted from the wired or wireless light generator and data transmitted from the wired or wireless light detecting sensor to assess pulse data and blood oxygen saturation data of the wearer, and wherein the ear-canal pulse oximeter is in wireless communication with the processing unit.

12. The sleep monitoring system of claim 5, further comprising an auricular electrooculogram (EOG) system, wherein the auricular EOG system comprises an EOG recording module, wherein the EOG recording module comprises at least two EOG electrodes, wherein the EOG recording module is in electronic communication with each EOG electrode of the at least two EOG electrodes, wherein each EOG electrode of the at least two EOG electrodes is configured to be coupled to a wearer's first ear or a peri-auricular area around the wearer's first ear, wherein when each EOG electrode of the at least two EOG electrodes is coupled to the wearer's first ear or the peri-auricular area around the wearer's first ear each EOG electrode of the at least two EOG electrodes is positioned in contact with separate locations on a first area of the wearer, the first area selected from at least one of the following: an external ear of the wearer's first ear, an external ear canal of the wearer's first ear, and the peri-auricular area around the wearer's first ear, wherein the EOG recording module is configured to record EOG data of the wearer via each EOG electrode of the at least two EOG electrodes, wherein the processing unit is in electronic communication with the auricular EOG system, wherein the processing unit is in electronic communication with the auricular EEG monitoring system, wherein the processing unit is in electronic communication with the ancillary sleep surveillance system; and wherein the processing unit is configured to analyze the EOG data from the auricular EOG system, the EEG data from the auricular EEG monitoring system, and the data from the ancillary sleep surveillance system to assess the wearer's sleep profile.

13. The sleep monitoring system of claim 12, further comprising an auricular electrocardiogram (ECG) system, the auricular ECG system comprising an auricular ECG recording module, wherein the auricular ECG recording module comprises at least two ECG electrodes, wherein the ECG recording module is in electronic communication with each ECG electrode of the at least two ECG electrodes, wherein each ECG electrode of the at least two ECG electrodes is configured to be coupled to the wearer's first ear or the peri-auricular area around the wearer's first ear, wherein when each ECG electrode of the at least two ECG electrodes is coupled to the wearer's first ear or the peri-auricular area around the wearer's first ear each ECG electrode of the at least two ECG electrodes is positioned in contact with separate locations on an second area of the wearer, the second area selected from at least one of the following: the external ear of the wearer's first ear, the external ear canal of the wearer's first ear, and the peri-auricular area around the wearer's first ear, and wherein the ECG recording module is configured to record ECG data of the wearer via the at least two ECG electrodes, wherein the ECG recording module is in electronic communication with the processing unit, and wherein the processing unit is configured to analyze the EEG data from the EEG monitoring system, the EOG data from the EOG monitoring system, the ECG data from the ECG recording module, and the data from the ancillary sleep surveillance system to assess the wearer's sleep profile.

14. The sleep monitoring system of claim 12, wherein the auricular EEG monitoring system further comprises a second EEG recording module, wherein the second EEG recording module comprises a second set of a plurality of EEG electrodes, wherein the second EEG recording module is in electronic communication with each EEG electrode of the second set of a plurality of EEG electrodes, wherein each EEG electrode of the second set of a plurality of EEG electrodes is configured to be coupled to a second ear of the wearer or a peri-auricular area around the wearer's second ear, wherein when each EEG electrode of the second set of a plurality of EEG electrodes is coupled to the wearer's second ear or the peri-auricular area around the wearer's second ear each EEG electrode of the second set of a plurality of EEG electrodes is positioned in contact with separate locations on an area of the wearer, the area selected from at least one of the following: an external ear of the wearer's second ear, an external ear canal of the wearer's second ear, and the peri-auricular area around the wearer's second ear, and wherein the second EEG recording module is configured to record EEG data of the wearer via the second set of a plurality of EEG electrodes, wherein the processing unit is in electronic communication with the first EEG recording module and the second EEG recording module, and wherein the processing unit is configured to analyze the EEG data transmitted from the first EEG recording module and the EEG data transmitted from the second EEG recording module to assess the EEG profile of both sides of the brain of the wearer.

15. The sleep monitoring system of claim 12, wherein each EOG electrode of the at least two EOG electrodes and each EEG electrode of the first set of a plurality of EEG electrodes are housed in a housing structure, the housing structure selected from one of the following: an earbud-style structure, a behind-the-ear-hearing-aid-style structure, or a tubular-shaped structure, wherein the earbud-style structure comprises a horizontal portion, wherein each EEG electrode of the first set of a plurality of EEG electrodes is partially embedded in a surface of the horizontal portion with protrusion at the surface of the horizontal portion, wherein each EOG electrode of the at least two EOG electrodes is partially embedded in the surface of the horizontal portion with protrusion at the surface of the horizontal portion, wherein the horizontal portion comprises a flexible elastic and adaptable material and the flexible elastic and adaptable material is configured to have appropriate flexibility, elasticity and adaptability such that each EOG electrode of the at least two EOG electrodes and each EEG electrode of the first set of a plurality of EEG electrodes are naturally and snugly in contact with the skin of the external ear canal of the wearer's first ear when the horizontal portion is inserted into the external ear canal of the wearer's first ear, wherein the behind-the-ear-hearing-aid-style structure comprises an in-the-ear portion and a behind-the-ear portion, wherein each EOG electrode of the at least two EOG electrodes and each EEG electrode of the first set of a plurality of EEG electrodes, are partially embedded in a surface of the in-the-ear portion with protrusion at the surface of the in-the-ear portion, wherein the in-the-ear portion comprises a flexible elastic and adaptable material and the flexible elastic and adaptable material is configured to have appropriate flexibility, elasticity and adaptability such that each EOG electrode of the at least two EOG electrodes, and each EEG electrode of the first set of a plurality of EEG electrodes are naturally and snugly in contact with the skin of the external ear canal of the wearer's first ear when the in-the-ear portion is inserted into the external ear canal of the wearer's first ear, wherein if the tubular-shaped structure is selected as the housing structure, each EEG electrode of the first set of a plurality of EEG electrodes is partially embedded in a surface of the tubular-shaped structure with protrusion at the surface of the tubular-shaped structure, wherein each EOG electrode of the at least two EOG electrodes is partially embedded in the surface of the tubular-shaped structure with protrusion at the surface of the tubular-shaped structure, and wherein the tubular-shaped structure comprises a flexible elastic and adaptable material and the flexible elastic and adaptable material is configured to have appropriate flexibility, elasticity and adaptability such that each EOG electrode of the at least two EOG electrodes and each EEG electrode of the first set of a plurality of EEG electrodes are naturally and snugly in contact with the skin of the external ear canal of the wearer's first ear when the tubular-shaped structure is inserted into the external ear canal of the wearer's first ear.

16. The sleep monitoring of claim 13, wherein the pulse oximeter is configured as an ear-canal pulse oximeter, wherein the ear-canal pulse oximeter is a reflectance pulse oximeter, wherein the reflectance pulse oximeter comprises a wired or wireless light generator, a wired or wireless light detecting sensor, and a detection module, wherein the wired or wireless light generator and the wired or wireless light detecting sensor are configured to be coupled to the external ear canal of the wearer's first ear to be in contact with the skin of the external ear canal of the wearer's first ear, wherein the wired or wireless light generator includes light-emitting diodes configured to emit light of different wavelengths, wherein the wired or wireless light detecting sensor is configured to measure the absorption of light of different wavelengths including red and infrared wavelengths, wherein the detection module is in electronic communication with the wired or wireless light generator and the wired or wireless light detecting sensor, wherein the detection module is configured to analyze the data transmitted from the wired or wireless light generator and data transmitted from the wired or wireless light detecting sensor to record the wearer's pulse data and blood oxygen saturation data, and wherein the ear-canal pulse oximeter is in electronic communication with the processing unit, and wherein the processing unit is configured to analyze the EEG data from the EEG monitoring system, the EOG data from the EOG monitoring system, the ECG data from the ECG recording module, the data from the ancillary sleep surveillance system and pulse data and blood oxygen saturation data from the ear-canal pulse oximeter to assess the wearer's sleep profile.

17. The sleep monitoring system of claim 12, further comprising a network interface and further comprising at least one of the following: a speaker, a vibrator, a display screen on the housing structure and a display screen on a client device, wherein the network interface is in electronic communication with the processing unit, wherein the processing unit is configured to analyze the EEG data transmitted from the auricular EEG monitoring system, the EOG data transmitted from the auricular EOG system and the data from the ancillary surveillance system to assess the wearer's sleep profile and to detect presence of obstructive sleep apnea of the wearer, wherein the network interface is in electronic communication with the display screen on the housing structure and the display screen on the client device, wherein the network interface is configured to generate a visible notification on at least one of the display screen on the housing structure and the display screen on the client device of the wearer describing the wearer's sleep profile, wherein the network interface is further configured to automatically generate a notification to the client device of the wearer immediately when the processing unit detects presence of obstructive sleep apnea, wherein the speaker is in electronic communication with the network interface, wherein the speaker is configured to automatically generate an audible notification to the wearer immediately to alert the wearer to take appropriate action when the processing unit detects presence of obstructive sleep apnea, wherein the vibrator is in electronic communication with the network interface, and wherein the vibrator is configured to automatically generate a tactile notification to the wearer immediately to alert the wearer to take appropriate action when the processing unit detects presence of obstructive sleep apnea.

18. The sleep monitoring system of claim 12, wherein each EOG electrode of the at least two EOG electrodes is configured as a wireless EOG electrode, wherein each EEG electrode of the first set of a plurality of EEG electrodes is configured as a wireless EEG electrode, wherein the EEG recording module comprises a wireless EEG amplifier, wherein the EOG recording module comprises a wireless EOG amplifier, wherein each wireless EOG electrode of the at least two EOG electrodes, and each wireless EEG electrode of the first set of a plurality of EEG electrodes, are housed in a housing structure, wherein the housing structure is selected from one of the following: an earbud-style structure, a behind-the-ear-hearing-aid-style structure, and a tubular-shaped structure, and wherein the EEG recording module, the EOG recording module, and the processing unit are housed in one of the following: a wearable watch-type structure and a portable smart-phone-type structure.

19. The sleep monitoring system of claim 16, wherein each EOG electrode of the at least two EOG electrodes, each EEG electrode of the first set of a plurality of EEG electrodes, each ECG electrode of the at least two ECG electrodes and the light generator and light detecting sensor of the ear-canal pulse oximeter are housed in a housing structure, the housing structure selected from one of the following: an earbud-style structure, a behind-the-ear-hearing-aid-style structure, or a tubular-shaped structure, wherein the earbud-style structure comprises a horizontal portion, wherein each EEG electrode of the first set of a plurality of EEG electrodes is partially embedded in a surface of the horizontal portion with protrusion at the surface of the horizontal portion, wherein each EOG electrode of the at least two EOG electrodes is partially embedded in the surface of the horizontal portion with protrusion at the surface of the horizontal portion, wherein each ECG electrode of the at least two ECG electrodes is partially embedded in the surface of the horizontal portion with protrusion at the surface of the horizontal portion, wherein the light generator and light detecting sensor of the ear-canal pulse oximeter are partially embedded in the surface of the horizontal portion with protrusion at the surface of the horizontal portion, wherein the horizontal portion comprises a flexible elastic and adaptable material and the flexible elastic and adaptable material is configured to have appropriate flexibility, elasticity and adaptability such that each EOG electrode of the at least two EOG electrodes, each ECG electrode of the at least two ECG electrodes, each EEG electrode of the first set of a plurality of EEG electrodes and the light generator and light detecting sensor of the ear-canal pulse oximeter are naturally and snugly in contact with the skin of the external ear canal of the wearer's first ear when the horizontal portion is inserted into the external ear canal of the wearer's first ear, wherein the behind-the-ear-hearing-aid-style structure comprises an in-the-ear portion and a behind-the-ear portion, wherein each EOG electrode of the at least two EOG electrodes, each ECG electrode of the at least two ECG electrodes, each EEG electrode of the first set of a plurality of EEG electrodes and the light generator and light detecting sensor of the ear-canal pulse oximeter are partially embedded in a surface of the in-the-ear portion with protrusion at the surface of the in-the-ear portion, wherein the in-the-ear portion comprises a flexible elastic and adaptable material and the flexible elastic and adaptable material is configured to have appropriate flexibility, elasticity and adaptability such that each EOG electrode of the at least two EOG electrodes, each ECG electrode of the at least two ECG electrodes, each EEG electrode of the first set of a plurality of EEG electrodes and the light generator and light detecting sensor of the ear-canal pulse oximeter are naturally and snugly in contact with the skin of the external ear canal of the wearer's first ear when the in-the-ear portion is inserted into the external ear canal of the wearer's first ear, wherein if the tubular-shaped structure is selected as the housing structure, each EEG electrode of the first set of a plurality of EEG electrodes is partially embedded in a surface of the tubular-shaped structure with protrusion at the surface of the tubular-shaped structure, wherein each EOG electrode of the at least two EOG electrodes is partially embedded in the surface of the tubular-shaped structure with protrusion at the surface of the tubular-shaped structure, wherein each ECG electrode of the at least two ECG electrodes is partially embedded in the surface of the tubular-shaped structure with protrusion at the surface of the tubular-shaped structure, wherein the light generator and light detecting sensor of the ear-canal pulse oximeter are partially embedded in the surface of the tubular-shaped structure with protrusion at the surface of the tubular-shaped structure, and wherein the tubular-shaped structure comprises a flexible elastic and adaptable material and the flexible elastic and adaptable material is configured to have appropriate flexibility, elasticity and adaptability such that each EOG electrode of the at least two EOG electrodes, each EEG electrode of the first set of a plurality of EEG electrodes, each ECG electrode of the at least two ECG electrodes and the light generator and light detecting sensor of the ear-canal pulse oximeter are naturally and snugly in contact with the skin of the external ear canal of the wearer's first ear when the tubular-shaped structure is inserted into the external ear canal of the wearer's first ear.

20. The sleep monitoring system of claim 16, wherein the sleep monitoring system is configured as a health monitoring system that is configured to monitor the wearer's health profiles when the wearer is not sleeping, wherein the wearer's health profiles include an extra-ocular eye movement profile of the wearer, an electroencephalographic profile of the wearer, an electrocardiographic profile of the wearer and a pulse profile and blood oxygen saturation profile of the wearer, wherein the processing unit is configured to analyze the EOG data as recorded by the EOG recording module, the EEG data as recorded by the EEG recording module, the ECG data as recorded by the ECG recording module and the pulse data and blood oxygen saturation data as recorded by the ear-canal pulse oximeter to assess the extra-ocular eye movement profile of the wearer, the electroencephalographic profile of the wearer, the electrocardiographic profile of the wearer and the pulse profile and blood oxygen saturation profile of the wearer.

21. A sleep monitoring system, the system comprising:
an auricular electroencephalogram (EEG) monitoring system comprising a first EEG recording module, wherein the first EEG recording module comprises a first set of a plurality of EEG electrodes, wherein each EEG electrode of the first set of a plurality of EEG electrodes is configured to be coupled to a wearer's first ear or a peri-auricular area around the wearer's first ear, wherein the first EEG recording module is in electronic communication with each EEG electrode of the first set of a plurality of EEG electrodes, wherein when the first set of a plurality of EEG electrodes are coupled to the wearer's first ear or the peri-auricular area around the wearer's first ear the first set of a plurality of EEG electrodes are positioned in contact with separate locations on a first area of the wearer, the first area selected from at least one of the following: an external ear of the wearer's first ear, an external ear canal of the wearer's first ear, and the peri-auricular area around the wearer's first ear, and wherein the first EEG recording module is configured to record EEG data of the wearer via the first set of a plurality of EEG electrodes;

an auricular electrooculogram (EOG) system, wherein the auricular EOG system comprises an EOG recording module, wherein the EOG recording module comprises at least two EOG electrodes, wherein the EOG recording module is in electronic communication with each EOG electrode of the at least two EOG electrodes, wherein each EOG electrode of the at least two EOG electrodes is configured to be coupled to the wearer's first ear or the peri-auricular area around the wearer's first ear, wherein when each EOG electrode of the at least two EOG electrodes is coupled to the wearer's first ear or the peri-auricular area around the wearer's first ear each EOG electrode of the at least two EOG electrodes is positioned in contact with separate locations on a second area of the wearer, the second area selected from at least one of the following: the external ear of the wearer's first ear, the external ear canal of the wearer's first ear, and the peri-auricular area around the wearer's first ear, and wherein the EOG recording module is configured to record EOG data of the wearer via the at least two EOG electrodes;

an auricular electrocardiogram (ECG) system, the auricular ECG system comprising an auricular ECG recording module, wherein the auricular ECG recording module comprises at least two ECG electrodes, wherein the ECG recording module is in electronic communication with each ECG electrode of the at least two ECG electrodes, wherein each ECG electrode of the at least two ECG electrodes is configured to be coupled to the wearer's first ear or the peri-auricular area around the wearer's first ear, wherein when each ECG electrode of the at least two ECG electrodes is coupled to the wearer's first ear or the peri-auricular area around the wearer's first ear each ECG electrode of the at least two ECG electrodes is positioned in contact with separate locations on a third area of the wearer, the third area selected from at least one of the following: the external ear of the wearer's first ear, the external ear canal of the wearer's first ear, and the peri-auricular area around the wearer's first ear, and wherein the ECG recording module is configured to record ECG data of the wearer via the at least two ECG electrodes;

an ancillary sleep surveillance system, the ancillary sleep surveillance system comprising a pulse oximeter configured to record pulse data and blood oxygen saturation data of the wearer; and a processing unit, wherein the processing unit is in electronic communication with the auricular EEG monitoring system, the auricular EOG system and the auricular ECG system;

wherein the processing unit is configured to analyze the EEG data of the wearer, the EOG data of the wearer and the ECG data of the wearer for artifacts detection and digital subtraction of each other's interferences and use algorithms and processing techniques in digital subtraction for removal of ECG artifacts and eye movement artifacts from the EEG data of the wearer;

wherein the processing unit is in electronic communication with the pulse oximeter of the ancillary sleep surveillance system; and wherein the processing unit is configured to analyze the EEG data from the EEG monitoring system the EOG data from the EOG recording module and the ECG data from the ECG recording module and the pulse data and blood oxygen saturation data from the pulse oximeter of the ancillary sleep surveillance system to assess the wearer's sleep profile and the wearer's EEG profile, EOG profile, ECG profile, pulse profile and blood oxygen saturation profile.

22. The sleep monitoring system of claim 21, wherein the wearer's sleep profile comprises the wearer's sleep architecture, sleep stages sleep latency, sleep density, sleep duration and sleep quality, wherein the sleep monitoring system is configured to assess the wearer's apnea-hypopnea index score, wherein the sleep monitoring system is further configured to detect presence or absence of obstructive sleep apnea, presence or absence of central sleep apnea, and presence or absence of sleep disorders, wherein the sleep disorders include the following: narcolepsy, restless leg syndrome, periodic limb movement disorder, parasomnias, and rapid-eye-movement (REM) sleep behavior disorder.

* * * * *